«12» United States Patent
Demmer et al.

US007538260B2

(10) Patent No.: US 7,538,260 B2
(45) Date of Patent: May 26, 2009

(54) COMPOSITIONS ISOLATED FROM FORAGE GRASSES AND METHODS FOR THEIR USE

(76) Inventors: Jeroen Demmer, 33B Glenvar Rd, Torbay, Auckland (NZ); Claire Hall, 3/253 Kepa Road, Mission Bay, Auckland (NZ); Michael Geoffrey Norriss, 16 Ilam Road, Riccarton, Christchurch (NZ); Keith Martin Saulsbury, 8 Samuel Street, Christchurch (NZ)

( * ) Notice: Subject to any disclaimer, the term of this patent is extended or adjusted under 35 U.S.C. 154(b) by 266 days.

(21) Appl. No.: 11/110,082

(22) Filed: Apr. 19, 2005

(65) Prior Publication Data

US 2005/0266558 A1    Dec. 1, 2005

Related U.S. Application Data

(63) Continuation-in-part of application No. 10/655,799, filed on Sep. 5, 2003, now Pat. No. 7,265,278.

(60) Provisional application No. 60/563,723, filed on Apr. 20, 2004, provisional application No. 60/408,782, filed on Sep. 5, 2002.

(51) Int. Cl.
  *C12N 15/29*    (2006.01)
  *C12N 15/82*    (2006.01)
  *A01H 5/00*     (2006.01)
(52) U.S. Cl. ................. 800/290; 800/287; 800/298; 536/23.1; 536/23.6; 435/419
(58) Field of Classification Search ............... None
  See application file for complete search history.

(56) References Cited

FOREIGN PATENT DOCUMENTS

| EP | 1 033 405 A2 | 9/2000 |
|---|---|---|
| WO | WO 99/09174 | 2/1999 |
| WO | WO 02/38768 A1 | 5/2002 |
| WO | WO 02/44390 | 6/2002 |
| WO | WO 02/44390 A2 * | 6/2002 |
| WO | WO 03/000904 | 1/2003 |
| WO | WO 03/048319 | 6/2003 |

OTHER PUBLICATIONS

Document 11;Result 5, (AAD44250) pp. 1-2.*
Document 12; Result 7, (AAE25748) pp. 1-2.*
Davies B. et al., The EMBO Journal, 1999; vol. 18, No. 14 pp. 4023-4034.*
Colasanti, J., et al., "The *Indeterminate* Gene Encodes a Zinc Finger Protein and Regulates a Leaf-Generated Signal Required for the Transition to Flowering to Flowering in Maize," *Cell*, (1998), 593-603; vol. 93.
Alexandrov, N., et al., "New sequence determined DNA fragments (SDFs) from different plant species, e.g. corn, rice or Arabidopsis thaliana, useful as promoters, protein coding sequences, untranslated regions, or as 3' termination sequences," DGENE, (Sep. 2000), Accession No. AAG55040.

(MITU) Mitsubishi Chem Corp., "Gene involved in high accumulation of cadmium, useful for producing transformants used in phytoremediation -," DGENE, (Apr. 2002), Accession No. AAU98435.
Yano, M., et al., "Hd3a gene for inducing flowering of plants with modification to flowering time by transferring the gene or controlling its expression, useful in improving plant breeds, e.g. rice to adapt cultivation region and time," DGENE, (May 2002), Accession No. ABG31338.
Minami, et al., "Method for identifying gibberellin responsive genes useful for producing genetically modified plants," DGENE, (Jul. 2003), Accession No. ADC47019.
Ten Hoopen, R., et al., "Evolutionary conservation of kinetochore protein sequences in plants," NCBI Databases, (2000), Accession No. CAB85491.
Aronson, M.N., et al., "Clink, a nanovirus-encoded protein, binds both pRB and SKP1," NCBI Databases, (2000), Accession No. AAD34458.
Samach, A., et al., "The Unusual Floral Organs gene of Arabidopsis thaliana is an F-box protein required for normal patterning and growth in the floral meristem," NCBI Databases, (1999), Accession No. AAC63110.
Luo, M., et al., "Cloning of a novel barley gene encoding a protein that binds abscisic acid," NCBI Databases, (2000), Accession No. AAF97846.
Kojima, S., et al., "Hd3a, a quantative trait locus, involves in the promotion of flowering in rice," NCBI Databases, (2000), Accession No. BAB61027.
Peng, J., et al., "Green revolution' genes encode mutant gibberellin response modulators," NCBI Databases, (1999), Accession No. CAB51557.
Chandler, P.M., et al., "Mutants at the Slender1 Locus of Barley cv Himalaya. Molecular and Physiological Characterization," NCBI Databases, (2002), Accession No. AAL66734.
Jensen, C.S., et al., A Terminal Flower1-like gene from perennial ryegrass involved in floral transition and axillary meristem identity, NCBI Databases (2001), Accession No. AAG310808.
Conner, J., et al., "Leunig, a putative transcriptional corepressor that regulates AGAMOUS expression during flower development," NCBI Databases, (2000), Accession No. AAG32022.
Peng, J., et al., "Green revolution' genes encode mutant gibberellin response modulators," NCBI Databases, (1999), Accession No. CAB51555.

\* cited by examiner

*Primary Examiner*—Russell Kallis
(74) *Attorney, Agent, or Firm*—Janet Sleath; Speckman Law Group PLLC

(57) ABSTRACT

Isolated polynucleotides encoding polypeptides that regulate flowering are provided, together with expression vectors and host cells comprising such isolated polynucleotides. Methods for the use of such polynucleotides and polypeptides are also provided.

17 Claims, 12 Drawing Sheets

Fig. 1

MAAEDKKITLKSSDGEQFEVDEAVAMESQTIRHMIEDDCADNGIPLPNVNAKILSKVVEYCSKHVQAADGA
AAADGAPAPPPAEDLKNWDAEFVKVDQATLFDLILAANYLNIKGLLDLTCQTVADMIKGKTPEEIRKTFNI
KNDFTAEEEEEIRRENQWAFE

Fig. 2

MAAADDSKKMITLKSSDGEVFEVEEAVAMESQTIRHMIEDDCADNGIPLPNVNSKILSKVIEYCNKHVQAA
KPAADAAAADSSSAAAPPEDLKNWDAEFVKVDQATLFDLILAANYLNIKGLLDLTCQTVADMIKGKTPEEI
RKTFNIKNDFTAEEEEEIRRENQWAFE

Fig. 3

SDGEEFEVEEVLVLESQTIKHMIEDECDGVIPLPNVSAKILSKVIEYCRKHVQTRAALAPDGDMSTNAAGT
ELKTFDEDFVKVDQATLFDLILAANYLDIKGLLDLTCQTVADMIKGKTPEEIRATFNIKNDFTPEEEEEVR
KENAWAFE

Fig. 4

GGRGDYSDHDNKSGHVKLFVGSVPRTASEDDVRPLFENHGDVLEVAMIRDRKTGEQQGCCFVKYATSEEAE
RAIRALHNQWTIPGAMGPVQVRYADGEKERHGSIEHKLFVASLNKQATAKEIEEIFAPFGHVEDVYIMKDG
MKQSRGCGFVKFSSKEPALAAMNSLSGTYIMRGCEQPLIVRFADPKRPRPGESRWLRMHICFAYIPTLHYF
PLLLSELSCLVRGGPAFGGPGVSPRSDAALVIRPTANLDEPRGRHMPRDAWRPSSPSSVAPHQFNNYGSDN
PMGLMGGTGTSATDNGAFRPQMFPGNGQTAVPTSSHMGINTSSVQGHHLGGQQIPPLQKPPGPPHNFSLQL
QNQQGQHSLGPGLFGQNVPSMQLPGQLPTSQPLTQQNASAGALQVPPAIQSNPMQSVPGQQQLPSNVAAQM
MQQPIQQIPSQAPQLLLQQQAAMQSSYQSSQQAIFQLQQQLQLMQQQQQQQQQPNLNQQPHTQISKQQGQP
NQSSTPGAPAAMMPSNINAIPQQVNSPVV*SLTCNWTEHTSPEGFKYYYNSITRESKWEKPEE*YVLYEQQQQ
QQHQKLILLQQHQQKLVAQQLQSPPQAQTIQSMQSIQQHPQSHQGHNQMQMKHQELNYNQLQATGNIDPNR
IQQGIQAAQERSWKS

Fig. 5

GGRGDYSDHDNKSGHVKLFVGSVPRTASEDDVRPLFENHGDVLEVAMIRDRKTGEQQGCCFVKYATSEEAE
RAIRALHNQWTIPGAMGPVQVRYADGEKERHGSIEHKLFVASLNKQATAKEIEEIFAPFGHVEDVYIMKDG
MKQSRGCGFVKFSSKEPALAAMNSLSGTYIMRRPRPGESRGGPAFGGPGVSPRSDAALVIRPTANLDEPRG
RHMPRDAWRPSSPSSVASHQFNNYGSDNPMGIMGGTGTSAADNGAFRPQMFPGNGQTAVPTSSHMGINTSL
QGHHLGGQQIPPLQKPPGPPHNFSLQLQNQQGQHSLVPGLFGQNVPSMQLPGQLPTSQPLTQQNASAGALQ
APPAIQSNPMQSVPGQQQLPSNVAPQMMQQPIQQIPSQAPQLLLQQQAAMQSSYQSSQQAIFQLQQQLQLM
QQQQQQQQQPNLNQQQPNLNQQQHTQISKQQGQPNQSSTPGAPAAMMPSNINAIPQQVNSPAV***SLTCNWTE
HTSPEGFKYYYNSITRESKWEKPEE***YVLYEQQQQQQQQQKLILLQQHQQKLVAQQLQSPPQAQTIQSMQSI
QQHPQSHQGHNQMQMKHQELNYNQLQATGNIDPNRIQQGIQAAQERSWKS

Fig. 6

MAGRDRDPLVVGRVVGDVLDPFVRTTNLRVTFGNRAVSNGCELKPSMVTHQPRVEVGGNEMRTF YTLVMVD
PDAPSPSDPNLREYL HWLVTDIPGTTGASFGQEVMCYESPRPNMGIHRFVLVLFQQLGRQTVYAPGWRQNF
NTRDFAELYNLGPAVAAVYFNCQREAGSGGRRMYN

Fig. 7

MVGVQRADPLVVGRVIGDVVDPFVRRVPLRVGYASRDVANGCELRPSAIADQPRVEVGGPDMRTF YTLVMV
DPDAPSPSDPSLREYL HW

Fig. 8

EAFAGCRRVHVVDFGIKQGMQWPALLQALALRPGGPPSFRLTGVGPPQPDETDALQQVGWKLAQFAHTIGV
DFQYRGLVAATLADLEPFMLQPEADDGPNEEPEVIAVNSVFEMHRLLAQPGALEKVLGTVRAVRPRIVTVV
EQEANHNTGSFLDRFTESLHYYSTMFDSLEGAGSAPSEISSGPSAAAANAAAPGTDQVMSEVYLGRQICNV
VACEGAERTERHETLGQWRGRLGHAGFETVHLGSNAYKQASTLLALFAGGDGYKVDEKEGCLTLGWHTRPL
IATSAWRMAAAAAP

Fig. 9

MSVSNGKWIDGLQFSSLFWPPPHDAQQKQAQTLAYVEYFGQFTSDSEQFPEDVAQLIQSYYPSKEKRLVDE
VLATFVLHHPEHGHAVVHPILSRIIDGSLSYDRHGSPFNSFISLFTQTAEKEYSEQWALACGEILRVLTHY
NRPIFKVAECNDTSDQATTSYSLHDKANSSPENEPERKPLRPLSPWITDILLNAPLGIRSDYFRWCGGVMG
KYAAGGELKPPTTAYSRGAGKHPQLMPSTPRWAVANGAGVILSVCDEEVARYETANLTAAAVPALLLPPPT
TPLDEHLVAGLPPLEPYARLFHRYYAIATPSATQRLLFGLLEAPPSWAPDALDAAVQLVELLRAAEDYATG
MRLPKNWLHLHFLRAIGTAMSMRAGMAADTAAALLFRILSQPTLLFPPLRHAEGVVQHEPLGGYVSSYKRQ
LEIPASETTIDATAQGIASLLCAHGPDVEWRICTIWEAAYGLLPLNSSAVDLPEIVVAAPLQPPTLSWSLY
LPLLKVFEYLPRGSPSEACLMRIFVATVEAILRRTFPSETEPSKKPRSPSKSLAVAELRTMIHSLFVESCA
SMNLASRLLFVVLTVSVSHQALPGGSKRPTGSENHSSEESTEDSKLTNGRNRCKKKQGPVGTF DSYVLAAV
CALSCELQLFPILCKNVTKTNIKDSIKITMPGKTNGISNELHNSVNSAILHTRRILGILEALFSLKPSSVG
TSWSYSSNEIVAAAMVAAHVSELFRRSRPCLNALSALKRCKWDAEISTRASSLYHLIDLHGKTVSSIVNKA
EPLEAHLNLTAVKKDDQHHIEESNTSSSDYGNLEKKSKKNGFSRPLMKCAEQARRNGNVASTSGKATATLQ
AEASDLANFLTMDRNGGYGGSQTLLRTVMSEKQELCFSVVSLLWHKLIASPETQMSAESTSAHQGWRKVAD
ALCDVVSASPAKASTAIVLQAEKDLQPWIARDDEQGQKMWRVNQRIVKLIAELMRNHDSPEALIILASASD
LLLRATDGMLVDGEACTLPQLELLEVTARAIHLIVEWGDPGVAVADGLSNLLKCRLSPTIRCLSHPSAHVR
ALSMSVLRDILNSGPISSTKIIQGEQRNGIQSPSYRCAAASMTNWQADVERCIEWEAHNR QATGMTLAFLT
AAANELGCPLPC

Fig. 10

MSASNGKWIDGLQFSSLFWPPPHDAQQKQAQTLAYVEYFGQFTSDSEQFPEDVAQLIQSCYPSKEKRLVDE
VLATFVLHHPEHGHAVVHPILSRIIDGSLSYDRHGSPFNSFISLFTQTAEKEYSEQWALACGEILRVLTHY
NRPIFKVAECNDTSDQATTSYSLQEKANSSPENEPERKPLRPLSPWITDILLNAPLGIRSDYFRWCGGVMG
KYAAGGELKPPTTAYSRGAGKHPQLMPSTPRWAVANGAGVILSVCDEEVARYETANLTAAAVPALLLPPPT
TPLDEHLVAGLPPLEPYARLFHRYYAIATPSATQRLLFGLLEAPPSWAPDALDAAVQLVELLRAAEDYATG
MRLPKNWLHLHFLRAIGTAMSMRAGMAADTAAALLFRILSQPTLLFPPLRHAEGVVQHEPLGGYVSSYKRQ
LEIPASETTIDATAQGIASLLCAHGPDVEWRICTIWEAAYGLLPLNSSAVDLPEIVVAAPLQPPTLSWSLY
LPLLKVFEYLPRGSPSEACLMRIFVATVEAILRRTFPSETSEPSKKPRSPSKSLAVAELRTMIHSLFVESC
ASMNLASRLLFVVLTVSVSHQALPGGSKRPTGSDNHSSEESTEDSKLTNGRNRCKKKQGPVGTFDSYVLAA
VCALSCELQLFPILCKNVTKSNIKDSIKITMPGKTNGISNELHNSVNSAVLHTRRILGILEALFSLKPSSV
GTSWSYSSNEIVAAAMVAAHVSELFRRSRPCLNALSALKRCKWDAEISTRASSLYHLIDLHGKTVSSIVNK
AEPLEAHLNLTAVKKDDQHHIEESNTSSSDYGNLEKKSKKNGFSRPLMKCAEQARRNGNVASTSGKATATL
QAEASDLANFLTMDRNGGYGGSQTLLRTVMSEKQELCFSVVSLLWHKLIASPETQMSAESTSAHQGWRKVA
DALCDVVSASPAKASTAIVLQAEKDLQPWIARDDEQGQKMWRVNQRIVKLIAELMRNHDSPEALIILASAS
DLLLRATDGMLVDGEACTLPQLELLEVTARAIHLIVEWGDPGVAVADGLSNLLKCRLSPTIRCLSHPSAHV
RALSMSVLRDILNSGPISSTKINQGEQRNGIQSPSYRCMAASMTNWQADVERCIEWEAHNRQATGMTLAFL
TAAANELGCPLPC

Fig. 11

MLSTSYALTAAPIPEGAAGPPDPFRPMQIANDNASAKRKRRPAGTPDPDAEVVSLSPRTLLESDRYVCEIC
NQGFQRDQNLQMHRRRHKVPWKLLKREAGEAARKRVFVCPEPTCLHHDPAHALGDLVGIKKHFRRKHSGHR
QWACSRCSKAYAVHSDYKAHLKTCGTRGHTCDCGRVFSRVESFIEHQDMCDASRPRGGTTSSSPGHGGGRV
VGASNPQHLLHAASLSRTASSASPSSGGELVGSPVAWPCGPATASPTAANVAAFQRLLDPTQSSSPPTPSD
RRGAGTQNLELQLMPPRGGGAAPPGTALTYRASPCSPSVLHAPRQLGADAVRLQLSIGCGGAPDDSSVESA
PAPAATLKEEAREQLRLATAEMASAEETRAQARRQVELAEQELAGARRVRQQAQLELGRAHALRDHAVRQI
DATLMEITCYGCRHNFRARAAAMNCEVASYVSSVLTEGGDAEVDNDGHHQLLHAGDLPRSHRAMMKMDLN

Fig. 12

MAAASSAPFFGLSDAQMQPMVPAQPPAPVAAAPAPKKKRNQPGNPNPDAEVIALSPRSLMATNRFVCEVCG
KGFQREQNLQLHRRGHNLPWKLKQKNPKDALRRRVYLCPEPTCVHHDPARALGDLTGIKKHYCRKHGEKKW
KCDKCAKRYAVQSDWKAHSKTCGTREYRCDCGTLFSRRDSFITHRAFCDALAQESARLPAIGASLYGGVGN
MGALNTLSGMPQQLPGGSFPDQSGHHSSASAMDIHNLGGGSNAGQFDQHLMPQSAGSSMFRSQAASSSPYY
LGAAAAQDFAEDDVHRSHGNQSSLLQGKSTAAFHGLMQLPDQHQGSASNGNNNLLNLGFYSGNGGGQDGRV
MFQNQFNSSAGNGNVNAENNGSLLGGGGGGFPSLFGSSESGGGLPQMSATALLQKAAQMGATTSSHNASAG
LMRGPGMRGGAGEGGSSSSASERQSFHDLIMNSLANGSGAPATTGGGTVAFGGGGFPIDDGKLSTRDFLGV
GPGGVVHAGMGPPRRHGGAAGLHIGSLDPAELK

Fig. 13

MPPNPTDPEQPEAAAAPAPPPKKKRNLPGTPDPDAEVIALSPGTLMATNRFVQEVCGKGFQRDQNEQLHRR
GHNLPWRLRQRGPGAAPPRRRVYVCPEPGCVHHAPARALGDLTGIKKHFCRKHGEKRWACPRCGKRYAVQA
DLKAHAKTCGTREYRCDCGTLFTRRDSFVTHRAFCGALVEETGRVLAVPAPPAPGPPDLDDVDENFDKDSE
KGEENVEDEEEKGEVNENSAVADVNEPQRVEAASEAPQRIPSPQQQRIPSPRRIPSPQRIRSPPSPVPQEQ
QQQPMVAVVPNLEGPKVAAEPIVVVKQEEDDKRDEDVCFQEADKYDDAELEGSSLPDTDTPMLPCFLPSPS
DAIGTDGSSTSCGTVSSASIPLRQQRRLAHLLGCLHRPRQAPLPRVDRCVILSVLIPPSFALRLVRPPLCS
RRQTRATLAALLHLQHHTCPRLHSCRRLLRLELRKQARLS

Fig. 14

MARSNWEADKMLDVYIYDYLVKRNLHNSAKAFMNEGKVATDPVAIDAPGGFLFEWWSIFWDIFDARTRDKP
HQGATAASIDLMKSREQQMRIQLLQQQNAHLQRRDPNHPAVNGAMNNSDVSAFLVSKMMEERTRNHGPMDS
EASQQLLEANKMALLKSAAANQTGPLQGSSVNMSALQQMQARNQQVDIKGDGAMPQRTMPTDPSALYAAGM
MQPKSGLVASGLNQGVGSVPLKGWPLTVPGIDQLRSNLGAQKQLMPSPNQFQLLSPQQQLIAQAQTQNDLA
RMGSPAPSGSPKIRPNEQEYLIKMKMAQMQQSGQRMMELQQQQHHLQQQQQQQQHQQQQQQQQQQQMQQN
TRKRKPTSSGAANSTGTGNTVGPSPPSTPSTHTPGGGIPVASNANIAQKNSMVCGTDGTSGFASSSNQMDN
LDSFVDFDDNVDSFLSNDDGDGRDIFAAMKKGPSEQESLKSLSLTEVGNNRTSNNKVVCCHFSTDGKLLAS
AGHEKKLFLWNMDNFSMDTKAEEHTNFITDIRFRPNSTQLATSSSDGTVRLWNAVERTGALQTFHGHTSHV
TSVDFHPKLTEVLCSCDDNRELRFWTVGQNAPSRVTRVKQGGTGRVRFQPRMGQLLAVAAGNTVNIIDIEK
DTSLHSQPKVHSGEVNCICWDESGEYLASASQDSVKVWSAASGACVHELRSHGNQYQSCIFHPRYPKVLIV
GGYQTMELWSLSDNQRNVVAAHEGLIAALAHSPSTGSVASASHDKSVKLWK

Fig. 15

MARSNWEADKMLDVYIYDYLVKRNLHNSAKAFMNEGKVATDPVAIDAPGGFLFEWWSIFWDIFDARTRDKP
PQGATAASIDLMKSREQQMRIQLLQQQNAHLQRRDPNHPAVNGAMNNSDVSAFLVSKMMEERTRNHGPMDS
EASQQLLEANKMALLKSAAANQTGPLQGSSVNMSALQQMQARNQQVDIKGDGAMPQRTMPTDPSALYAAGM
MQPKSGLVASGLNQGIGSVPLKGWPLTVPGIDQLRSNLGAQKQLMPSPNQFQLLSPQQQLIAQAQTQNDLA
RMGSPAPSGSPKIRPNEQEYLIKMKMAQMQQSGQRMMELQQQQHHLQQQQQQQQHQQQQQQQQQMQQNTRKR
KPTSSGAANSTGTGNTVGPSPPSTPSTHTPGGGIPVASNANIAQKNSMVCGTDGTSGFASSSNQMDNLDSF
VDFDDNVDSFLSNDDGDGRDIFAAMKKGPSEQESLKSLSLTEVGNNRTSNNKVVCCHFSTDGKLLASAGHE
KKLFLWNMDNFSMDTKAEEHTNFITDIRFRPNSTQLATSSSDGTVRLWNAVERTGALQTFHGHTSHVTSVD
FHPKLTEVLCSCDDNGELRFWTVGQNAPSRVTRVKQGGTGRVRFQPRMGQLLAVAAGNTVNIIDIEKDTGL
HSQPKVHPGEVNCICWDESGEYLASASQDSVKVWSAASGACVHELRSHGNQYQSCIFHPRYPKVLIVGGYQ
TMELWSLSDNQRNVVAAHEGLIAALAHSLTGSVASASHDSSVKLWK

Fig. 16

MSRALEPLVVGKVIGEVLDSFNPTVKMAATYNSNKQVFNGHEFFPSAIAAKPRVEVQGGDLRSFFTLVMTD
PDVPGPSDPYLREHLHWIVTDIPGTTDASFGKEVVNYESPKPNIGIHRFILVLFQQTHRGSVKNTPSSRDR
FRTREFAKDNELGLPVAAVYFNAQRETAARRR

Fig. 17

*QHHHLMQLTKKNPQAAAAAQLNLLQQQR IMHMQQQQQQQILKNL PLQRNQLQQQQQVQQQQQQQLQQQQQL
LRQQ*SLNMRTPGKSPPYEPGTCAKRLTHYMYHQQNRPQDNN IEYWRNFVNEYFAPTAKKRWCVSLYGSGRQ
TTGVFPQDVWHCEICNRKPGRGFETTVEVLPRLCQIKYASGTLEELLYIDMPRESKNVSGQIVLDYTKAIQ
ESVFDQLRVVREGHLRIIFNPDLKIASWEFCARRHEELIPRRSIIPQVSQLGAVVQKYQAAAQNPTSLSTQ
DMQNNCNSFVACARQLAKALEVPLVNDLGYTKRYVRCLQIAEVVNCMKDLIDHSRQTGSGPIDSLHKFPRR
TPSGINPLQSQQQQPEEHQSVPQSSNQSGQNSAPMAGVQVSASANADATSNNSINCAPSTSAPSPTVVGLL
QGSMDSRHNHPMCSANGQYNSGNNGAIPRVNSASSLQSNPSSPFPSQVPTSPNNNMMPTLQNANQLSSPPA
VSSNLPPIQPPSTRPQESEPSDAQSSVQRILQEMMSSQMNGVGHGGNDMKRPNGLTPGINGVNCLVGNAVT
NHSGMGGMGFGAMGGFGSTPAASGLRMAMTNNAMAMNGRMGMHHSAQDLSQLGQQHQHQHQHDIGNQLLGG
LGAANSFNNIQYDWKPSQ

Fig. 18

MSGAPRSNLGFVARDMNGSIPVSSANSSGPSIGVSSLVTDGNSSLSGGAQFQHSTSMNADSFMRLPASPMS
FSSNNISGSSVIDGSIMQQSPPQDQMQKRRSSTATSQPGIEAGAAFHAQKKPRVDI*RQDDILQQHLIQQVL
QGQSSLHLPGQHNPQLQALIRQQKLAHIQHLQQQQLSQQFPQIQQSQVGIPRQPQLRLPLAQPGMQ*LAGPV
RTPVESGLCSRRLMQYLFHKRHRPEDNPITYWRKLIDEYFAPRARERWCVSSYEKRGNSPVAIPQTSQDTW
RCDICNTHAGKGHEATYEILPRLCQIRFDQGVIDEYLFLDMPNEFRLPNGLLLLEHTKVVQKSIYDHLHVT
HEGQLRIIFTPELKIMSWEFCSRRHDEYITRRFLTPQVNHMLQVAQKYQAAANESGPAGVSNNDAQAICSM
FVSASRQLAKNLDHHSLNEHGLSKRYVRCLQISEVVNHMKDLIEFSHKNKLGPIEGLKNYPRQTGPKLTTQ
NMHDAKGVVKTEESTHVNNEGPDAGPAGSSPQNAGAQNNYQNMLRSPSPNQGLTHQEASQNAAALNNYQNM
LRSSSANQGLLQQEASQNVSGLNNYQNMLRSSSANQSILQQEASSIFKGPTGVHSSIQLEAARSFRAAQLG
PMSFQQAVPLYQQNRFGAVGVSPQYQQHVMQQLLQEANRSTNNRVLAQQQPLSTPNANGGLTITNSGASGDQ
AQHMNNNGAAKGVAAPMGMAGTSNLINSGSAGVVQRCSSFKSVTSNPAAAAAGNLLTPKAESMHEMDELDH
LITSELAESGLFMGEQQGGGGGYSWHM

Fig. 19

SDPLSFPSSSHVSLGNHISSDNL*QQQQQMDMPDLQQQQQQQQRQLPMSYNQQHLPMQRPQPQATVKLENGG
SMGGVKMEQQTGHPDQNGPAQMMHNSGNVKFEPQQLQALRGLGTVKMEQPNSDPSAFLQQQQQQQQQQHHHL
MQLTKQNPQAAAAAQLNLLQQQRIMHMQQQQQQHILKNMPLQRNQLQQQQQQQQQLQQQQHQQLLRQQ*SLN
MRTPGKSPPYEPGTCAKRLTHYMYHQQNRPQDNNVEYWRNFVNEYFAPTAKKRWCVSLYGSGRQTTGVFPQ
DVWHCEICNRKPGRGFETTVEVLPRLCQIKYASGTLEELLYIDMPRESKNVSGQIVLDYTKAIQESVFDQL
RVVREGHLRIIFNPDLKIASWEFCARRHEELIPRRSIIPQVSQLGAVVQKYQAAAQNPTSLSTQDLQNNCN
SFVACARQLAKALEVPLVNDLGYTKRYVRCLQIAEVVNCMKDLIDHSRQTGSGPIDSLHKFPRRTPSGINP
LQSQQQPPEEQQSVPQSSNQSGQNSAPMAGVQVSASANADATSNNSLNCAPSTSAPSPTVVGLLQGSMDSR
QDHPMCSANGQYNSGNNGAIPRVNSASSLQSNPSSPFPLQVPTSPNNNMMPTLQNANQLSSPPAVSPNLPP
MQPPSTRPQESEPSDAQSSVQRILQEMMSSQMNGVGHAGNDMKRPNGLTPGINGVNCLVGNAVTNHSGMGG
MGFGAMGGFGSNPAASGLRMAMTNNTMAMNGRMGMHHSAHDLSQLGQQHQHQHQHQHQHDIGNQLLGGL
RATNSFNNIQYDWKPSQ

Fig. 20

MKREYQDAGGSSAGGDMGMSKDKMMSAPPAQEDEDVDELLAALGYKVRSSDMADVAQKLEQLEMAMGMGGV
PAPDDGFTTHLATETVHYNPTDLSSWVESMLSELNAPPPLPPAPRLAPASASVTADGFFDIPPPSVDSSSS
TYALRPIPSPADLSADLSADSPRDPKRMRTGGGSTSSSSSSSSSLGGCVVEAAPPAAAEANAIALPVVVAD
TQEAGIRLVHALLACAEAVQQENFSAAEALVKQIPLLAASQGGAMRKVAAYFGEALARRVFRFRPQPDSSH
LDAAFADLLHAHFYESCPYLKFAHFTANQAILEAFAGCRRVHVVDFGIKQGMQWPALLQALALRPGGPPSF
RLTGVGPPQPDETDALQQVGWKLAQFAHTIGVDFQYRGLVAATLADLEPFMLQPEAEDGPNEEPEVIAVNS
IFEMHRLLAQPGALEKVLGTVRAVRPRIVTVVEQEANHNAGSFLDRFTESLHYYSTMFDSLEGAGSGPSEI
SSGPAAAAAAPGTDQVMSEVYLGRQICNVVACEGAERTERHETLGHWRGRLGHAGFETVHLGSNAYKQAST
LLALFAGGDGYKVDEKEGCLTLGWHTRPLIATSAWRMAAAP

```
                        SEQUENCE LISTING

<160> NUMBER OF SEQ ID NOS: 40

<210> SEQ ID NO 1
<211> LENGTH: 808
<212> TYPE: DNA
<213> ORGANISM: Lolium perenne

<400> SEQUENCE: 1
gcagaagtct ctgtcgtccg cagccgcctc gctaggattt cgtttgtccc caaatcgccc      60
ccaaatccgc cgccgatccc caacctcaac ccaccaccca tggcggccga ggacaagaag     120
atcacgctca agtcctcgga cggcgagcag ttcgaggtgg acgaggcggt ggcgatggag     180
tcgcagacga tccgccacat gatcgaggat gactgcgcca caacgggat cccgctcccc      240 aacgtcaacg ccaagatcct ctccaaggtc gtcgagtact gcagcaagca cgtccaggcg     300
gccgacggcg ccgcggcggc ggacggagct cccgccccgc ccccgccga ggacctcaag      360 aactgggacg ccgagttcgt caaggtcgac caggccacgc tcttcgacct catcctcgcc     420
gccaactacc tcaacatcaa gggcctgctc gacctcacct gccagaccgt cgccgacatg     480
atcaagggca agacacccga ggagatccgc aagacgttca acatcaagaa cgacttcacc     540
gccgaggagg aggaggagat ccgcaggag aaccagtggg ccttcgagta aatccacatc      600
gccccggtga agctgtaaat ttacatatct aattcactag ttagtcggat cgaaagagtt     660
gtaaagtgac atcaattttg atcgttggtg gttgatagtg taatctttct gtcagcactt     720
cttcattcgt tttggtttgt tttaatttta tgttgcctat tcttgattct tttagaatgg     780
cacaccttaa tatcatttaa aaaaaaaa                                         808

<210> SEQ ID NO 2
<211> LENGTH: 831
<212> TYPE: DNA
<213> ORGANISM: Lolium perenne

<400> SEQUENCE: 2
gtcctcttcc gccgccccc tcgtttagca gctagggttt cctcccatcc caaatccccc      60
gatttcccga tctccaaccc cacctcgccc acccatggcg gccgccgacg actccaagaa     120
gatgatcacc ctcaagtcgt ccgacgggga ggtgttcgag gtggaggagg cggtggcgat     180
ggagtcgcag accatccgcc acatgatcga ggacgactgc gccgacaacg ggatcccgct     240
ccccaacgtc aactccaaga tcctctccaa ggtcatcgag tactgcaaca agcacgtcca     300
ggccgccaag cccgccgccg acgccgccgc cgccgacagc tcctccgccg ccgccccgcc     360
```

-continued

```
cgaggacctc aagaactggg acgccgagtt cgtcaaggtc gaccaggcca ccctcttcga    420
cctcatcctc gccgccaact acctcaacat caagggcctg ctcgacctca cctgccagac    480
cgtcgccgac atgatcaagg gcaagacacc cgaggagatc cgcaagacct tcaacatcaa    540
gaacgacttc accgccgagg aggaggagga gatccgcagg agaaccagt gggcgttcga    600 gtagagcctc acaaccctgc cgcgccgcgt tgatgatgcc tagctaaaac tcgcaattta    660
cgcatctcga cgctgctact accttttatg taataattat cttcttgagt cgaggtccgg    720
tttatgaaca tctatctatc tatcttcggt ggtctgaaca aaaactatat atccttgttc    780
agtgggtttt atctatgaac atctatcgtc agtggttgtt taaaaaaaaa a            831
```

<210> SEQ ID NO 3
<211> LENGTH: 773
<212> TYPE: DNA
<213> ORGANISM: Lolium perenne

<400> SEQUENCE: 3

```
ctccgacggc gaggagtttg aggtggagga ggtgctggtg ctggagtcgc agaccatcaa     60
gcacatgatc gaggacgagt gcgacggcgt catcccgctc cccaacgtca gcgccaagat    120
cctctccaag gtcatcgagt actgcaggaa gcacgtccag acgcgcgccg ccctcgcccc    180
cgacggcgac atgagcacca acgccgccgg caccgagctc aagaccttcg acgaggactt    240
cgtcaaggtc gaccaggcca ccctcttcga cctcatcctg gctgcaaact acctggacat    300
caaggggctg ctggacctga cctgccagac ggtggctgac atgatcaagg gtaagacccc    360
agaggagatc cgcgcgacct tcaacatcaa gaacgacttc accccagagg aagaggagga    420
agtgcgcaag gagaacgcgt gggccttcga gtgaaggtcg ccgccctgac aagtaacgcg    480
aataaccagc aagaagaggt aacgatggcg ctggtagtgc ctgggagcag ctgttaaccg    540
tctgtggttc gaaaaactat gctagggtga agttgtaagt aggttctggt tccggtggat    600
cgggaggcct taccatttgc tgagctgact ccgttctttt ttggtggtga tatttggtgc    660
actcttgaac ctggttatga ggtgatgctg gttgctggtt attctgcact aatgctagtt    720
ggatcttatg catgactctc ttgtgctgag cttcatttgt tttaaaaaaa aaa           773
```

<210> SEQ ID NO 4
<211> LENGTH: 2404
<212> TYPE: DNA
<213> ORGANISM: Festuca arundinacea

<400> SEQUENCE: 4

```
gcggaggccg tggtgactac tcagatcatg acaacaaaag tggccatgtt aaacttttg      60 ttggatcagt tccgagaaca gcaagtgaag acgatgttcg acctttattt gagaatcatg    120
gagatgttct tgaagttgct atgatcaggg acaggaaaac tggtgaacaa caaggctgtt    180
gctttgttaa atatgcgact tccgaagagg ctgagagagc cataagagct cttcataacc    240
agtggactat acctggggcg atgggccctg ttcaggttag atacgccgac ggtgaaaagg    300
agcgtcatgg gtccattgag cacaaattat tgtcgcatc actgaataag caggcaactg    360
caaaggagat tgaagagatt tttgctccctt ttggtcacgt ggaagatgtt tacattatga    420 agatggcat gaagcagagc cgaggttgtg gctttgtcaa attctcatca aaagaacctg    480
cacttgcggc catgaattct cttagtggga cttacataat gagggggtgt gaacaaccat    540
taatagttcg atttgctgat cctaagcggc ctagacctgg agaatcaagg tggttaagaa    600
```

```
tgcatatttg ttttgcttat attccaactc tgcactattt cccgttgctg ctgtctgaat      660
tatcttgttt ggttaggggt ggccctgcat ttggaggtcc tggtgtcagt cctcgatctg      720
atgcagcact tgttatcagg ccgactgcca atcttgatga gcctagaggt cgacatatgc      780
ctcgtgacgc ttggcgccct tcaagcccaa gttcagtggc acctcatcag tttaataact      840
atgggtcgga caatcctatg ggcctaatgg gtggcactgg tacatcagca acagataatg      900
gtgcttttcg gcctcagatg tttcctggga atggtcagac agctgtgccg acgtcatctc      960
atatgggcat aaacacttct tcggtacaag gccatcatct aggggggcag cagatcccgc     1020
ccttgcaaaa gccacctgga ccaccacata atttctcttt acaattgcag aatcagcagg     1080
ggcagcattc cttggggcct ggtttgtttg ccagaatgt accatctatg caattacctg      1140
gccagcttcc cacatcacag ccattgacgc agcagaatgc ttctgcaggc gctctacagg     1200
tgcctccagc catacagtcc aatcccatgc aatcggttcc cggacaacag caacttccgt     1260
ccaatgtggc agcacaaatg atgcaacaac caatccagca gataccatca caagcgccac     1320
agttgctact ccaacagcag gcagctatgc agtccagtta tcaatcttcg cagcaggcaa     1380
tttttcagct tcagcaacag ctgcagctaa tgcaacagca gcagcaacag cagcagcaac     1440
ctaacctcaa tcagcagcca catcacagga tttctaagca acagggacag ccaaatcaat     1500
ccagtacccc tggtgctcca gctgccatga tgccgtcaaa cattaatgca attccacagc     1560
aggtcaattc acctgtagtt tctttaactt gcaattggac ggaacatacc tcccccgaag     1620
gttttaaata ctactacaat agtattactc gagagagtaa gtgggagaag cctgaagagt     1680
atgtactgta cgagcaacag caacagcagc agcatcagaa acttattta cttcaacagc      1740 accaacaaaa gcttgttgcg cagcaacttc agtcacctcc tcaggctcaa acaattcaat     1800
ctatgcaatc tatccaacaa catcctcagt cacatcaagg acataaccag atgcagatga     1860
aacatcagga attaaactat aatcagttgc aggcaactgg caatattgat cccaatagga     1920
tccagcaggg aattcaagct gctcaagagc gttcatggaa aagttgagac tgctggtgaa     1980
tacatgttga ggtgtcagtc aaggctcaga aatgagctcc agccaagcct gccgattcca     2040
tgcgtgagag tgatggctct tgcggtcatt gtaactggat ttggcttaga tcgcagccta     2100
gatcgtagat cccatctgtg taaaatattt gcagtctagg ccttgtatca ctgtaacatt     2160
gttgattaga atatcgctct ttgtatctgt ttcctcgctt ttctttatgg caggatgtgc     2220
tgtctcattt acatcaattt ttcctccacc tgttatgttg gagctgcgct cctgaattgc     2280
tggctcgttc ttttttttctt cggaacactt gagttctttg aacagccaaa tagtgcttgg     2340
agaagggaac cttttgagct ccaacggctg gttaatctca gaatcagttt catgaaaaaa     2400
aaaa                                                                  2404
```

<210> SEQ ID NO 5  
<211> LENGTH: 2135  
<212> TYPE: DNA  
<213> ORGANISM: Lolium perenne

<400> SEQUENCE: 5

```
cggaggccgt ggtgactact cagatcatga caacaaaagt ggccatgtta aacttttgt       60 tggatcagtt ccgagaacag caagtgaaga cgatgttcga cctttatttg agaatcatgg      120
agatgttctt gaagttgcta tgatcaggga caggaaaact ggtgaacaac aaggctgttg      180
ctttgttaaa tatgcgactt ccgaagaggc tgagagagcc ataagagctc ttcataacca      240
gtggactata cctggggcga tgggccctgt tcaggttaga tacgccgacg gtgaaaagga      300
```

```
gcgtcatggg tccattgagc acaaattatt tgtcgcatca ctgaataagc aggcaactgc      360
aaaggagatt gaagagattt ttgctccttt tggtcacgtg gaagatgttt acattatgaa      420
agatggcatg aagcagagcc gaggttgtgg ctttgtcaaa ttctcatcaa agaacctgc       480 acttgcggcc atgaattctc ttagtgggac ttacataatg aggcggccta gacctggaga      540
atcaaggggt ggccctgcat ttggaggtcc cggtgtcagt cctcgatctg atgcagcact      600
tgttatcagg ccgactgcca atcttgatga gcctagaggt cgacatatgc tcgtgacgc       660 ttggcgccct tcaagcccaa gctcagtggc atctcatcag tttaataact atgggtcgga      720
caatcctatg ggcataatgg gtggcactgg tacatcagca gcagataatg gtgcttttcg      780
gcctcagatg tttcctggga atggtcagac agctgtgccg acgtcatctc atatgggcat      840
aaacacttca ttacaagggc atcatctagg ggggcagcag atcccgccct tgcaaaagcc      900
acctggacca ccacacaatt tctctttaca attgcagaat cagcaggggc agcattcctt      960
ggtgcctggt ttgtttggcc agaatgtacc atctatgcaa ttacctggcc agcttcccac     1020
atcacagcca ttgacgcagc agaatgcttc tgcaggcgct ctacaagcgc tccagccat     1080 acagtccaat cccatgcaat cagttcctgg acaacagcaa cttccgtcca atgtggcacc     1140
acaaatgatg caacaaccaa tccagcagat accatcacaa gcaccacagt tgctactcca     1200
acagcaggca gctatgcagt ccagttatca atcttcgcag caggcgattt ttcagcttca     1260
gcaacagctg cagctaatgc aacagcagca gcaacagcag cagcaaccta acctcaatca     1320
gcagcaacct aacctcaatc agcagcaaca tacacagatt tctaagcaac agggacagcc     1380
aaatcaatcc agtacacctg gtgctccagc tgccatgatg ccgtcaaaca ttaatgcaat     1440
tccacagcag gtcaattcac ctgcagtttc tttaacttgc aattggacgg aacatacctc     1500
ccccgaaggt tttaaatact actacaatag tattactcga gagagtaagt gggagaagcc     1560
tgaagagtat gtactgtacg agcaacagca acagcagcag cagcagcaga aacttatttt     1620
acttcaacag caccaacaaa agcttgttgc gcagcaactt cagtcacctc ctcaggctca     1680
aacaattcaa tctatgcaat ctatccaaca acatcctcag tcacatcaag acataaccaa     1740
gatgcagatg aaacatcagg aattaaacta taatcagttg caggcaactg caatattga      1800 tcccaatagg atccagcagg gaattcaagc tgctcaagag cgttcatgga aaagttgaga     1860
ctgctggtga atacatgttg aggtgtcagt caaggctcag aaatgagctc cagccaagcc     1920
tgccgattcc atgggtgaga gtgatggctc ttgcggtcat tgtaactgga tttagcttag     1980
atcgcagcct agatcgtaga tcccatctgt gtaaaatatt tgcagtttag gccttgtatc     2040
actgtaacat tgctgattag aatatcattc cggtatctgt ttcctcgctt ttctttatgg     2100
caggatgtgc tgtttcattt cccttaaaaa aaaa                                 2135

<210> SEQ ID NO 6
<211> LENGTH: 842
<212> TYPE: DNA
<213> ORGANISM: Festuca arundinacea

<400> SEQUENCE: 6
cattcatcca ggtagctcct gctccagatc aatatactct agctaactag ctcaactgtg       60
cctggccatc gtcaacctct agcttcaaca tacgagatgg ctgggaggga tagggacccg      120
ttggtggttg aagggttgt gggggacgtg ctggaccccct tcgtccgcac cactaacctc      180
agggtgacat tcggaaaccg ggccgtgtcc aacggctgcg agctcaagcc ctccatggtc      240
```

```
acccaccagc ccagggtcga ggtcggcggc aatgagatga ggaccttcta cacactcgtg      300
atggtagacc ccgacgcgcc aagtccaagc gatcccaacc tcagagaata cctccattgg      360
ttggtgacag atattcctgg aactactggt gcttccttcg ggcaggaggt gatgtgctac      420
gagagccctc gccccaacat gggaatccac cgcttcgtgc tcgtactctt ccagcagctg      480
ggccggcaga cggtgtacgc gcccgggtgg cgccagaact tcaataccag ggacttcgcc      540
gagctctaca acctcggccc ggccgtcgcc gccgtctact tcaactgcca gcgcgaggcc      600
ggctctggcg gcaggaggat gtataattga caccgccacg ccaagactca gacctacaca      660
agatcgatga tccattcaca gcgtgcctag ctaagcttaa ctaataatta ctatatacta      720
catatggtgt gtcataagaa gctagctagc cacgcaattg atcaagcatt attatacgca      780
tatagatatt gtgtacaacc tatatcataa caattattag ctacatatac ataaaaaaaa      840
aa                                                                     842
```

```
<210> SEQ ID NO 7
<211> LENGTH: 825
<212> TYPE: DNA
<213> ORGANISM: Lolium perenne

<400> SEQUENCE: 7
gcaccaccag cacgcgcgcg cgcgcgagta gtagtagtag ccctccagag agtccaccag       60
acagagagta aaatggacgg cgtcttggcc ggccggccga cggatagatt cccccccactc     120 ggagcagcca tcggatcaga ccggtcagga cagccaggct gacgcactca gtacacctcg     180
gcagccagag ctgctcgtga tccagcagct agctagctag ctagcttggt cgagactcga     240
tcgagagaga tctcctctcc tataagtacg ccggctcgtc gtggtgcaac agcgacggga     300
gacagaaaga gcttcagctt cagcttgcaa ctgcaaccac acgcgctcag ctaagctcac     360
acacatcgat ctagccggcc ggcgatcgga gacgatggtg ggcgtgcagc gcgccgaccc     420
gctggtggtg gggcgcgtga tcggcgacgt ggtggacccg ttcgtgcgcc gggtgccgct     480
gcgggtcggc tacgcgtcca gggacgtggc caacggctgc gagctccgcc cgtccgccat     540
cgccgaccag ccgcgcgtcg aggtcggcgg cccggacatg cgcaccttct acacgctggt     600
gatggtggat ccggatgctc ccagcccgag cgatcccagc ctcagggagt acttgcactg     660
gtgagagccg agcaccaaca ccaacatcga aagatcaatc tctctctcct acctggcctg     720
gaaatatccc cctcccatgc ccctaccaat ccaaattcag atatttgtgt acagttagct     780
ggggaacagg gccaaatagc atctttccgc aaagcaaaaa aaaaa                     825
```

```
<210> SEQ ID NO 8
<211> LENGTH: 1473
<212> TYPE: DNA
<213> ORGANISM: Lolium perenne

<400> SEQUENCE: 8
cgaggccttc gccggctgcc gccgcgtcca cgtcgtcgac ttcgggatca agcagggcat       60
gcagtggccc gccctcctcc aggccctggc cctccgcccc ggcggcccgc cctcgttccg      120
cctcacgggc gtcggccccc gcagcccga cgagaccgac gcgctgcagc aggtcgggtg      180
gaagctggcc cagttcgcgc acaccatcgg cgtcgacttc cagtaccgcg gcctcgtcgc      240
cgccacgctc gccgacctcg agcccttcat gctgcagccg gaggccgacg acgggcccaa      300
cgaggagccc gaggtcatcg ccgtcaactc cgtcttcgag atgcaccgcc tcctcgcgca      360
gcccggcgcc ctggagaaag tcctgggcac cgtgcgggcc gtgcggccga ggatcgtcac      420
```

-continued

```
cgtcgtggag caggaggcca accacaacac cggctccttc ctggaccgct tcaccgagtc    480
cctgcactac tactccacca tgttcgactc cctggagggc gccggctccg ccccgtccga    540
aatctcatct gggccttccg ccgccgccgc caacgccgcc gctcctggca cggaccaggt    600
catgtccgag gtgtacctcg gccggcagat ctgcaatgtc gtggcctgcg agggcgccga    660
gcgcacggag cgccacgaga cgctgggcca gtggcgcggc cgcctcggcc acgccggctt    720
cgagaccgtc cacctcggct ccaacgccta caagcaggcc agcacgctgc tcgcgctctt    780
cgccggcggc gacggctaca aggtggacga aaggaaggc tgcctcacgc tcggctggca    840
cacgcgcccg ctcatcgcca cctccgcgtg gcgcatggcc gccgccgccg cgccatgatc    900
gcaagttttg aacgctgtaa gtacaccaca ccccgagca cggaggagca caaccccccg    960
ccccttggct caccggcgca cttgaatgaa agctaaaacg tcgacgaacg ctggattgca   1020
gcgaccaacg atcggagtta cggatctcgc tggcgtgaag agatggacac cggacggact   1080
cccggcgacc accaccacca ccatagcctg taattcgttc ttgttctcga ttccccactt   1140
gatccgtgaa ctcctagcaa gctctattat taagttttaa aatgtctatt attgttctgt   1200
gtaattcctc caatcgctca tatttaaata aggacgggac ggatttcggt actagctctg   1260
atgatgagaa ttttgtatgc aaagcaatct aaaactgagc tttgttctgg tctttgatca   1320
ccagttatga accttagagc aatgcgttct attctcactg ctcttagtat gaacatgagg   1380
ttcttctact cttgatcagt tgtaagcaat taagtgctga gctcttgact gttcttaatt   1440
atgaacatga tgttcttctc ctcaaaaaaa aaa                                1473
```

<210> SEQ ID NO 9
<211> LENGTH: 3913
<212> TYPE: DNA
<213> ORGANISM: Lolium perenne

<400> SEQUENCE: 9

```
gctcgctcca agtttctctc tcctcgcctc cggctccgtc tacccgctcg ccgccgcgcg     60
aatcccgtcg ccgccgccgc tgattcgccg ccggagcccc ggagtagagc gcgccctgtc    120
tagtttcttg agcaggatct taaactacta gtatgtctg tctcaaatgg aagtggatc     180 gacgggctcc agttctcttc actattctgg ccccgccac acgatgcaca gcagaaacag    240
gcacaaactt tggcctacgt tgagtacttt ggtcagttta catctgacag tgagcaattc    300
ccggaggatg ttgctcagct catccaaagt tactatccat cgaaagaaaa acgcttggta    360
gatgaagtat tagcaaccct tgttctccat caccccgagc atggtcatgc agttgtacat    420
ccaattcttt cacgcatcat agatgggtcc ctgagttatg atagacatgg ttccccattc    480 aattcttttca tctctttatt tacccaaact gctgagaaag agtattcaga gcagtgggct    540
ttggcgtgtg gagaaattct tagagttctt actcactaca ataggccaat cttcaaagtt    600
gcagaatgta acgacacctc cgaccaggcc acaacaagtt attccttaca tgacaaagct    660
aatagctctc cagaaaatga acctgaacgg aagccattga ggccattatc tccttggatc    720
acagacattt tgttaaatgc acctttgggc attagaagtg actatttag atggtgtggt    780 ggagtcatgg gaaaatatgc agctggtgga gaactgaagc ctccaacaac tgcttacagc    840
cggggagctg gtaagcatcc acaacttatg ccatccaccc ctagatgggc tgttgccaat    900
ggagctggag tcatcttaag tgtctgtgac gaggaagtag ctcgttacga gacagcaaac    960
ttaaccgcag cagctgttcc tgcgcttctg ctacctccac cgacaacgcc cttggatgag   1020
```

```
catttggtgg cagggttgcc ccctcttgaa ccatacgctc gcttgtttca cagatactac    1080
gcaattgcta ctccaagtgc tacacaaagg ttgctctttg gtcttcttga agcaccgcct    1140
tcatgggctc cagatgcact tgatgcagca gtacagcttg ttgaactcct tcgagcagcc    1200
gaagattatg ctactggcat gcggcttccg aaaaattggc tgcatcttca tttcttgcgt    1260
gcaatcggaa ctgcaatgtc aatgagagct ggtatggctg ctgatacggc cgctgccttg    1320
ctatttcgta tactatccca accaacgttg ctttttcctc cactaagaca tgccaagga    1380 gttgtgcagc atgaaccact aggtggctat gtatcatcat acaaaagaca gctggagatt    1440
cctgcatctg aaaccactat tgatgctact gcacaaggca ttgcttcctt gctgtgcgct    1500
catggtcctg atgttgagtg gagaatatgt accatctggg aagctgccta tggtttgtta    1560
cctctgaatt catcagcagt cgatttgcct gaaattgttg tagctgctcc gcttcagcca    1620
cctactttat catggagcct atatttgcca ctgttgaaag tatttgagta tctacctcgt    1680
ggaagtccat ctgaagcatg ccttatgaga atatttgtgg caactgttga agctatactc    1740
aggagaactt tcccttcgga aaccgaacca tccaaaaaac caagaagtcc atctaagagc    1800
cttgctgttg ctgaactccg tacgatgata cattcactct tgttgaatc atgtgcctca    1860 atgaaccttg cttcgcggtt attgtttgta gtattgactg tctcagtcag tcatcaagct    1920
ctgccggggg gcagcaaaag acctacaggc agtgagaacc attcttctga ggagtccact    1980
gaggactcaa aattaaccaa tggaagaaac agatgcaaga agaaacaagg gcctgttggt    2040
acctttgact cgtatgtgct ggctgctgtt tgtgctttat cttgtgagct tcagctgttc    2100
cctatacttt gcaagaatgt tacgaagaca aacataaaag actctataaa gattaccatg    2160
cctggaaaaa ccaatgggat cagtaatgag ctacacaata gcgttaactc agcgattctc    2220
catactcgta gaattcttgg catcctggaa gctcttttct ccttgaagcc atcatcagtt    2280
ggtacctcct ggagctatag ttcaaatgag atagttgcag cagcaatggt tgctgctcat    2340
gtttctgagt tattccgtag gtcgaggcca tgcctaaatg cactatctgc actgaagcga    2400
tgtaagtggg atgctgagat ttctaccagg gcatcatcgc tttaccatct gatcgacttg    2460
catggtaaaa ctgtgtcatc catcgtgaac aaagctgagc ctttggaagc tcacctgaac    2520
cttacagcag taaagaaaga tgatcaacac cacattgagg aaagcaatac cagctcatcg    2580
gattatggga acttggagaa gagagtaag aaaaatggtt tttcaagacc actcatgaaa    2640
tgtgcagaac aggctaggag aaatggtaac gttgcaagta catcggggaa agctactgca    2700
actttacagg cggaagcatc tgatttggca aacttcctta ccatggacag gaacgggggt    2760
tatggaggtt ctcaaactct cctaagaact gtaatgtcag aaaagcagga actatgcttt    2820
tctgttgtct cgttgctgtg gcataagctt attgcatctc ccgaaacaca gatgtctgca    2880
gagagtacat cagctcatca gggttggaga aaggttgcag atgcgctttg tgatgttgtt    2940
tcagcttcac cggccaaggc ttcaactgct attgtcctgc aggctgagaa ggacttgcag    3000
ccctggattg ctcgagatga tgagcaaggt cagaagatgt ggagagtcaa ccagcgaata    3060
gtgaaactga tagctgagct tatgaggaac catgatagcc cagaagcact gataattctt    3120
gcgagcgctt cagaccttct gctccgtgcc acggatggga tgcttgttga tggtgaagct    3180
tgtaccttgc ctcaattgga gcttctgaa gtaaccgcca gagccattca tctcatcgtt    3240
gaatggggag atccaggtgt agcagttgct gatggcctct cgaatctgct gaagtgccgg    3300
ctatcaccta ccatccgatg cctttcccac cctagtgcac atgtacgggc gctcagcatg    3360
tccgtccttc gcgacatctt gaacagtgga ccaataagtt ccaccaagat aattcaagga    3420
```

-continued

```
gagcagcgga acggcatcca aagcccaagt taccggtgcg cggcagcaag tatgaccaac      3480
tggcaagcgg acgtcgagag atgcatagag tgggaagccc acaaccgtca ggccaccggg      3540
atgacgcttg cctttctcac tgcagcggct aacgaactcg gatgccccct tccttgctga      3600
cacagccata tttgaagctg acatcggcga cacttgacag ttagcgcgag cagttgctgc      3660
atggtcagcg agcaggatgg ctaatcccctt gctcaaggat gacttccagc tctgccccca      3720
ttatgtgatt taaaactgat gtatattagt tgacccagtc atacggagct tgctcccact      3780
gtgtgattta acttttaatc tgacattaga tgttcaagca tattgaactg cttgtgctgt      3840
aacttgtatt tctgtagccg aaagatgtac actatggtaa atgaagacat atcattttc       3900 gtcaaaaaaa aaa                                                         3913
```

<210> SEQ ID NO 10
<211> LENGTH: 3980
<212> TYPE: DNA
<213> ORGANISM: Festuca arundinacea

<400> SEQUENCE: 10

```
ggaaatcttt ttctcgcctc tcctcgcccc tcgcagtttc tctctcctca ccttcgcctc       60
cgcctccgcc tccgtctacc cctcgccgcc gcgcaattcc catcaccgcc gccgctgatt      120
cgccgccgga gctccggatt agagcgcgcc ccgtctagtt tcttgagcag atcctaaac       180 tactaagtat gtctgcgtca atgggaagt ggattgatgg gctccagttc tcttcactat       240
tctggccccc gccacacgat gcacagcaga aacaggcaca aactttggcc tacgttgagt      300
actttggtca gttcacatct gacagtgagc aattcccgga ggatgtagct cagctcatcc      360
aaagttgcta tccatcgaaa gaaaaacgct tggtagatga agtattagca accttttgttc     420 tccatcaccc cgagcatggt catgcagttg tacatccaat tctttcacgc atcatagatg      480
ggtcactgag ttatgataga catggttccc cattcaattc tttcatctct ttatttaccc      540
aaactgctga gaaagagtat tcagagcagt gggctttggc ctgtggagaa attcttagag      600
ttcttactca ctacaatagg ccaatcttca aagttgcaga atgtaacgac acctctgacc      660
aggccacaac aagttattcc ttacaggaga aagctaatag ctctccagaa atgaacctg       720 aacggaagcc attgaggcca ttatctcctt ggatcacaga cattttgtta aatgcacctt      780
tgggcattag aagtgactat tttagatggt gtggtggagt catgggaaaa tacgcagctg      840
gtggagaact gaagcctcca acaactgctt acagccgggg agctggtaag catccacaac      900
ttatgccatc cacccctaga tgggctgttg ccaatggagc tggagtcatc ttaagtgtgt      960
gtgacgagga agtcgctcgt tacgagacag caaacttaac cgcagcagct gttcctgcgc     1020
ttctgctacc tccaccgaca acgcccttgg atgagcattt ggtggcaggg ctgcccctc      1080 ttgaaccata cgctcgcttg tttcacagat actacgcaat tgctactcca agtgctacac     1140
aaaggttgct ttttggtctt cttgaagcac caccttcatg ggctccagat gcacttgatg     1200
cagcagtaca gcttgttgaa ctccttcgag cagccgaaga ttatgctact ggcatgcggc     1260
ttccgaaaaa ttggctgcat cttcattct tgcgtgcaat tggaactgca atgtctatga      1320
gagctggtat ggctgctgat acggccgctg ccttgctatt tcgtatacta tcccaaccaa     1380
cgttgctttt tcctccacta agacacgccg aaggagttgt gcagcatgaa ccactgggtg     1440
gctatgtatc atcatacaaa agacagctgg agattcctgc atctgaaacc actattgacg     1500
ctactgcaca aggcattgct tccttgctgt gcgctcatgg tcctgatgtt gagtggagaa     1560
```

```
tatgtaccat ctgggaagct gcctatggtt tgttacctct gaattcatca gcagtcgatt      1620
tgcctgaaat tgttgtagct gctccgcttc agccacctac tttatcatgg agcctatact      1680
tgccactgtt gaaagtattt gagtatctac ctcgtggaag tccatctgaa gcatgcctta      1740
tgagaatatt tgtggcaacg gttgaagcta tactcagaag aactttccct tcggaaacct      1800
ctgaaccatc caaaaaacca agaagtccat ctaagagcct tgctgttgct gaactccgta      1860
cgatgataca ttcactcttt gttgaatcat gtgcgtcaat gaaccttgct tcccggttgt      1920
tgtttgtagt attaactgtc tcagtcagtc atcaagctct gccgggaggc agcaaaagac      1980
ctacaggcag tgataaccat tcttctgagg agtccactga ggactcaaaa ttaaccaatg      2040
gaagaaacag atgcaagaag aaacaagggc ctgtcggtac ctttgactcg tatgtgctgg      2100
ctgctgtttg tgctttatct tgtgagcttc agctgttccc tatactttgc aagaatgtta      2160
caaagtcaaa cataaaagac tctataaaga ttaccatgcc tggaaaaacc aatgggatca      2220
gtaatgagct acacaatagt gttaactcag cggttctcca tacccgtaga attcttggca      2280
tcctggaagc tcttttctcc ttgaagccat catcagttgg tacctcctgg agctatagtt      2340
caaatgagat agttgcagca gcaatggttg ctgctcatgt ttctgagtta tttcgtcggt      2400
cgaggccatg cctaaatgca ctatctgcac tgaagcgatg taagtgggat gctgagattt      2460
ccaccagggc atcatcgctt taccatctga tcgacttgca tggtaaaact gtgtcatcca      2520
tcgtgaacaa agctgagcct ttggaagctc acctgaacct tacagcagta aagaaagatg      2580
atcaacacca cattgaggaa agcaatacca gctcatcgga ttatggcaac ttggaaaaga      2640
agagtaagaa aaatggtttt tcaagaccac tcatgaaatg tgcagaacag gctaggcgaa      2700
atggtaacgt tgcaagtaca tcggggaaag ctactgcaac tttacaggcg gaagcatctg      2760
atttggcaaa cttccttacc atggacagga atgggggtta tggaggttct caaactcttc      2820
taagaactgt aatgtcagaa aagcaggaac tatgcttctc tgttgtctcg ttgctgtggc      2880
ataagcttat tgcatctccc gaaacacaga tgtctgcaga gagtacatca gctcatcagg      2940
gttggagaaa ggttgcagat gcgctttgtg atgttgtttc agcttcaccg gccaaggctt      3000
caactgctat tgtcctgcag gctgagaagg acttgcagcc ctggattgct cgagatgacg      3060
agcaaggtca gaagatgtgg agagtcaacc agcgaatagt gaaactgata gctgagctta      3120
tgaggaacca tgatagccca gaagcactga taattcttgc gagcgcttca gatcttctgc      3180
tccgtgccac ggatgggatg cttgttgatg gtgaagcttg taccttgcct caattggagc      3240
ttctggaagt aaccgccaga gccattcatc tcatcgttga atggggagat ccaggtgtag      3300
cagttgccga tggcctctcg aatctgctga agtgccgtct atcacctacc atccgatgcc      3360
tttcccaccc tagcgcacat gtacgggcgc tcagcatgtc cgtccttcgc gacatcttga      3420
acagtggacc aataagttcc accaagataa atcaaggaga gcagcggaac ggcatccaaa      3480
gcccaagtta ccggtgcatg gcagcaagca tgaccaactg gcaggcggac gttgagagat      3540
gcatagagtg ggaagcgcac aaccgtcagg ccaccggcat gacgcttgcc tttctcactg      3600
cagcggctaa tgaactcgga tgccccttc cttgctgaca tggccatatt taagctgaca      3660
tcggcgacac ttgacagttg gcgcatgcag ttggtgcatg gtcagcgagc aggatggcta      3720
atcccttgct caaggatgac ttcccagtct gccccatta ttatgtcatt taaaactgat      3780
gtatattagt tgtcccagtc atacggagct ttaatctgtg acgttagatg ttcaagcata      3840
ttgaactact tgtgctgtaa cttgtcttcc tgtagccgaa cgatgtacac tatggtaaat      3900
gaagacatgt cattttttcgt catgtaagat acatgcttat ctgcagagct tcaacctgaa      3960
```

```
cctgcctgtt aaaaaaaaaa                                        3980

<210> SEQ ID NO 11
<211> LENGTH: 1852
<212> TYPE: DNA
<213> ORGANISM: Festuca arundinacea

<400> SEQUENCE: 11
atagaaacct ccttcccgct agcttatata gagaccagtc gattcccgtg atccattccc     60
atggcttaga gtggtgatcg agcacgaaca agaacgtaga caagcaaact caccagagac    120
cgaggcttaa tttcctgcct tctgttcgat taggttgcca ccatgttgag tacgtcttac    180
gcgctgacgg ccgcgccgat tccggagggg gccgctgggc cacctgatcc ttttcggccg    240
atgcagatcg ccaacgacaa cgcctccgcg aagaggaagc ggcggccagc cggcactcct    300
gacccggatg cggaggtggt gtcgctgtcg ccgcggacgc tgctggagtc tgaccggtac    360
gtgtgcgaga tctgcaacca ggggttccag cgggaccaga acctgcagat gcaccggcgg    420
cggcacaagg tgccgtggaa gctgctgaag cgggaggccg cgaggcagc gcggaagcgg     480 gtgttcgtgt gccccgagcc gacgtgcctc caccacgacc ctgcgcacgc cctcggcgac    540
ctcgtcggca tcaagaagca cttccgacgg aagcacagcg gccaccgcca gtgggcctgc    600
tcccgctgct ccaaggcgta cgccgtccac tccgactaca aggcgcacct caagacctgc    660
ggcacccgcg gccacacctg cgactgcggc gcgtcttct cccgggtgga gagctttatc    720
gagcaccagg acatgtgcga cgccagccgg ccccgggggcg cacgacgtc gtcgtcgcca    780 ggccatggag gcggcagggt ggtaggcgct tccaacccgc agcacctgct acatgcggcg    840
tctctgtcac ggacggcgtc aagtgcaagc ccctccagcg ggggcgaact cgtggggagc    900
ccggtggcct ggccttgcgg cccggcgaca gcaagcccca cggctgccaa cgtagcagca    960
ttccaacggc tgctcgatcc cactcagtca tcgtcacctc caacgccgtc cgaccgccgc   1020
ggcgccggca cccaaaaacct ggagctgcag ctcatgccgc cgcgcggggg cggagcggct   1080
cctcctggta cggctcttac gtatcgtgcg tcgccgtgtt caccttccgt tcttcacgct   1140
ccccgacagc tgggcgcgga cgcggtgcgg ctacagctct ccatcggctg cggcggcgcg   1200
cctgacgaca gcagcgtgga gtcggcgccg gcgccggctg caacgctgaa ggaggaggcc   1260
cgggagcagc taaggctggc gacggccgag atggcctcgg cggaggagac gcgggcgcag   1320
gcgaggcgtc aggtggagct ggccgagcag gagctggcgg gcgcaagacg cgtgcggcag   1380
caggcgcagc tggagctcgg ccgcgcccac gcgctccgcg accacgctgt gcgccagatc   1440
gacgcaacgc tgatggagat cacctgctac ggctgccgcc acaacttccg ggcgagggcg   1500
gccgccatga actgcgaggt agccagctac gtgtcgtccg tgctgaccga gggcggcgac   1560
gccgaggtcg acaacgacgg ccaccaccag ctcctccatg ccggggacct gccaagaagc   1620
caccgtgcca tgatgaagat ggacctcaac taggtccatc tagctgccta gctgactcgt   1680
ctcacggatg tttattaacc ttcagcgttt tttaggtttc ctttaacatt cagcttgctc   1740
tcctgtcttt tgtttcacca acgagatagg agatcgatgt gctgcgtgat ggtgtaattt   1800
gacgagatga ttgccataat atgccctcta ggtacagact ctaaaaaaaa aa          1852

<210> SEQ ID NO 12
<211> LENGTH: 2219
<212> TYPE: DNA
<213> ORGANISM: Lolium perenne
```

<400> SEQUENCE: 12

```
gtttggattt tgtcctgtac atggttgcta cctcaatacc acagctagca ggcttctagc        60
tagatcctgg tcatatttat gtctttcctt ctcacgtaca tacgcgcgca gctgttctca       120
tcgatcctct cctgcttgtc tttgtcttgt agatccacaa gacgccgccg aagcaagca        180
gtagctgcaa ttaatcgaat cccatgtcgt cgccttgtgt tcttctctag actcactgac       240
agactaggac tggacgactg ctcggtggcg gcgctcacct gaagccaaca acaagcaatt       300
ggaaggagta gctagctgat tgttctattc gaccgatggc cgccgcctcg tccgctccct       360
tcttcggcct ctccgacgcg cagatgcagc cgatggtgcc cgcgcagcct cccgctcccg       420
ttgccgccgc gccggcgccc aagaagaagc gcaaccagcc aggcaaccca atccggacg        480
cggaggtgat cgcgctgtcg ccgcgctccc tgatggcgac gaaccggttc gtgtgcgagg       540
tgtgcggcaa ggggttccag cgggagcaga acctgcagct gcaccgccgc ggccacaacc       600
tgccctggaa gctgaagcag aagaacccca aggacgccct cgcggcggcg tgtacctgt        660
gcccggagcc gacctgcgtg caccacgacc cggccagggc cctcggcgac ctcaccggga       720
tcaagaagca ctactgccgc aagcacgcg agaagaagtg gaagtgcgac aagtgcgcca       780
agcgctacgc cgtgcagtcc gactggaagg cgcactccaa gacctgcggc acaagggagt       840
accgctgcga ctgcggcacc ctcttctcca ggagggacag cttcatcacc accgcgcct       900
tctgcgacgc gctggcccag gagagcgcgc gcttgcccgc gatcggcgcc agcctatacg       960
gtggcgtcgg aaacatgggc gccctcaaca ctctctccgg catgcccaa caactgccgg      1020
gcggcagctt tcctgaccag tccggccacc actcctcggc gtcggctatg acatccaca      1080
accttggcgc tggcagcaat gccggccagt tcgaccagca cctcatgcca cagtccgcgg      1140
gatcctccat gttccgctcc caggccgcct cgtcttcccc gtactacctc ggcgccgccg      1200
ccgcccagga cttcgccgag gatgacgtcc accgctccca tggcaaccag agctctcttc      1260
tccagggcaa gtcgacggcg gccttccacg gcctgatgca acttccagac cagcaccagg      1320
gaagcgcaag caacggtaac aacaacctcc tgaaccttgg cttctattcg ggcaacggcg      1380
gcggccagga cgggcgtgtc atgttccaga accagttcaa cagcagcgcc ggaaacggca      1440
acgtcaatgc tgagaacaat ggaagcctcc tcggcggcgg tggtgggggt ttcccttcgc      1500
tgttcggttc gtctgagtca ggcggcggac tcccgcagat gtcggcgacg gcgctgctgc      1560
agaaagcggc gcagatgggc gcgacgacga gcagccacaa cgcgagcgcc gggctgatgc      1620
gtggccctgg gatgagggt ggcgccggag aaggcgggtc ttcgtcgtct gcgagcgaga      1680
ggcagtcgtt ccatgacctc attatgaact ccctggcgaa cgggagcggc gctcctgcta      1740
ctacgggtgg tggcacagtg gcgttcggcg gcggcggctt ccccatcgac gacggcaagc      1800
tgagcacgag ggacttcctg ggtgtcggtc ccggtggcgt ggtgcacgct ggcatgggcc      1860
cgccccggcg gcaggtggc gctgccgggc tccacatcgg ctcgctggac ccggccgagc      1920
tgaagtagtc cgcaagaatc gacaaaaaac aaaacaagaa acatgcatg catgcaaaaa       1980
aaaaatcttg aagattttca tggaacatca catcaggacg tcaaggacta gtcaggagtg      2040
aggacaaggt taatttcttg gataatctat cagcatgtat tagttgatgc atgtgttcat      2100
gttggcatag ctagctgcgt taggtagccg gttcaataac cctgtgaggc cagaacttca      2160
gtttaatttt gctgttcgta caaactgtca attagctgtt ttttctgtca aaaaaaaaa       2219
```

<210> SEQ ID NO 13
<211> LENGTH: 2257

<212> TYPE: DNA
<213> ORGANISM: Festuca arundinacea

<400> SEQUENCE: 13

```
gcacccccaca ccgcagcagc gagcgcctca acccgatgcc gctgccgctc tgactcccat    60
ccatctcccc cagcccagcc cccagtcgaa agcaacccag ccagccagca gcgagcgaga   120
gaacaagcac ggaaaggagg ggaaaattct tccgtccgcc accgccgact cgcgccccgt   180
tcgccgacgc ggattgggag ggtggatacg gggcggctgg agggcggcgg gctgggtcga   240
gcggcggccg tggcgccaga tcgagcgggg atgccgccca atccgacgga cccggagcag   300
ccggaggcgg ccgcggcgcc ggccccgccg cccaagaaga gaggaacct gcccgggacc    360
ccagatccgg acgcggaggt gatcgcgctg tcgccgggga cgctcatggc caccaaccgc   420
ttcgtgtgcg aggtctgcgg caagggcttc cagcgggacc agaacctgca gctgcaccgc   480
cggggccaca acctgccctg cgcctccgc cagcgcgggc ccggcgccgc ccgccgcgc    540
cggagggtct acgtctgccc ggagccaggg tgcgtgcacc acgccccggc ccgcgcgctc   600
ggggacctca cgggcatcaa gaagcacttc tgccgcaagc acggcgagaa gcgatgggcg   660
tgcccgcgct gcggcaagcg ctacgccgtc caggccgacc tcaaggcgca cgccaagacc   720
tgcggcaccc gcgagtaccg atgcgactgc ggcacgctct tcaccaggcg agacagcttc   780
gtgacacatc gagccttctg tggtgccctc gtcgaggaga ctggcagagt gctcgccgtt   840
ccggccccgc ctgctcccgg gccgcctgat ttggacgatg ttgacgagaa ttttgacaag   900
gacagtgaga agggagagga gaatgtggaa gatgaggagg agaaaggtga agtaaatgag   960
aattctgctg tggctgacgt gaatgagcct cagcgcgtcg aggcagcgtc tgaggcgccg  1020
cagcgcattc cttcgccgca gcagcagcgc attccgtcgc cgcggcgcat tccctcacca  1080
cagcgcattc ggtcgccacc atctccagta ccacaggagc agcagcagca gccgatggtg  1140
gcagtggtgc caatttgga ggggccaaag gtggctgcgg agccaattgt ggttgtcaag    1200
caggaggagg atgacaagcg agatgaagat gtttgcttcc aggaagccga taaatacgac  1260
gacgctgaat tggaaggctc cagcctgcca gatactgata ccccgatgct tccttgtttc  1320
ctcccgtcgc cctcggatgc cattggtaca gatggcagca gcaccagctg tggcacggtc  1380
agcagtgctt ccattccatt gcgccagcaa cgacgactag cacatttgct gggctgtttg  1440
catcggccac gacaagcacc actccccaga gtagatcgct gcgtgatctt atcggtgttg  1500
atcccacctt cctttgcctt gcgattggta cgccctcctc tctgttcccg cagacaaacg  1560
cgagcaaccc tggcagcttt gctccacctc cagcaccaca catgtccgcg actgcactcc  1620
tgcagaaggc tgctgaggct ggagcttcgc aagcaggcac gtctttcttg aaggagtttg  1680
gtctggcaag ttcctcatca tcaaccccat ccaggccacc tcaagggagg tctatggata  1740
gctcaacaca atctcagcag cctcaaggaa ggtttatcga cagctcaaga cagtcgcagc  1800
tacctcaaga gaggttcatc aataactcga tgccatccag gctgtctcaa gggagattca  1860
tggataccctc actaccatct cagcagctac ctcaaaggag attcatggat accgcactac  1920
catcccagca gctacctcaa gggagattca tggataacgc actaccgtcc cagcagcaac  1980
agggtaagt agttgccttt attactggtt gcttgtggtg ccaaattgcc agcgcaggat   2040
ttgcttcgta aaaggaaagg atgagactgg gacagccgca tgtgaaaggt gttttttcag  2100
ttttcgcctg ttgatgtcgg tcactatatc tgcccaactc tctcccctt gcgagtctcg    2160
cctctgcact tttgagagta ttcattgtta cattgttttg tccctgttga ccatacgaga  2220
```

```
agatattagc aagtcatttg ctttgcaaaa aaaaaaa                              2257
```

<210> SEQ ID NO 14
<211> LENGTH: 2581
<212> TYPE: DNA
<213> ORGANISM: Festuca arundinacea

<400> SEQUENCE: 14

```
ggtggagccg gccggaccgg aagaggagga agacggccag gccaggccaa gtgaaggcgg     60
cgtcggaggg cttctcctgc cggaatcccc ccctcccttg ccattgccat ggcgcggagc    120
aactggggagg ccgacaagat gctggacgtg tacatctacg actacctggt caagcgcaac    180
ctccacaact ccgccaaggc cttcatgaac gagggcaagg tcgccaccga tcccgtcgcc    240
atcgatgcgc cgggggggatt cctctttgag tggtggtcca tcttctggga catcttcgac    300
gccaggacca gggacaagcc gcaccaaggg gcaaccgcgg cttctatagat tcttatgaag    360
tcaagggaac aacagatgag aatccaacta ttacaacagc agaacgctca cctgcagaga    420
agagatccaa atcatccggc cgttaacggt gctatgaaca actctgatgt atcggcattt    480
ctggtttcaa aaatgatgga agaaagaaca aggaatcatg gtcccatgga ctcagaggcg    540
tcacagcaac tcttagaggc gaataagatg gctcttctca agtcagcagc agctaatcag    600
actgggccgc ttcagggtag ctcggtcaat atgtcagctc tgcagcagat gcaggcgaga    660
aatcaacaag ttgacatcaa aggtgatggt gctatgccac aacgaacaat gcctacagac    720
ccttctgcat atacgcagc agggatgatg caaccaaaat ctggattagt tgcttctgga    780
ctaaatcaag gagttgggag tgtaccactg aaaggctggc cgctaacagt cccaggtatc    840
gatcaactgc ggtcaaattt aggcgcacag aagcagttga tgccatcccc aaaccaattt    900
caacttttat caccacaaca gcaattaatt gctcaagcac aaacacagaa tgaccttgct    960
agaatgggtt cgccagctcc atctggttcc caaagattc ggccaaatga acaggaatat    1020
ttgattaaga tgaaaatggc ccagatgcag cagtcaggtc aacggatgat ggaattgcaa    1080
cagcagcagc atcatctgca acaacaacaa caacagcagc aacatcaaca gcagcagcag    1140
cagcagcagc agcagcagca gatgcaacag aatactagaa aacggaagcc aacttcttct    1200
ggggctgcta atagtacagg cacaggaaat accgttggac cttctccgcc ctcaactcca    1260
tcaacacata ctcctggtgg tggaatacca gtagctagca acgcgaacat tgcgcaaaag    1320
aattcaatgg tttgcggcac ggatgggacc agtggatttg cttcatcctc aaatcagatg    1380
gacaacttgg atagtttcgt tgattttgat gacaatgttg attcatttt gtcaaatgat    1440
gatggggatg gcgagacat atttgctgca atgaagaaag cccctcaga gcaggagtct    1500
ctaaagagtc tttctttgac tgaggttggt aataatcgca caagcaacaa caaggttgtt    1560
tgctgtcatt tctctacaga cgggaagtta cttgccagtg ctggtcatga aaaaaagctc    1620
ttcctctgga atatggataa ttttagcatg gacactaaag cagaagaaca tacaaatttt    1680
ataacggaca taagattcag gccaaattca actcagttgg ctacatcatc ttctgatgga    1740
actgttcgat tatggaacgc tgttgaacga accggcgctt tacagacttt ccacgggcac    1800
acctcccacg tgacttcggt agacttccac ccaaaactaa cggaggtcct tgctcatgc    1860
gatgacaaca gagagctccg gttctggacg gtcggtcaga acgcaccttc acgtgtcacc    1920
agggtcaaac agggcggtac tggtagggtg aggttccagc ctcggatggg gcagctcctt    1980
gcggtggctg ctgggaacac ggtgaacatc atcgatatcg agaaggacac gagtctgcat    2040
tcacagccaa aggtccactc gggcgaggtg aactgcatct gctgggatga gagcggcgag    2100
```

```
tacctggcgt cagcgagcca ggacagcgtg aaggtgtggt cagcggcgtc aggcgcgtgc    2160
gttcacgagc tgcggtccca tgggaaccag taccagtcgt gtatattcca ccctcgatac    2220
ccgaaggtct tgattgtggg cggttatcag acgatggagc tgtggagtct gtcggacaac    2280
cagaggaacg tggtggcagc gcacgagggg cttatcgcgg cgctggcgca ctccccgtcc    2340
acggggtcgg tggcctccgc cagccacgac aaatccgtga agctgtggaa gtagatggaa    2400
aggccgggaa cctgggcaaa atggtgccac gacgacgagc gtgtgtgttc tgggggtgat    2460
gagaggttag acgcatgtac gtacgttacg ttacatagag gaggagttaa gaatgtgtaa    2520
ttaaactgag gcgactggat caatcaattt taatggaaga aactgtgcta taaaaaaaaa    2580
a                                                                   2581

<210> SEQ ID NO 15
<211> LENGTH: 2582
<212> TYPE: DNA
<213> ORGANISM: Festuca arundinacea

<400> SEQUENCE: 15
gagacagcga ggtggtgcgg gtggaggccg gaccggaagg aagaggagga agacggccag      60
gccaagtgaa ggcggcgtcg gagggcttct cctgccggaa tccctcccc ctaccctccc     120 ctcctcccctt gccattgcca tggcgcggag caactgggag gccgacaaga tgctggacgt    180
gtacatctac gactacctgg tcaagcgcaa cctccacaac tccgccaagg ccttcatgaa    240
cgagggcaag gtcgccaccg atcccgtcgc catcgatgcg ccggggggat tcctctttga    300
gtggtggtcc atcttctggg acatcttcga cgccaggacc agggacaagc cgccccaagg    360
ggccaccgcg gcttctatag atcttatgaa gtcaagggaa caacagatga gaatccaact    420
gttacaacag cagaacgccc acctgcagag aagagatcca aatcatccgg ccgttaacgg    480
tgctatgaac aactctgatg tatcggcatt tctggtttca aaaatgatgg aagaaagaac    540
aaggaatcat ggtcccatgg actcagaggc gtcacagcaa ctcttagagg cgaataagat    600
ggctcttctc aagtcagcag cagctaatca gactgggccg cttcagggta gctcggtcaa    660
tatgtcagct ctgcagcaga tgcaggcgag aaatcagcaa gttgacatca aaggtgatgg    720
tgctatgcca caacgaacaa tgcctacaga cccttctgca ttatacgcag cagggatgat    780
gcaaccaaaa tctggattag ttgcttctgg actaaatcaa ggaattggga gtgtaccact    840
gaaaggctgg ccgctaacag tcccaggtat cgatcaactg cggtcaaatt taggcgcaca    900
gaagcagttg atgccatccc caaaccaatt tcaacttttta tcaccacaac agcaattaat    960
tgctcaagca caaacacaga atgaccttgc tagaatgggg tcgccagctc catctggttc   1020
cccaaagatt cggccaaatg aacaggaata tttgattaag atgaaaatgg cccagatgca   1080
gcagtcaggt caacggatga tggaattgca acagcagcag catcatctgc aacaacaaca   1140
acaacagcag caacatcaac agcagcagca gcagcagcag atgcaacaga atactagaaa   1200
acggaagcca acttcttctg gggctgctaa tagtacaggc acaggaaata ccgttgggcc   1260
ttctccgccc tcaactccat caacacatac tcctggtggt ggaataccag tagctagcaa   1320
cgcgaacatt gcgcaaaaga attcaatggt ttgcggcacg gatgggacca gtggatttgc   1380
ttcatcctca aatcagatgg acaacttgga tagtttcgtt gatttgatg acaacgttga   1440 ttcattttg tcaatgatg atggggatgg gcgagacata tttgctgcaa tgaagaaagg   1500
cccctcagag caggagtctc taaagagtct ttctttgact gaggttggta ataatcgcac   1560
```

-continued

```
aagcaacaac aaggttgttt gctgtcattt ctctacagac gggaagttac ttgccagtgc    1620
tggtcatgaa aaaagctct tccctctgga a tatggataat tttagcatgg acactaaagc   1680
agaagaacat acaaacttta taacggacat aagattcagg ccaaattcaa ctcagttggc    1740
tacatcatct tctgatggaa ctgttcgatt atggaacgct gttgaacgaa ccggcgcttt    1800
acagactttc cacgggcaca cctcccacgt gacttcggta gacttccacc caaaactaac    1860
ggaggtcctt tgctcatgcg atgacaacgg agagctccgg ttctggacgg tcggtcagaa    1920
cgcaccttca cgtgtcacca gggtcaaaca gggcggtact ggtagggtga ggttccagcc    1980
tcggatgggg cagctccttg cggtggctgc tgggaacacg tgaacatca tcgatatcga     2040 gaaggacacg ggtctgcatt cacagccaaa ggtccacccg ggcgaggtga actgcatctg    2100
ctgggatgag agcggcgagt acctggcgtc agcgagccag gacagcgtga aggtgtggtc    2160
agcggcgtca ggcgcgtgcg ttcacgagct gcggtcccat gggaaccagt accagtcgtg    2220
tatattccac cctcgatacc ccaaggtctt gattgtgggc ggttatcaga cgatggagct    2280
gtggagtctg tcggacaacc agaggaacgt ggtggcagcg cacgaggggc ttatcgcggc    2340
gctggcgcac tccctgtcca cggggtcggt ggcctccgcc agccacgaca gttccgtgaa    2400
gctgtggaag tagatggaaa ggccgggaac ctgggctggt gccacgacga cgagcatgtg    2460
tgttgtgggg gtacgtgatg agaggttaga cgcatgtacg tacgttacgt tacatagagg    2520
agttaagaat gtgtaattaa actgaggcga ctggatcaat caattttaat ggaaaaaaaa    2580
aa                                                                   2582
```

<210> SEQ ID NO 16
<211> LENGTH: 1053
<212> TYPE: DNA
<213> ORGANISM: Festuca arundinacea

<400> SEQUENCE: 16

```
gaattacctg agcttccatt cagcaaagag gcacacacgc acactgatca tccctccggt     60
tccgatttca aggcatcaac atgtcaaggg cgttggagcc tctcgttgtg gggaaggtga    120
tcggtgaggt gctggacagc ttcaacccca ccgtgaagat ggcggcaacc tacaactcca    180
acaagcaggt gttcaacggc catgagttct tcccctcggc catcgccgcg aagccgcgtg    240
tcgaggttca ggggggcgac cttagatcct tcttcacatt ggtgatgact gaccctgatg    300
tgccaggacc cagtgatccg tacctgaggg agcatcttca ctggattgtt actgatattc    360
ctgggactac tgatgcttct tttgggaagg aggtggtgaa ctacgagagc ccaaagccaa    420
acatcggcat ccacaggttc atcctcgtgc tgttccagca gacgcaccgg ggctcggtaa    480
agaacacacc gtcgtcgagg gaccgcttca ggacccgcga gttcgccaag gataacgagc    540
tcggcctccc tgtcgccgct gtctacttca cgcgcagcg ggagaccgcc gcccgccggc    600
gatagctcaa cggcaaccga accaaccaac aagcaacacc cccctactat gtacctgatc    660
tagctacatg ataaaacgaa ctgcgtacga tcacctatta gctagcttcg atggcctttc    720
ctgctacatc caagcatgca caatgtctga ataaaacaca ccggtaaatt agctgtttgc    780
acgagaaagc tgctccctac tagtacgtag ccgttgccca tttagttaat ttttgtgaag    840
gtgacaagat cgatgattgg gaagagattg cagtgttgac tgagaaaaaa gtgcaagatt    900
tgaagcaata atagtcgtca gggagtataa gttacgtgtc gagtgcccaa gggaggggaa    960
gaagtggaca tggctctagt attcccctac ccactagtat tctgttatgt ggttttctt    1020 cattggatcg aagtttgcag cgtaaaaaaa aaa                                 1053
```

<210> SEQ ID NO 17
<211> LENGTH: 2421
<212> TYPE: DNA
<213> ORGANISM: Festuca arundinacea

<400> SEQUENCE: 17

| | | | | | |
|---|---|---|---|---|---|
| gcaacaccac | catttgatgc | agctcacaaa | gaagaatcct | caagctgctg | cggctgccca | 60 |
| acttaacctc | ttgcaacagc | agcggatcat | gcatatgcag | cagcagcaac | aacaacagat | 120 |
| tctgaaaaac | ctgcctttac | agagaaacca | attacagcag | cagcagcagg | tgcagcagca | 180 |
| gcagcagcaa | caactacaac | agcagcagca | gctacttcgt | caacagagtc | taaacatgag | 240 |
| aactccagga | aagtcgcctc | cctatgagcc | aggtacctgt | gcaaagagat | tgacccatta | 300 |
| catgtatcac | caacaaaaca | ggccgcagga | taacaatatc | gagtactgga | gaaactttgt | 360 |
| caatgagtat | tttgctccaa | ctgctaaaaa | gaggtggtgt | gtctctctct | atggaagtgg | 420 |
| tcgtcaaact | actggagttt | ccctcagga | tgtctggcac | tgcgaaatat | gcaatcggaa | 480 |
| gcctggccgg | ggcttcgaga | caacagttga | ggtcttgccg | cgattatgcc | aaatcaaata | 540 |
| tgcgagtggt | acattggaag | aactactgta | tatcgatatg | ccacgtgagt | ccaagaatgt | 600 |
| atctggtcag | attgttctgg | actatacaaa | agcaattcaa | gaaagtgtct | ttgatcaatt | 660 |
| gcgtgtcgta | cgtgagggggc | atctgaggat | aattttaat | ccagacctca | agatcgcatc | 720 |
| ttgggagttc | tgtgctaggc | gtcatgagga | acttattcca | cggaggtcaa | taataccgca | 780 |
| ggttagtcag | cttggcgcag | ttgtacagaa | ataccaggct | gctgctcaaa | acccaaccag | 840 |
| tttatcaact | caggacatgc | agaataattg | caactcgttt | gtggcatgtg | cccgtcaatt | 900 |
| ggctaaagct | ctggaggtgc | ctctggtaaa | tgatttagga | tatacaaaac | gatatgtccg | 960 |
| ctgtcttcag | attgcggagg | tggtgaactg | tatgaaagat | ttgattgacc | acagcaggca | 1020 |
| gactggatct | ggaccaatcg | atagcctgca | caagtttcct | cgcaggactc | catcagggat | 1080 |
| caaccctctt | caatcacagc | agcaacagcc | tgaagagcac | caatctgttc | cccagagttc | 1140 |
| aaaccagagt | ggtcaaaatt | ctgctcctat | ggctggtgtg | caggtttctg | cctctgctaa | 1200 |
| tgcggatgcc | acatcaaata | attcgatcaa | ctgtgcaccc | tctacatctg | caccctcacc | 1260 |
| aactgttgtt | gggctcctcc | aaggttcaat | ggattctaga | cacaatcatc | caatgtgcag | 1320 |
| cgcaaatggc | cagtataaca | gtgggaataa | tggcgcaatt | cccagggtga | actccgcaag | 1380 |
| ctcattacag | tcaaatccat | ctagtccttt | cccttcgcag | gtgcctacat | cacccaataa | 1440 |
| caacatgatg | ccgacccttc | agaacgcaaa | ccaactcagt | tctcccccag | cagtatcatc | 1500 |
| aaacttacct | ccaattcagc | ctccttcaac | tcggcctcag | gagtctgagc | caagtgatgc | 1560 |
| ccaaagctcg | gttcagagaa | tcttgcaaga | gatgatgtca | tcacaaatga | atggtgttgg | 1620 |
| ccatggaggg | aatgacatga | agaggccaaa | tgggcttacc | cctggtatta | atggggttaa | 1680 |
| ctgcttagtt | ggtaacgccg | tcacaaatca | ctccggaatg | ggaggaatgg | gatttggggc | 1740 |
| catgggcggg | tttggttcga | ctcctgcagc | aagtggactc | agaatggcaa | tgacgaataa | 1800 |
| tgcaatggca | atgaatggta | ggatgggaat | gcatcacagt | gcacaagacc | tatcacagtt | 1860 |
| gggccagcag | caccagcacc | agcaccagca | tgacatagga | aatcagctgt | ggggtggact | 1920 |
| tggagcagca | aacagcttca | ataatattca | gtatgattgg | aaaccctctc | aatagagtgg | 1980 |
| ccggaaacat | tagaaagtat | gatgacgatg | atatgcagct | gtcctggctg | ggctaattga | 2040 |
| ttatggagca | tcaagggcag | caccataaca | acgccccttg | ggtcaaagcg | tttgggcttt | 2100 |

-continued

```
tgctccaatg gtgccatggc aaggaatcat aagcgacggc aaacacctga gctggtcact    2160
gtatgtcgca acggttagtt tagctggttc gttgtgtatt atgcaactat ggcactgagc    2220
tacctgcctc agttatctta ccaaaagatg agttaaagga ttataacctg ccagcaccgg    2280
gcaccgttgg tgtctgtgta tggccttatt tctcacccag aaaagaagtt ttccctctct    2340
tttttcgttg acggatgaca tccaatctgt atttatcacc ccccttgct gtagtaatca    2400 tatgtgctga taaaaaaaaa a                                              2421
```

<210> SEQ ID NO 18
<211> LENGTH: 2833
<212> TYPE: DNA
<213> ORGANISM: Festuca arundinacea

<400> SEQUENCE: 18

```
agcgattgag cccgccgaag ctcgccgccc gccagccaag ctaaaagata tgaagactct      60
tagccaataa gcaagattct gtaaggctgc aacattggta acctccatgt ctggggcccc     120
acgctccaat cttggatttg ttgccaggga catgaatggt agcattccag ttagttctgc     180
aaattcctct gggccaagta tcggtgttag ctctttggtg accgatggca attcatcact     240
ctccggaggt gcccagtttc agcatagtac gagcatgaat gctgattcat tcatgcgcct     300
tcctgcctcc ccgatgtcat tttcatccaa taacatatct ggctcatcag tcatcgatgg     360
gtccatcatg cagcaaagtc caccccaaga tcagatgcag aagcgcagat catctactgc     420
aacgtcccaa cctgggattg aggctggcgc tgcattccat gctcagaaga agccaagggt     480
cgatattagg caagacgata tcctgcaaca acacttgatt cagcaggtgc tccaaggtca     540
aagttctctc catctcccgg gccaacataa cccacagctt caagctttga tccgtcagca     600
gaaactggca catattcagc atctacagca gcagcagttg tcacaacaat ttcctcaaat     660
ccagcaatca caagttggca tacctcgtca gccgcagttg aggctgccac tagcacagcc     720
tggcatgcag ctagctggac ctgttaggac tcctgtcgag agtgggcttt gttctcgaag     780
gttaatgcag tatttgtttc ataagcggca ccggccagag gataatccca taacttactg     840
gaggaagctt attgatgaat attttgcacc acgagcaaga gaaagatggt gtgtgtcatc     900
atatgaaaaa agagggaatt ctccagttgc tattccacag acatctcagg atacatggcg     960
ttgtgatatt tgcaatacac atgcagggaa aggacatgag gctacctatg aaatacttcc    1020
tagactatgt cagattcgat ttgaccaagg tgttatagat gaatatctat tcctggacat    1080
gcccaatgaa ttccggttgc ccaatggatt acttctcctg gagcatacta agttgttca    1140 gaagagcatc tatgatcatc tacatgttac acacgagggg caactgagaa taatattcac    1200
tccagaacta aagattatgt cttgggagtt ctgttcacga cgacatgacg agtatatcac    1260
tcgcaggttt ctaacaccac aggttaatca tatgctgcaa gttgcccaga gtatcaagc    1320 tgctgccaat gaaagtgggc tgctggggt atcgaacaat gatgcacaag ccatttgcag    1380
catgtttgtg tctgcatcac ggcaattagc gaaaaatcta gaccaccaca gcttaaatga    1440
gcatggtctc tctaaaagat atgttcgctg cttgcagata tcagaggtgg tgaatcacat    1500
gaaggactta attgagttca gccacaagaa caagcttggt cctatagagg gtctgaagaa    1560
ctatcccaga caaaccggac caaagcttac aacgcagaac atgcatgatg caaaggggt    1620 ggtcaaaacg gaagaaagta cacatgtgaa taacgagggt ccagatgctg acccgctgg    1680 tagcagtcct cagaatgctg gagcacaaaa caactaccag aatatgctga gaagcccaag    1740
cccaaatcag ggactgactc accaggaggc atcccagaat gccgcggcac tgaacaacta    1800
```

-continued

| | |
|---|---|
| ccagaatatg cttagaagct caagcgcaaa ccagggtttg cttcagcagg aggcttcaca | 1860 |
| gaatgtgtcg gggttaaata attaccagaa tatgcttaga agctcgagtg cgaaccagag | 1920 |
| tatccttcag caggaggcat cgagcatctt taaaggccct acaggagtgc acagtagcat | 1980 |
| tcagctggaa gcggctagat ccttccgcgc ggctcagctt gggcccatgt cgtttcagca | 2040 |
| agctgtgccc ctgtatcagc agaacaggtt tggggctggt gtgagtccgc agtaccagca | 2100 |
| gcatgtcatg cagcagctgc tgcaagaagc caacaggagt accaacaacc gggttctggc | 2160 |
| gcagcagcag cctcttagca ctcccaatgc aaacggaggt ctcacgatca ccaacagcgg | 2220 |
| tgctagtgga gatcaggcac aacacatgaa taataacgga gccgcaaagg gcgtggcagc | 2280 |
| tccaatgggt atggcgggaa ccagcaatct gatcaacagc ggatcagctg gggtcgtcca | 2340 |
| gcgatgcagc agcttcaagt cggtgactag caaccccgct gctgccgcgg ctggcaacct | 2400 |
| gctgaccccc aaggccgagt ccatgcacga gatggacgag cttgaccatc tcatcactag | 2460 |
| cgagctcgcg gagagcgggc tgttcatggg ggagcagcag ggaggtggtg gcggctactc | 2520 |
| atggcacatg tgagagagac tgctaaatta acctatatag ttcatctgtt ctgcgagttg | 2580 |
| tgtttgatgt gtaaccgccg tagattattc ggagtctttc ttccttttt tcgagcttcc | 2640 |
| gtgtagctga ctggaacgga tggaaccttg agttatgtga gtgtgagctg gcttgggaat | 2700 |
| tgtgagcag tgcagcccag tgttattatc tatggaatga catggtgtgg ttgtcgtttg | 2760 |
| tgctgcaaca ttgctgattt cccgtgtccc tagaaaattg ctgattttt cctgtgggct | 2820 |
| tttaaaaaaa aaa | 2833 |

<210> SEQ ID NO 19
<211> LENGTH: 2780
<212> TYPE: DNA
<213> ORGANISM: Festuca arundinacea

<400> SEQUENCE: 19

| | |
|---|---|
| gtctgatcct ctgtcattcc catcatcctc ccatgttagt ttgggcaatc acataagttc | 60 |
| agataatttg cagcagcagc agcagatgga tatgccggat ttgcagcagc agcagcaaca | 120 |
| acaacaacgt caactaccaa tgtcttacaa ccaacagcac ttgccaatgc aacggccgca | 180 |
| gccacaggct acagtgaagt tggagaatgg tggcagtatg ggtggagtta aaatggagca | 240 |
| gcagacaggg catcctgatc agaatggccc agcccagatg atgcacaatt ctggcaatgt | 300 |
| aaaatttgag ccacacagt tgcaggcgtt gaggggtttg ggcacggtga agatggagca | 360 |
| accgaattca gacccgtcag cattcttgca gcaacagcag caacaacagc agcaacacca | 420 |
| ccatttgatg cagctcacaa agcagaatcc tcaagctgct gcggctgccc aacttaacct | 480 |
| cttgcaacag cagcggatca tgcatatgca gcagcagcaa caacaacata ttctgaaaaa | 540 |
| catgccttta cagagaaacc aattacaaca gcagcagcag caacaacaac aactacaaca | 600 |
| acagcagcat cagcagctac ttcgtcaaca gagtctaaac atgagaactc caggaaagtc | 660 |
| gcctccctat gagccaggta cctgtgcaaa gagattgacc cattacatgt atcaccagca | 720 |
| aaacaggcca caggataaca atgtcgagta ctggagaaac tttgtcaatg agtattttgc | 780 |
| tccaactgct aaaagaggt ggtgtgtctc tctctatgga agtggtcgtc aaactactgg | 840 |
| agttttccct caggatgtct ggcactgcga aatatgcaat cggaagcctg gccggggctt | 900 |
| cgagacaaca gttgaggtct taccgcgatt atgccaaatc aaatatgcga gtggtacatt | 960 |
| ggaagaacta ctgtatatcg atatgccacg tgagtccaag aacgtatctg gtcagattgt | 1020 |

| | |
|---|---|
| tctggactat acaaaagcaa ttcaagaaag tgtctttgat caattgcgtg tcgtacgtga | 1080 |
| ggggcatctg aggataattt ttaatccaga cctcaagatt gcatcttggg agttctgtgc | 1140 |
| taggcgtcat gaggaactta ttccacggag gtcaataata ccgcaggtta gtcagcttgg | 1200 |
| cgcggttgta cagaaatacc aggctgctgc tcaaaaccca accagtttat caactcagga | 1260 |
| cctgcagaat aattgcaact cgtttgtggc atgtgcccgt caattggcta aagctctgga | 1320 |
| ggtgcctctg gtaaatgatt taggatatac caaacgatac gtccgctgtc ttcagattgc | 1380 |
| ggaggtggtg aactgtatga aagatttgat tgaccacagc aggcagactg gatctggacc | 1440 |
| aattgatagc ctgcacaagt ttcctcgcag gactccatca gggatcaacc ctcttcaatc | 1500 |
| acagcagcaa ccgcctgaag agcaacaatc tgttccccag agttcaaacc agagtggtca | 1560 |
| aaattctgct cctatggctg gtgtgcaggt ttctgcctct gctaatgcgg atgccacatc | 1620 |
| aaataattcg ctcaactgtg caccctctac atctgcaccc tcaccaacag ttgtgggct | 1680 |
| cctccaaggt tcaatggatt ctagacaaga tcatccaatg tgcagcgcaa atggccagta | 1740 |
| taacagtggg aataatggtg caattcccag ggtgaactcc gcaagctcgt tacagtcaaa | 1800 |
| tccatctagt cctttccctt tgcaggtgcc tacgtcaccc aataacaaca tgatgccgac | 1860 |
| ccttcagaac gcaaaccaac tcagttctcc cccagcagta tcaccaaact tacctccaat | 1920 |
| gcagcctcca tcaactcggc tcaggagtc tgagccaagt gatgcccaaa gctcagttca | 1980 |
| gagaatcttg caagagatga tgtcatcaca aatgaatggt gttggccatg cagggaatga | 2040 |
| catgaagagg ccaaatgggc ttaccccctgg tattaatggg gttaactgct tagttggtaa | 2100 |
| cgccgtcaca aatcactccg gaatgggagg aatgggattt ggggccatgg gcgggttcgg | 2160 |
| ttcgaatcct gcagccagtg gactcagaat ggcaatgacg aataatacaa tggcaatgaa | 2220 |
| tggtaggatg ggaatgcacc acagtgcaca tgacctatca cagttgggcc agcagcacca | 2280 |
| gcaccagcac cagcaccagc accagcacca gcatgacata ggaaatcagc tgttgggtgg | 2340 |
| acttagagca acaaatagct tcaataatat tcagtatgat tggaaaccct ctcaatagag | 2400 |
| tggccggaaa cattagaaag tcagtatgat gaagatgata tgcagctgtc ctggctgggc | 2460 |
| taattcatta tggagaatca agggcagcgc cataacaacg cccctgggt caaagcgttt | 2520 |
| gggcttttgc tccaatggtg ccatggcaag gaatcataag cgacggcaaa cacctgagct | 2580 |
| ggccactgta tgtctcaacg gttagtttag ctggttcgtt gtgtattatg caactatggc | 2640 |
| actgagctac cggcctcagt tatcttaccc aaagatgagt tgaaggatta taacctgcct | 2700 |
| gcacccggca ccgttggtgt ctgtgtatgg ccttatttct cacccagaaa agaagttttc | 2760 |
| cctccttttt aaaaaaaaaa | 2780 |

<210> SEQ ID NO 20
<211> LENGTH: 2302
<212> TYPE: DNA
<213> ORGANISM: Festuca arundinacea

<400> SEQUENCE: 20

| | |
|---|---|
| cctcgtgccg cttcctccct ttcccacgcc cgcttcccaa ccctggatcc aaatcccaac | 60 |
| ctatcccaaa accgaaaccg aggcaaggaa aagcatcgcg cagttattag ctagctagct | 120 |
| caaggcgaga tcatgaagcg tgagtaccaa gacgccggcg ggagcagcgc cggcggtgac | 180 |
| atgggcatgt ccaaggacaa gatgatgtcg gcgccgccgg cgcaggagga cgaggacgtc | 240 |
| gacgagctcc tcgcggcgct cgggtacaag gtgcgctcct ccgacatggc ggacgtcgcg | 300 |
| cagaagctgg agcagctgga gatggccatg gggatgggcg gcgtgcctgc gccggacgac | 360 |

```
ggcttcacca cgcacctggc caccgagacc gtgcactaca accccaccga cctctcctcc      420
tgggtcgaga gcatgctctc cgagctcaac gcgccgccgc cgctcccgcc ggccccgagg      480
ctcgctcccg cctccgccag cgtcacggcc gacggcttct tcgatatccc gccgccatcc      540
gtcgactcct ccagcagcac ctacgcgctg aggccgatcc cctcgccggc cgacctgtcc      600
gccgacctgt ctgccgactc cccgcgggac cccaagcgga tgcgtaccgg cggcggcagc      660
acgtcctcct cctcatcatc gtcatcctcc ctcggcggct gcgtggtgga ggccgctccg      720
ccggcggccg cggaggccaa cgccatcgcg ctgccggtcg tggtggccga cacgcaggag      780
gcagggatcc ggctggtgca cgcgctgctg gcgtgcgcgg aggccgtgca gcaggagaac      840
ttctcggccg ccgaggcgct ggtgaagcag atacccttgc tggcggcctc ccagggcggc      900
gccatgcgca aggtcgcggc ctacttcggc gaggccctcg cccgccgcgt cttccgcttc      960
cgcccgcagc ccgacagctc ccacctcgac gccgccttcg ccgacctcct ccacgcgcac     1020
ttctacgagt cctgccccta cctcaagttc gcccacttca ccgccaacca ggccatcctc     1080
gaggccttcg ccggctgccg ccgcgtccac gtcgtcgact tcggcatcaa gcaagggatg     1140
cagtggcccg ctcttctcca ggccctcgcc ctccgccccg gcggccctcc gtcgttccgc     1200
ctcaccggcg tgggcccacc gcagccggac gagaccgacg ccctgcagca ggtgggctgg     1260
aagctggccc agttcgcgca ccatcggcg gtcgatttcc agtaccgcgg cctcgtcgcc     1320
gccacgctcg ccgacctgga gccgttcatg ctgcagccag aggccgagga cggccccaac     1380
gaagaacccg aggtaatcgc cgtgaactca atcttcgaga tgcaccggct gctcgcgcag     1440
cccggcgccc tcgagaaggt cctgggcacc gtgcgcgccg tgcggccgag gatcgtgacc     1500
gtggtagagc aggaggccaa ccacaacgcc ggctcgttcc tggaccgatt caccgagtcc     1560
ctgcactact actccaccat gttcgattcg ctggagggcg ccggctccgg cccgtccgaa     1620
atctcgtcgg ggcctgctgc tgctgccgct gctcctggca cggaccaggt catgtccgag     1680
gtgtacctcg gccggcagat ctgcaatgtc gtggcctgcg agggcgcgga gcgcacggag     1740
cgccacgaga cgctggggca ttggcgcggc cgcctcggcc acgccgggtt cgagaccgtg     1800
cacctgggct ccaacgccta caagcaggcg agcacgctgc tggcgctctt cgccggcggc     1860
gacgggtaca aggtggacga aaggaaggc tgcctcacgc tcggctggca cacccgcccg     1920
ctgatcgcca cctccgcatg cgcatggcc gccgcgccct gatcgcaagt tttgaacgct     1980
gtaagtacac cacaccccga gcacggaaca caaccccccgc ccttggctca ccggcgcact     2040
tgaatgaagc taaaacgtcg acgaacgctg gattgcagcg accaacgatc ggagttaagg     2100
gcctcgctgg cgtgaagaga tggacaccgg atcgctccga ccacaccaga gcctgtaatt     2160
cgttcttgtt ctcgattccc cacttgatcc gtgaactcta gcagcctatt attaagtttt     2220
aaaatgtcta ttattgttct gtgtaattcc tgcaatcgct catatttaaa taaggacggg     2280
acggatttcg gtaaaaaaaa aa                                              2302
```

<210> SEQ ID NO 21
<211> LENGTH: 163
<212> TYPE: PRT
<213> ORGANISM: Lolium perenne

<400> SEQUENCE: 21

```
Met Ala Ala Glu Asp Lys Lys Ile Thr Leu Lys Ser Ser Asp Gly Glu
 1               5                  10                  15

Gln Phe Glu Val Asp Glu Ala Val Ala Met Glu Ser Gln Thr Ile Arg
```

```
                  20                  25                  30
His Met Ile Glu Asp Asp Cys Ala Asp Asn Gly Ile Pro Leu Pro Asn
            35                  40                  45

Val Asn Ala Lys Ile Leu Ser Lys Val Val Glu Tyr Cys Ser Lys His
        50                  55                  60

Val Gln Ala Ala Asp Gly Ala Ala Ala Asp Gly Ala Pro Ala Pro
65                  70                  75                  80

Pro Pro Ala Glu Asp Leu Lys Asn Trp Asp Ala Glu Phe Val Lys Val
                85                  90                  95

Asp Gln Ala Thr Leu Phe Asp Leu Ile Leu Ala Ala Asn Tyr Leu Asn
            100                 105                 110

Ile Lys Gly Leu Leu Asp Leu Thr Cys Gln Thr Val Ala Asp Met Ile
        115                 120                 125

Lys Gly Lys Thr Pro Glu Glu Ile Arg Lys Thr Phe Asn Ile Lys Asn
130                 135                 140

Asp Phe Thr Ala Glu Glu Glu Glu Ile Arg Arg Glu Asn Gln Trp
145                 150                 155                 160

Ala Phe Glu

<210> SEQ ID NO 22
<211> LENGTH: 169
<212> TYPE: PRT
<213> ORGANISM: Lolium perenne

<400> SEQUENCE: 22

Met Ala Ala Ala Asp Asp Ser Lys Lys Met Ile Thr Leu Lys Ser Ser
1               5                   10                  15

Asp Gly Glu Val Phe Glu Val Glu Glu Ala Val Ala Met Glu Ser Gln
            20                  25                  30

Thr Ile Arg His Met Ile Glu Asp Asp Cys Ala Asp Asn Gly Ile Pro
        35                  40                  45

Leu Pro Asn Val Asn Ser Lys Ile Leu Ser Lys Val Ile Glu Tyr Cys
    50                  55                  60

Asn Lys His Val Gln Ala Ala Lys Pro Ala Asp Ala Ala Ala Ala
65                  70                  75                  80

Asp Ser Ser Ala Ala Ala Pro Pro Glu Asp Leu Lys Asn Trp Asp
                85                  90                  95

Ala Glu Phe Val Lys Val Asp Gln Ala Thr Leu Phe Asp Leu Ile Leu
            100                 105                 110

Ala Ala Asn Tyr Leu Asn Ile Lys Gly Leu Leu Asp Leu Thr Cys Gln
        115                 120                 125

Thr Val Ala Asp Met Ile Lys Gly Lys Thr Pro Glu Glu Ile Arg Lys
    130                 135                 140

Thr Phe Asn Ile Lys Asn Asp Phe Thr Ala Glu Glu Glu Glu Ile
145                 150                 155                 160

Arg Arg Glu Asn Gln Trp Ala Phe Glu
                165

<210> SEQ ID NO 23
<211> LENGTH: 150
<212> TYPE: PRT
<213> ORGANISM: Lolium perenne

<400> SEQUENCE: 23

Ser Asp Gly Glu Glu Phe Glu Val Glu Glu Val Leu Val Leu Glu Ser
1               5                   10                  15
```

```
Gln Thr Ile Lys His Met Ile Glu Asp Glu Cys Asp Gly Val Ile Pro
             20                  25                  30

Leu Pro Asn Val Ser Ala Lys Ile Leu Ser Lys Val Ile Glu Tyr Cys
             35                  40                  45

Arg Lys His Val Gln Thr Arg Ala Ala Leu Ala Pro Asp Gly Asp Met
         50                  55                  60

Ser Thr Asn Ala Ala Gly Thr Glu Leu Lys Thr Phe Asp Glu Asp Phe
65                  70                  75                  80

Val Lys Val Asp Gln Ala Thr Leu Phe Asp Leu Ile Leu Ala Ala Asn
                 85                  90                  95

Tyr Leu Asp Ile Lys Gly Leu Leu Asp Leu Thr Cys Gln Thr Val Ala
             100                 105                 110

Asp Met Ile Lys Gly Lys Thr Pro Glu Glu Ile Arg Ala Thr Phe Asn
             115                 120                 125

Ile Lys Asn Asp Phe Thr Pro Glu Glu Glu Glu Val Arg Lys Glu
             130                 135                 140

Asn Ala Trp Ala Phe Glu
145                 150

<210> SEQ ID NO 24
<211> LENGTH: 654
<212> TYPE: PRT
<213> ORGANISM: Festuca arundinacea

<400> SEQUENCE: 24

Gly Gly Arg Gly Asp Tyr Ser Asp His Asp Asn Lys Ser Gly His Val
1               5                   10                  15

Lys Leu Phe Val Gly Ser Val Pro Arg Thr Ala Ser Glu Asp Asp Val
             20                  25                  30

Arg Pro Leu Phe Glu Asn His Gly Asp Val Leu Glu Val Ala Met Ile
         35                  40                  45

Arg Asp Arg Lys Thr Gly Glu Gln Gln Gly Cys Cys Phe Val Lys Tyr
     50                  55                  60

Ala Thr Ser Glu Glu Ala Glu Arg Ala Ile Arg Ala Leu His Asn Gln
65                  70                  75                  80

Trp Thr Ile Pro Gly Ala Met Gly Pro Val Gln Val Arg Tyr Ala Asp
                 85                  90                  95

Gly Glu Lys Glu Arg His Gly Ser Ile Glu His Lys Leu Phe Val Ala
             100                 105                 110

Ser Leu Asn Lys Gln Ala Thr Ala Lys Glu Ile Glu Glu Ile Phe Ala
             115                 120                 125

Pro Phe Gly His Val Glu Asp Val Tyr Ile Met Lys Asp Gly Met Lys
         130                 135                 140

Gln Ser Arg Gly Cys Gly Phe Val Lys Phe Ser Ser Lys Glu Pro Ala
145                 150                 155                 160

Leu Ala Ala Met Asn Ser Leu Ser Gly Thr Tyr Ile Met Arg Gly Cys
                 165                 170                 175

Glu Gln Pro Leu Ile Val Arg Phe Ala Asp Pro Lys Arg Pro Arg Pro
             180                 185                 190

Gly Glu Ser Arg Trp Leu Arg Met His Ile Cys Phe Ala Tyr Ile Pro
         195                 200                 205

Thr Leu His Tyr Phe Pro Leu Leu Leu Ser Glu Leu Ser Cys Leu Val
     210                 215                 220

Arg Gly Gly Pro Ala Phe Gly Gly Pro Gly Val Ser Pro Arg Ser Asp
```

-continued

```
            225                 230                 235                 240
Ala Ala Leu Val Ile Arg Pro Thr Ala Asn Leu Asp Glu Pro Arg Gly
                245                 250                 255
Arg His Met Pro Arg Asp Ala Trp Arg Pro Ser Ser Pro Ser Ser Val
            260                 265                 270
Ala Pro His Gln Phe Asn Asn Tyr Gly Ser Asp Asn Pro Met Gly Leu
            275                 280                 285
Met Gly Gly Thr Gly Thr Ser Ala Thr Asp Asn Gly Ala Phe Arg Pro
            290                 295                 300
Gln Met Phe Pro Gly Asn Gly Gln Thr Ala Val Pro Thr Ser Ser His
305                 310                 315                 320
Met Gly Ile Asn Thr Ser Ser Val Gln Gly His His Leu Gly Gly Gln
                325                 330                 335
Gln Ile Pro Pro Leu Gln Lys Pro Pro Gly Pro Pro His Asn Phe Ser
            340                 345                 350
Leu Gln Leu Gln Asn Gln Gly Gln His Ser Leu Gly Pro Gly Leu
            355                 360                 365
Phe Gly Gln Asn Val Pro Ser Met Gln Leu Pro Gly Gln Leu Pro Thr
        370                 375                 380
Ser Gln Pro Leu Thr Gln Gln Asn Ala Ser Ala Gly Ala Leu Gln Val
385                 390                 395                 400
Pro Pro Ala Ile Gln Ser Asn Pro Met Gln Ser Val Pro Gly Gln Gln
                405                 410                 415
Gln Leu Pro Ser Asn Val Ala Ala Gln Met Met Gln Gln Pro Ile Gln
            420                 425                 430
Gln Ile Pro Ser Gln Ala Pro Gln Leu Leu Leu Gln Gln Gln Ala Ala
            435                 440                 445
Met Gln Ser Ser Tyr Gln Ser Ser Gln Gln Ala Ile Phe Gln Leu Gln
        450                 455                 460
Gln Gln Leu Gln Leu Met Gln Gln Gln Gln Gln Gln Gln Gln Gln Pro
465                 470                 475                 480
Asn Leu Asn Gln Gln Pro His Thr Gln Ile Ser Lys Gln Gln Gly Gln
                485                 490                 495
Pro Asn Gln Ser Ser Thr Pro Gly Ala Pro Ala Met Met Pro Ser
            500                 505                 510
Asn Ile Asn Ala Ile Pro Gln Gln Val Asn Ser Pro Val Val Ser Leu
            515                 520                 525
Thr Cys Asn Trp Thr Glu His Thr Ser Pro Gly Phe Lys Tyr Tyr
        530                 535                 540
Tyr Asn Ser Ile Thr Arg Glu Ser Lys Trp Glu Lys Pro Glu Glu Tyr
545                 550                 555                 560
Val Leu Tyr Glu Gln Gln Gln Gln Gln His Gln Lys Leu Ile Leu
                565                 570                 575
Leu Gln Gln His Gln Gln Lys Leu Val Ala Gln Leu Gln Ser Pro
            580                 585                 590
Pro Gln Ala Gln Thr Ile Gln Ser Met Gln Ser Ile Gln Gln His Pro
            595                 600                 605
Gln Ser His Gln Gly His Asn Gln Met Gln Met Lys His Gln Glu Leu
        610                 615                 620
Asn Tyr Asn Gln Leu Gln Ala Thr Gly Asn Ile Asp Pro Asn Arg Ile
625                 630                 635                 640
Gln Gln Gly Ile Gln Ala Ala Gln Glu Arg Ser Trp Lys Ser
                645                 650
```

```
<210> SEQ ID NO 25
<211> LENGTH: 618
<212> TYPE: PRT
<213> ORGANISM: Lolium perenne

<400> SEQUENCE: 25

Gly Gly Arg Gly Asp Tyr Ser Asp His Asp Asn Lys Ser Gly His Val
  1               5                  10                  15

Lys Leu Phe Val Gly Ser Val Pro Arg Thr Ala Ser Glu Asp Asp Val
             20                  25                  30

Arg Pro Leu Phe Glu Asn His Gly Asp Val Leu Glu Val Ala Met Ile
         35                  40                  45

Arg Asp Arg Lys Thr Gly Glu Gln Gln Gly Cys Cys Phe Val Lys Tyr
 50                  55                  60

Ala Thr Ser Glu Glu Ala Glu Arg Ala Ile Arg Ala Leu His Asn Gln
 65                  70                  75                  80

Trp Thr Ile Pro Gly Ala Met Gly Pro Val Gln Val Arg Tyr Ala Asp
                 85                  90                  95

Gly Glu Lys Glu Arg His Gly Ser Ile Glu His Lys Leu Phe Val Ala
            100                 105                 110

Ser Leu Asn Lys Gln Ala Thr Ala Lys Glu Ile Glu Glu Ile Phe Ala
        115                 120                 125

Pro Phe Gly His Val Glu Asp Val Tyr Ile Met Lys Asp Gly Met Lys
130                 135                 140

Gln Ser Arg Gly Cys Gly Phe Val Lys Phe Ser Ser Lys Glu Pro Ala
145                 150                 155                 160

Leu Ala Ala Met Asn Ser Leu Ser Gly Thr Tyr Ile Met Arg Arg Pro
                165                 170                 175

Arg Pro Gly Glu Ser Arg Gly Pro Ala Phe Gly Gly Pro Gly Val
            180                 185                 190

Ser Pro Arg Ser Asp Ala Ala Leu Val Ile Arg Pro Thr Ala Asn Leu
        195                 200                 205

Asp Glu Pro Arg Gly Arg His Met Pro Arg Asp Ala Trp Arg Pro Ser
210                 215                 220

Ser Pro Ser Ser Val Ala Ser His Gln Phe Asn Asn Tyr Gly Ser Asp
225                 230                 235                 240

Asn Pro Met Gly Ile Met Gly Gly Thr Gly Thr Ser Ala Ala Asp Asn
                245                 250                 255

Gly Ala Phe Arg Pro Gln Met Phe Pro Gly Asn Gly Gln Thr Ala Val
            260                 265                 270

Pro Thr Ser Ser His Met Gly Ile Asn Thr Ser Leu Gln Gly His His
        275                 280                 285

Leu Gly Gly Gln Gln Ile Pro Pro Leu Gln Lys Pro Pro Gly Pro Pro
290                 295                 300

His Asn Phe Ser Leu Gln Leu Gln Asn Gln Gln Gly Gln His Ser Leu
305                 310                 315                 320

Val Pro Gly Leu Phe Gly Gln Asn Val Pro Ser Met Gln Leu Pro Gly
                325                 330                 335

Gln Leu Pro Thr Ser Gln Pro Leu Thr Gln Asn Ala Ser Ala Gly
            340                 345                 350

Ala Leu Gln Ala Pro Ala Ile Gln Ser Asn Pro Met Gln Ser Val
        355                 360                 365

Pro Gly Gln Gln Gln Leu Pro Ser Asn Val Ala Pro Gln Met Met Gln
```

```
                370             375             380
Gln Pro Ile Gln Gln Ile Pro Ser Gln Ala Pro Gln Leu Leu Gln
385                 390                 395                 400

Gln Gln Ala Ala Met Gln Ser Ser Tyr Gln Ser Ser Gln Gln Ala Ile
                405                 410                 415

Phe Gln Leu Gln Gln Gln Leu Gln Leu Met Gln Gln Gln Gln Gln Gln
                420                 425                 430

Gln Gln Gln Pro Asn Leu Asn Gln Gln Pro Asn Leu Asn Gln Gln
            435                 440                 445

Gln His Thr Gln Ile Ser Lys Gln Gln Gly Gln Pro Asn Gln Ser Ser
            450                 455                 460

Thr Pro Gly Ala Pro Ala Ala Met Met Pro Ser Asn Ile Asn Ala Ile
465                 470                 475                 480

Pro Gln Gln Val Asn Ser Pro Ala Val Ser Leu Thr Cys Asn Trp Thr
                485                 490                 495

Glu His Thr Ser Pro Glu Gly Phe Lys Tyr Tyr Tyr Asn Ser Ile Thr
                500                 505                 510

Arg Glu Ser Lys Trp Glu Lys Pro Glu Glu Tyr Val Leu Tyr Glu Gln
                515                 520                 525

Gln Gln Gln Gln Gln Gln Gln Lys Leu Ile Leu Leu Gln Gln His
            530                 535                 540

Gln Gln Lys Leu Val Ala Gln Gln Leu Gln Ser Pro Pro Gln Ala Gln
545                 550                 555                 560

Thr Ile Gln Ser Met Gln Ser Ile Gln Gln His Pro Gln Ser His Gln
                565                 570                 575

Gly His Asn Gln Met Gln Met Lys His Gln Glu Leu Asn Tyr Asn Gln
                580                 585                 590

Leu Gln Ala Thr Gly Asn Ile Asp Pro Asn Arg Ile Gln Gln Gly Ile
                595                 600                 605

Gln Ala Ala Gln Glu Arg Ser Trp Lys Ser
            610                 615

<210> SEQ ID NO 26
<211> LENGTH: 177
<212> TYPE: PRT
<213> ORGANISM: Festuca arundinacea

<400> SEQUENCE: 26

Met Ala Gly Arg Asp Arg Asp Pro Leu Val Val Gly Arg Val Val Gly
1               5                   10                  15

Asp Val Leu Asp Pro Phe Val Arg Thr Thr Asn Leu Arg Val Thr Phe
                20                  25                  30

Gly Asn Arg Ala Val Ser Asn Gly Cys Glu Leu Lys Pro Ser Met Val
            35                  40                  45

Thr His Gln Pro Arg Val Glu Val Gly Gly Asn Glu Met Arg Thr Phe
        50                  55                  60

Tyr Thr Leu Val Met Val Asp Pro Asp Ala Pro Ser Pro Ser Asp Pro
65                  70                  75                  80

Asn Leu Arg Glu Tyr Leu His Trp Leu Val Thr Asp Ile Pro Gly Thr
                85                  90                  95

Thr Gly Ala Ser Phe Gly Gln Glu Val Met Cys Tyr Glu Ser Pro Arg
            100                 105                 110

Pro Asn Met Gly Ile His Arg Phe Val Leu Val Leu Phe Gln Gln Leu
        115                 120                 125
```

```
Gly Arg Gln Thr Val Tyr Ala Pro Gly Trp Arg Gln Asn Phe Asn Thr
        130                 135                 140

Arg Asp Phe Ala Glu Leu Tyr Asn Leu Gly Pro Ala Val Ala Ala Val
145                 150                 155                 160

Tyr Phe Asn Cys Gln Arg Glu Ala Gly Ser Gly Gly Arg Arg Met Tyr
                165                 170                 175

Asn

<210> SEQ ID NO 27
<211> LENGTH: 89
<212> TYPE: PRT
<213> ORGANISM: Lolium perenne

<400> SEQUENCE: 27

Met Val Gly Val Gln Arg Ala Asp Pro Leu Val Gly Arg Val Ile
  1               5                  10                  15

Gly Asp Val Val Asp Pro Phe Val Arg Arg Val Pro Leu Arg Val Gly
                 20                  25                  30

Tyr Ala Ser Arg Asp Val Ala Asn Gly Cys Glu Leu Arg Pro Ser Ala
             35                  40                  45

Ile Ala Asp Gln Pro Arg Val Glu Val Gly Gly Pro Asp Met Arg Thr
 50                  55                  60

Phe Tyr Thr Leu Val Met Val Asp Pro Asp Ala Pro Ser Pro Ser Asp
 65                  70                  75                  80

Pro Ser Leu Arg Glu Tyr Leu His Trp
                 85

<210> SEQ ID NO 28
<211> LENGTH: 298
<212> TYPE: PRT
<213> ORGANISM: Lolium perenne

<400> SEQUENCE: 28

Glu Ala Phe Ala Gly Cys Arg Arg Val His Val Val Asp Phe Gly Ile
  1               5                  10                  15

Lys Gln Gly Met Gln Trp Pro Ala Leu Leu Gln Ala Leu Ala Leu Arg
                 20                  25                  30

Pro Gly Gly Pro Pro Ser Phe Arg Leu Thr Gly Val Gly Pro Pro Gln
             35                  40                  45

Pro Asp Glu Thr Asp Ala Leu Gln Gln Val Gly Trp Lys Leu Ala Gln
 50                  55                  60

Phe Ala His Thr Ile Gly Val Asp Phe Gln Tyr Arg Gly Leu Val Ala
 65                  70                  75                  80

Ala Thr Leu Ala Asp Leu Glu Pro Phe Met Leu Gln Pro Glu Ala Asp
                 85                  90                  95

Asp Gly Pro Asn Glu Glu Pro Glu Val Ile Ala Val Asn Ser Val Phe
            100                 105                 110

Glu Met His Arg Leu Leu Ala Gln Pro Gly Ala Leu Glu Lys Val Leu
        115                 120                 125

Gly Thr Val Arg Ala Val Arg Pro Arg Ile Val Thr Val Val Glu Gln
    130                 135                 140

Glu Ala Asn His Asn Thr Gly Ser Phe Leu Asp Arg Phe Thr Glu Ser
145                 150                 155                 160

Leu His Tyr Tyr Ser Thr Met Phe Asp Ser Leu Glu Gly Ala Gly Ser
                165                 170                 175

Ala Pro Ser Glu Ile Ser Ser Gly Pro Ser Ala Ala Ala Ala Asn Ala
```

```
                    180                 185                 190
Ala Ala Pro Gly Thr Asp Gln Val Met Ser Glu Val Tyr Leu Gly Arg
        195                 200                 205
Gln Ile Cys Asn Val Val Ala Cys Glu Gly Ala Glu Arg Thr Glu Arg
        210                 215                 220
His Glu Thr Leu Gly Gln Trp Arg Gly Arg Leu Gly His Ala Gly Phe
225                 230                 235                 240
Glu Thr Val His Leu Gly Ser Asn Ala Tyr Lys Gln Ala Ser Thr Leu
                245                 250                 255
Leu Ala Leu Phe Ala Gly Gly Asp Gly Tyr Lys Val Asp Glu Lys Glu
        260                 265                 270
Gly Cys Leu Thr Leu Gly Trp His Thr Arg Pro Leu Ile Ala Thr Ser
        275                 280                 285
Ala Trp Arg Met Ala Ala Ala Ala Pro
        290                 295

<210> SEQ ID NO 29
<211> LENGTH: 1148
<212> TYPE: PRT
<213> ORGANISM: Lolium perenne

<400> SEQUENCE: 29

Met Ser Val Ser Asn Gly Lys Trp Ile Asp Gly Leu Gln Phe Ser Ser
1               5                   10                  15
Leu Phe Trp Pro Pro His Asp Ala Gln Gln Lys Gln Ala Gln Thr
            20                  25                  30
Leu Ala Tyr Val Glu Tyr Phe Gly Gln Phe Thr Ser Asp Ser Glu Gln
        35                  40                  45
Phe Pro Glu Asp Val Ala Gln Leu Ile Gln Ser Tyr Tyr Pro Ser Lys
    50                  55                  60
Glu Lys Arg Leu Val Asp Glu Val Leu Ala Thr Phe Val Leu His His
65                  70                  75                  80
Pro Glu His Gly His Ala Val Val His Pro Ile Leu Ser Arg Ile Ile
                85                  90                  95
Asp Gly Ser Leu Ser Tyr Asp Arg His Gly Ser Pro Phe Asn Ser Phe
            100                 105                 110
Ile Ser Leu Phe Thr Gln Thr Ala Glu Lys Glu Tyr Ser Glu Gln Trp
        115                 120                 125
Ala Leu Ala Cys Gly Glu Ile Leu Arg Val Leu Thr His Tyr Asn Arg
    130                 135                 140
Pro Ile Phe Lys Val Ala Glu Cys Asn Asp Thr Ser Asp Gln Ala Thr
145                 150                 155                 160
Thr Ser Tyr Ser Leu His Asp Lys Ala Asn Ser Ser Pro Glu Asn Glu
                165                 170                 175
Pro Glu Arg Lys Pro Leu Arg Pro Leu Ser Pro Trp Ile Thr Asp Ile
            180                 185                 190
Leu Leu Asn Ala Pro Leu Gly Ile Arg Ser Asp Tyr Phe Arg Trp Cys
        195                 200                 205
Gly Gly Val Met Gly Lys Tyr Ala Ala Gly Glu Leu Lys Pro Pro
    210                 215                 220
Thr Thr Ala Tyr Ser Arg Gly Ala Gly Lys His Pro Gln Leu Met Pro
225                 230                 235                 240
Ser Thr Pro Arg Trp Ala Val Ala Asn Gly Ala Gly Val Ile Leu Ser
                245                 250                 255
```

-continued

```
Val Cys Asp Glu Glu Val Ala Arg Tyr Glu Thr Ala Asn Leu Thr Ala
            260                 265                 270

Ala Ala Val Pro Ala Leu Leu Pro Pro Thr Thr Pro Leu Asp
        275                 280             285

Glu His Leu Val Ala Gly Leu Pro Pro Leu Pro Tyr Ala Arg Leu
        290                 295                 300

Phe His Arg Tyr Tyr Ala Ile Ala Thr Pro Ser Ala Thr Gln Arg Leu
305                 310                 315                 320

Leu Phe Gly Leu Leu Glu Ala Pro Pro Ser Trp Ala Pro Asp Ala Leu
                325                 330                 335

Asp Ala Ala Val Gln Leu Val Glu Leu Leu Arg Ala Ala Glu Asp Tyr
                340                 345                 350

Ala Thr Gly Met Arg Leu Pro Lys Asn Trp Leu His Leu His Phe Leu
                355                 360                 365

Arg Ala Ile Gly Thr Ala Met Ser Met Arg Ala Gly Met Ala Ala Asp
370                 375                 380

Thr Ala Ala Leu Leu Phe Arg Ile Leu Ser Gln Pro Thr Leu Leu
385                 390                 395                 400

Phe Pro Pro Leu Arg His Ala Glu Gly Val Val Gln His Glu Pro Leu
                405                 410                 415

Gly Gly Tyr Val Ser Ser Tyr Lys Arg Gln Leu Glu Ile Pro Ala Ser
                420                 425                 430

Glu Thr Thr Ile Asp Ala Thr Ala Gln Gly Ile Ala Ser Leu Leu Cys
                435                 440                 445

Ala His Gly Pro Asp Val Glu Trp Arg Ile Cys Thr Ile Trp Glu Ala
            450                 455                 460

Ala Tyr Gly Leu Leu Pro Leu Asn Ser Ser Ala Val Asp Leu Pro Glu
465                 470                 475                 480

Ile Val Val Ala Ala Pro Leu Gln Pro Pro Thr Leu Ser Trp Ser Leu
                485                 490                 495

Tyr Leu Pro Leu Leu Lys Val Phe Glu Tyr Leu Pro Arg Gly Ser Pro
                500                 505                 510

Ser Glu Ala Cys Leu Met Arg Ile Phe Val Ala Thr Val Glu Ala Ile
            515                 520                 525

Leu Arg Arg Thr Phe Pro Ser Glu Thr Glu Pro Ser Lys Lys Pro Arg
            530                 535                 540

Ser Pro Ser Lys Ser Leu Ala Val Ala Glu Leu Arg Thr Met Ile His
545                 550                 555                 560

Ser Leu Phe Val Glu Ser Cys Ala Ser Met Asn Leu Ala Ser Arg Leu
                565                 570                 575

Leu Phe Val Leu Thr Val Ser Val Ser His Gln Ala Leu Pro Gly
                580                 585                 590

Gly Ser Lys Arg Pro Thr Gly Ser Glu Asn His Ser Ser Glu Glu Ser
            595                 600                 605

Thr Glu Asp Ser Lys Leu Thr Asn Gly Arg Asn Arg Cys Lys Lys Lys
            610                 615                 620

Gln Gly Pro Val Gly Thr Phe Asp Ser Tyr Val Leu Ala Ala Val Cys
625                 630                 635                 640

Ala Leu Ser Cys Glu Leu Gln Leu Phe Pro Ile Leu Cys Lys Asn Val
                645                 650                 655

Thr Lys Thr Asn Ile Lys Asp Ser Ile Lys Ile Thr Met Pro Gly Lys
                660                 665                 670

Thr Asn Gly Ile Ser Asn Glu Leu His Asn Ser Val Asn Ser Ala Ile
```

-continued

```
                675                 680                 685
Leu His Thr Arg Arg Ile Leu Gly Ile Leu Glu Ala Leu Phe Ser Leu
690                 695                 700
Lys Pro Ser Ser Val Gly Thr Ser Trp Ser Tyr Ser Ser Asn Glu Ile
705                 710                 715                 720
Val Ala Ala Ala Met Val Ala Ala His Val Ser Glu Leu Phe Arg Arg
                725                 730                 735
Ser Arg Pro Cys Leu Asn Ala Leu Ser Ala Leu Lys Arg Cys Lys Trp
                740                 745                 750
Asp Ala Glu Ile Ser Thr Arg Ala Ser Ser Leu Tyr His Leu Ile Asp
                755                 760                 765
Leu His Gly Lys Thr Val Ser Ser Ile Val Asn Lys Ala Glu Pro Leu
770                 775                 780
Glu Ala His Leu Asn Leu Thr Ala Val Lys Lys Asp Asp Gln His His
785                 790                 795                 800
Ile Glu Glu Ser Asn Thr Ser Ser Ser Asp Tyr Gly Asn Leu Glu Lys
                805                 810                 815
Lys Ser Lys Lys Asn Gly Phe Ser Arg Pro Leu Met Lys Cys Ala Glu
                820                 825                 830
Gln Ala Arg Arg Asn Gly Asn Val Ala Ser Thr Ser Gly Lys Ala Thr
                835                 840                 845
Ala Thr Leu Gln Ala Glu Ala Ser Asp Leu Ala Asn Phe Leu Thr Met
                850                 855                 860
Asp Arg Asn Gly Gly Tyr Gly Gly Ser Gln Thr Leu Leu Arg Thr Val
865                 870                 875                 880
Met Ser Glu Lys Gln Glu Leu Cys Phe Ser Val Val Ser Leu Leu Trp
                885                 890                 895
His Lys Leu Ile Ala Ser Pro Glu Thr Gln Met Ser Ala Glu Ser Thr
                900                 905                 910
Ser Ala His Gln Gly Trp Arg Lys Val Ala Asp Ala Leu Cys Asp Val
                915                 920                 925
Val Ser Ala Ser Pro Ala Lys Ala Ser Thr Ala Ile Val Leu Gln Ala
                930                 935                 940
Glu Lys Asp Leu Gln Pro Trp Ile Ala Arg Asp Asp Glu Gln Gly Gln
945                 950                 955                 960
Lys Met Trp Arg Val Asn Gln Arg Ile Val Lys Leu Ile Ala Glu Leu
                965                 970                 975
Met Arg Asn His Asp Ser Pro Glu Ala Leu Ile Ile Leu Ala Ser Ala
                980                 985                 990
Ser Asp Leu Leu Leu Arg Ala Thr Asp Gly Met Leu Val Asp Gly Glu
                995                 1000                1005
Ala Cys Thr Leu Pro Gln Leu Glu Leu Leu Glu Val Thr Ala Arg Ala
                1010                1015                1020
Ile His Leu Ile Val Glu Trp Gly Asp Pro Gly Val Ala Val Ala Asp
1025                1030                1035                1040
Gly Leu Ser Asn Leu Leu Lys Cys Arg Leu Ser Pro Thr Ile Arg Cys
                1045                1050                1055
Leu Ser His Pro Ser Ala His Val Arg Ala Leu Ser Met Ser Val Leu
                1060                1065                1070
Arg Asp Ile Leu Asn Ser Gly Pro Ile Ser Ser Thr Lys Ile Ile Gln
                1075                1080                1085
Gly Glu Gln Arg Asn Gly Ile Gln Ser Pro Ser Tyr Arg Cys Ala Ala
                1090                1095                1100
```

```
Ala Ser Met Thr Asn Trp Gln Ala Asp Val Glu Arg Cys Ile Glu Trp
1105                1110                1115                1120

Glu Ala His Asn Arg Gln Ala Thr Gly Met Thr Leu Ala Phe Leu Thr
            1125                1130                1135

Ala Ala Ala Asn Glu Leu Gly Cys Pro Leu Pro Cys
        1140                1145
```

<210> SEQ ID NO 30
<211> LENGTH: 1149
<212> TYPE: PRT
<213> ORGANISM: Festuca arundinacea

<400> SEQUENCE: 30

```
Met Ser Ala Ser Asn Gly Lys Trp Ile Asp Gly Leu Gln Phe Ser Ser
1               5                   10                  15

Leu Phe Trp Pro Pro His Asp Ala Gln Gln Lys Gln Ala Gln Thr
            20                  25                  30

Leu Ala Tyr Val Glu Tyr Phe Gly Gln Phe Thr Ser Asp Ser Glu Gln
        35                  40                  45

Phe Pro Glu Asp Val Ala Gln Leu Ile Gln Ser Cys Tyr Pro Ser Lys
    50                  55                  60

Glu Lys Arg Leu Val Asp Glu Val Leu Ala Thr Phe Val Leu His His
65                  70                  75                  80

Pro Glu His Gly His Ala Val Val His Pro Ile Leu Ser Arg Ile Ile
                85                  90                  95

Asp Gly Ser Leu Ser Tyr Asp Arg His Gly Ser Pro Phe Asn Ser Phe
            100                 105                 110

Ile Ser Leu Phe Thr Gln Thr Ala Glu Lys Glu Tyr Ser Glu Gln Trp
        115                 120                 125

Ala Leu Ala Cys Gly Glu Ile Leu Arg Val Leu Thr His Tyr Asn Arg
    130                 135                 140

Pro Ile Phe Lys Val Ala Glu Cys Asn Asp Thr Ser Asp Gln Ala Thr
145                 150                 155                 160

Thr Ser Tyr Ser Leu Gln Glu Lys Ala Asn Ser Ser Pro Glu Asn Glu
                165                 170                 175

Pro Glu Arg Lys Pro Leu Arg Pro Leu Ser Pro Trp Ile Thr Asp Ile
            180                 185                 190

Leu Leu Asn Ala Pro Leu Gly Ile Arg Ser Asp Tyr Phe Arg Trp Cys
        195                 200                 205

Gly Gly Val Met Gly Lys Tyr Ala Ala Gly Gly Glu Leu Lys Pro Pro
    210                 215                 220

Thr Thr Ala Tyr Ser Arg Gly Ala Gly Lys His Pro Gln Leu Met Pro
225                 230                 235                 240

Ser Thr Pro Arg Trp Ala Val Ala Asn Gly Ala Gly Val Ile Leu Ser
                245                 250                 255

Val Cys Asp Glu Glu Val Ala Arg Tyr Glu Thr Ala Asn Leu Thr Ala
            260                 265                 270

Ala Ala Val Pro Ala Leu Leu Pro Pro Thr Thr Pro Leu Asp
        275                 280                 285

Glu His Leu Val Ala Gly Leu Pro Pro Leu Pro Tyr Ala Arg Leu
    290                 295                 300

Phe His Arg Tyr Tyr Ala Ile Ala Thr Pro Ser Ala Thr Gln Arg Leu
305                 310                 315                 320

Leu Phe Gly Leu Leu Glu Ala Pro Pro Ser Trp Ala Pro Asp Ala Leu
```

```
                    325                 330                 335
Asp Ala Ala Val Gln Leu Val Glu Leu Leu Arg Ala Ala Glu Asp Tyr
                340                 345                 350
Ala Thr Gly Met Arg Leu Pro Lys Asn Trp Leu His Leu His Phe Leu
            355                 360                 365
Arg Ala Ile Gly Thr Ala Met Ser Met Arg Ala Gly Met Ala Ala Asp
        370                 375                 380
Thr Ala Ala Ala Leu Leu Phe Arg Ile Leu Ser Gln Pro Thr Leu Leu
385                 390                 395                 400
Phe Pro Pro Leu Arg His Ala Glu Gly Val Val Gln His Glu Pro Leu
                405                 410                 415
Gly Gly Tyr Val Ser Ser Tyr Lys Arg Gln Leu Glu Ile Pro Ala Ser
            420                 425                 430
Glu Thr Thr Ile Asp Ala Thr Ala Gln Gly Ile Ala Ser Leu Leu Cys
        435                 440                 445
Ala His Gly Pro Asp Val Glu Trp Arg Ile Cys Thr Ile Trp Glu Ala
    450                 455                 460
Ala Tyr Gly Leu Leu Pro Leu Asn Ser Ser Ala Val Asp Leu Pro Glu
465                 470                 475                 480
Ile Val Val Ala Ala Pro Leu Gln Pro Pro Thr Leu Ser Trp Ser Leu
                485                 490                 495
Tyr Leu Pro Leu Leu Lys Val Phe Glu Tyr Leu Pro Arg Gly Ser Pro
            500                 505                 510
Ser Glu Ala Cys Leu Met Arg Ile Phe Val Ala Thr Val Glu Ala Ile
        515                 520                 525
Leu Arg Arg Thr Phe Pro Ser Glu Thr Ser Glu Pro Ser Lys Lys Pro
    530                 535                 540
Arg Ser Pro Ser Lys Ser Leu Ala Val Ala Glu Leu Arg Thr Met Ile
545                 550                 555                 560
His Ser Leu Phe Val Glu Ser Cys Ala Ser Met Asn Leu Ala Ser Arg
                565                 570                 575
Leu Leu Phe Val Val Leu Thr Val Ser Val Ser His Gln Ala Leu Pro
            580                 585                 590
Gly Gly Ser Lys Arg Pro Thr Gly Ser Asp Asn His Ser Ser Glu Glu
        595                 600                 605
Ser Thr Glu Asp Ser Lys Leu Thr Asn Gly Arg Asn Arg Cys Lys Lys
    610                 615                 620
Lys Gln Gly Pro Val Gly Thr Phe Asp Ser Tyr Val Leu Ala Ala Val
625                 630                 635                 640
Cys Ala Leu Ser Cys Glu Leu Gln Leu Phe Pro Ile Leu Cys Lys Asn
                645                 650                 655
Val Thr Lys Ser Asn Ile Lys Asp Ser Ile Lys Ile Thr Met Pro Gly
            660                 665                 670
Lys Thr Asn Gly Ile Ser Asn Glu Leu His Asn Ser Val Asn Ser Ala
        675                 680                 685
Val Leu His Thr Arg Arg Ile Leu Gly Ile Leu Glu Ala Leu Phe Ser
    690                 695                 700
Leu Lys Pro Ser Ser Val Gly Thr Ser Trp Ser Tyr Ser Ser Asn Glu
705                 710                 715                 720
Ile Val Ala Ala Ala Met Val Ala Ala His Val Ser Glu Leu Phe Arg
                725                 730                 735
Arg Ser Arg Pro Cys Leu Asn Ala Leu Ser Ala Leu Lys Arg Cys Lys
            740                 745                 750
```

```
Trp Asp Ala Glu Ile Ser Thr Arg Ala Ser Ser Leu Tyr His Leu Ile
            755                 760                 765

Asp Leu His Gly Lys Thr Val Ser Ser Ile Val Asn Lys Ala Glu Pro
        770                 775                 780

Leu Glu Ala His Leu Asn Leu Thr Ala Val Lys Lys Asp Asp Gln His
785                 790                 795                 800

His Ile Glu Glu Ser Asn Thr Ser Ser Ser Asp Tyr Gly Asn Leu Glu
                805                 810                 815

Lys Lys Ser Lys Lys Asn Gly Phe Ser Arg Pro Leu Met Lys Cys Ala
            820                 825                 830

Glu Gln Ala Arg Arg Asn Gly Asn Val Ala Ser Thr Ser Gly Lys Ala
            835                 840                 845

Thr Ala Thr Leu Gln Ala Glu Ala Ser Asp Leu Ala Asn Phe Leu Thr
            850                 855                 860

Met Asp Arg Asn Gly Gly Tyr Gly Gly Ser Gln Thr Leu Leu Arg Thr
865                 870                 875                 880

Val Met Ser Glu Lys Gln Glu Leu Cys Phe Ser Val Val Ser Leu Leu
            885                 890                 895

Trp His Lys Leu Ile Ala Ser Pro Glu Thr Gln Met Ser Ala Glu Ser
            900                 905                 910

Thr Ser Ala His Gln Gly Trp Arg Lys Val Ala Asp Ala Leu Cys Asp
            915                 920                 925

Val Val Ser Ala Ser Pro Ala Lys Ala Ser Thr Ala Ile Val Leu Gln
            930                 935                 940

Ala Glu Lys Asp Leu Gln Pro Trp Ile Ala Arg Asp Asp Glu Gln Gly
945                 950                 955                 960

Gln Lys Met Trp Arg Val Asn Gln Arg Ile Val Lys Leu Ile Ala Glu
            965                 970                 975

Leu Met Arg Asn His Asp Ser Pro Glu Ala Leu Ile Ile Leu Ala Ser
            980                 985                 990

Ala Ser Asp Leu Leu Leu Arg Ala Thr Asp Gly Met Leu Val Asp Gly
            995                 1000                1005

Glu Ala Cys Thr Leu Pro Gln Leu Glu Leu Leu Glu Val Thr Ala Arg
    1010                1015                1020

Ala Ile His Leu Ile Val Glu Trp Gly Asp Pro Gly Val Ala Val Ala
    1025                1030                1035                1040

Asp Gly Leu Ser Asn Leu Leu Lys Cys Arg Leu Ser Pro Thr Ile Arg
                1045                1050                1055

Cys Leu Ser His Pro Ser Ala His Val Arg Ala Leu Ser Met Ser Val
                1060                1065                1070

Leu Arg Asp Ile Leu Asn Ser Gly Pro Ile Ser Ser Thr Lys Ile Asn
                1075                1080                1085

Gln Gly Glu Gln Arg Asn Gly Ile Gln Ser Pro Ser Tyr Arg Cys Met
                1090                1095                1100

Ala Ala Ser Met Thr Asn Trp Gln Ala Asp Val Glu Arg Cys Ile Glu
1105                1110                1115                1120

Trp Glu Ala His Asn Arg Gln Ala Thr Gly Met Thr Leu Ala Phe Leu
                1125                1130                1135

Thr Ala Ala Ala Asn Glu Leu Gly Cys Pro Leu Pro Cys
                1140                1145

<210> SEQ ID NO 31
<211> LENGTH: 496
```

```
<212> TYPE: PRT
<213> ORGANISM: Festuca arundinacea

<400> SEQUENCE: 31

Met Leu Ser Thr Ser Tyr Ala Leu Thr Ala Ala Pro Ile Pro Glu Gly
  1               5                  10                  15

Ala Ala Gly Pro Pro Asp Pro Phe Arg Pro Met Gln Ile Ala Asn Asp
             20                  25                  30

Asn Ala Ser Ala Lys Arg Lys Arg Pro Ala Gly Thr Pro Asp Pro
         35                  40                  45

Asp Ala Glu Val Val Ser Leu Ser Pro Arg Thr Leu Leu Glu Ser Asp
 50                  55                  60

Arg Tyr Val Cys Glu Ile Cys Asn Gln Gly Phe Gln Arg Asp Gln Asn
 65                  70                  75                  80

Leu Gln Met His Arg Arg His Lys Val Pro Trp Lys Leu Leu Lys
                 85                  90                  95

Arg Glu Ala Gly Glu Ala Ala Arg Lys Arg Val Phe Val Cys Pro Glu
            100                 105                 110

Pro Thr Cys Leu His His Asp Pro Ala His Ala Leu Gly Asp Leu Val
        115                 120                 125

Gly Ile Lys Lys His Phe Arg Arg Lys His Ser Gly His Arg Gln Trp
130                 135                 140

Ala Cys Ser Arg Cys Ser Lys Ala Tyr Ala Val His Ser Asp Tyr Lys
145                 150                 155                 160

Ala His Leu Lys Thr Cys Gly Thr Arg Gly His Thr Cys Asp Cys Gly
                165                 170                 175

Arg Val Phe Ser Arg Val Glu Ser Phe Ile Glu His Gln Asp Met Cys
            180                 185                 190

Asp Ala Ser Arg Pro Arg Gly Gly Thr Thr Ser Ser Ser Pro Gly His
        195                 200                 205

Gly Gly Gly Arg Val Val Gly Ala Ser Asn Pro Gln His Leu Leu His
210                 215                 220

Ala Ala Ser Leu Ser Arg Thr Ala Ser Ser Ala Ser Pro Ser Ser Gly
225                 230                 235                 240

Gly Glu Leu Val Gly Ser Pro Val Ala Trp Pro Cys Gly Pro Ala Thr
                245                 250                 255

Ala Ser Pro Thr Ala Ala Asn Val Ala Ala Phe Gln Arg Leu Leu Asp
            260                 265                 270

Pro Thr Gln Ser Ser Pro Pro Thr Pro Ser Asp Arg Arg Gly Ala
        275                 280                 285

Gly Thr Gln Asn Leu Glu Leu Gln Leu Met Pro Pro Arg Gly Gly Gly
    290                 295                 300

Ala Ala Pro Pro Gly Thr Ala Leu Thr Tyr Arg Ala Ser Pro Cys Ser
305                 310                 315                 320

Pro Ser Val Leu His Ala Pro Arg Gln Leu Gly Ala Asp Ala Val Arg
                325                 330                 335

Leu Gln Leu Ser Ile Gly Cys Gly Gly Ala Pro Asp Asp Ser Ser Val
            340                 345                 350

Glu Ser Ala Pro Ala Pro Ala Ala Thr Leu Lys Glu Glu Ala Arg Glu
        355                 360                 365

Gln Leu Arg Leu Ala Thr Ala Glu Met Ala Ser Ala Glu Glu Thr Arg
    370                 375                 380

Ala Gln Ala Arg Arg Gln Val Glu Leu Ala Glu Gln Glu Leu Ala Gly
385                 390                 395                 400
```

-continued

Ala Arg Arg Val Arg Gln Gln Ala Gln Leu Glu Leu Gly Arg Ala His
            405                 410                 415

Ala Leu Arg Asp His Ala Val Arg Gln Ile Asp Ala Thr Leu Met Glu
            420                 425                 430

Ile Thr Cys Tyr Gly Cys Arg His Asn Phe Arg Ala Arg Ala Ala Ala
            435                 440                 445

Met Asn Cys Glu Val Ala Ser Tyr Val Ser Ser Val Leu Thr Glu Gly
            450                 455                 460

Gly Asp Ala Glu Val Asp Asn Asp Gly His His Gln Leu Leu His Ala
465                 470                 475                 480

Gly Asp Leu Pro Arg Ser His Arg Ala Met Met Lys Met Asp Leu Asn
                485                 490                 495

<210> SEQ ID NO 32
<211> LENGTH: 530
<212> TYPE: PRT
<213> ORGANISM: Lolium perenne

<400> SEQUENCE: 32

Met Ala Ala Ala Ser Ser Ala Pro Phe Phe Gly Leu Ser Asp Ala Gln
 1               5                  10                  15

Met Gln Pro Met Val Pro Ala Gln Pro Pro Ala Pro Val Ala Ala Ala
            20                  25                  30

Pro Ala Pro Lys Lys Lys Arg Asn Gln Pro Gly Asn Pro Asn Pro Asp
            35                  40                  45

Ala Glu Val Ile Ala Leu Ser Pro Arg Ser Leu Met Ala Thr Asn Arg
 50                  55                  60

Phe Val Cys Glu Val Cys Gly Lys Gly Phe Gln Arg Glu Gln Asn Leu
65                  70                  75                  80

Gln Leu His Arg Arg Gly His Asn Leu Pro Trp Lys Leu Lys Gln Lys
                85                  90                  95

Asn Pro Lys Asp Ala Leu Arg Arg Val Tyr Leu Cys Pro Glu Pro
            100                 105                 110

Thr Cys Val His His Asp Pro Ala Arg Ala Leu Gly Asp Leu Thr Gly
            115                 120                 125

Ile Lys Lys His Tyr Cys Arg Lys His Gly Glu Lys Lys Trp Lys Cys
            130                 135                 140

Asp Lys Cys Ala Lys Arg Tyr Ala Val Gln Ser Asp Trp Lys Ala His
145                 150                 155                 160

Ser Lys Thr Cys Gly Thr Arg Glu Tyr Arg Cys Asp Cys Gly Thr Leu
                165                 170                 175

Phe Ser Arg Arg Asp Ser Phe Ile Thr His Arg Ala Phe Cys Asp Ala
            180                 185                 190

Leu Ala Gln Glu Ser Ala Arg Leu Pro Ala Ile Gly Ala Ser Leu Tyr
            195                 200                 205

Gly Gly Val Gly Asn Met Gly Ala Leu Asn Thr Leu Ser Gly Met Pro
            210                 215                 220

Gln Gln Leu Pro Gly Gly Ser Phe Pro Asp Gln Ser Gly His His Ser
225                 230                 235                 240

Ser Ala Ser Ala Met Asp Ile His Asn Leu Gly Gly Gly Ser Asn Ala
                245                 250                 255

Gly Gln Phe Asp Gln His Leu Met Pro Gln Ser Ala Gly Ser Ser Met
            260                 265                 270

Phe Arg Ser Gln Ala Ala Ser Ser Ser Pro Tyr Tyr Leu Gly Ala Ala

```
                  275                 280                 285
Ala Ala Gln Asp Phe Ala Glu Asp Val His Arg Ser His Gly Asn
    290                 295                 300

Gln Ser Ser Leu Leu Gln Gly Lys Ser Thr Ala Ala Phe His Gly Leu
305                 310                 315                 320

Met Gln Leu Pro Asp Gln His Gln Gly Ser Ala Ser Asn Gly Asn Asn
                325                 330                 335

Asn Leu Leu Asn Leu Gly Phe Tyr Ser Gly Asn Gly Gly Gln Asp
            340                 345                 350

Gly Arg Val Met Phe Gln Asn Gln Phe Asn Ser Ser Ala Gly Asn Gly
            355                 360                 365

Asn Val Asn Ala Glu Asn Asn Gly Ser Leu Leu Gly Gly Gly Gly
    370                 375                 380

Gly Phe Pro Ser Leu Phe Gly Ser Ser Glu Ser Gly Gly Leu Pro
385                 390                 395                 400

Gln Met Ser Ala Thr Ala Leu Leu Gln Lys Ala Ala Gln Met Gly Ala
                405                 410                 415

Thr Thr Ser Ser His Asn Ala Ser Ala Gly Leu Met Arg Gly Pro Gly
            420                 425                 430

Met Arg Gly Gly Ala Gly Glu Gly Gly Ser Ser Ser Ala Ser Glu
            435                 440                 445

Arg Gln Ser Phe His Asp Leu Ile Met Asn Ser Leu Ala Asn Gly Ser
    450                 455                 460

Gly Ala Pro Ala Thr Thr Gly Gly Gly Thr Val Ala Phe Gly Gly Gly
465                 470                 475                 480

Gly Phe Pro Ile Asp Asp Gly Lys Leu Ser Thr Arg Asp Phe Leu Gly
                485                 490                 495

Val Gly Pro Gly Gly Val Val His Ala Gly Met Gly Pro Pro Arg Arg
            500                 505                 510

His Gly Gly Ala Ala Gly Leu His Ile Gly Ser Leu Asp Pro Ala Glu
            515                 520                 525

Leu Lys
    530

<210> SEQ ID NO 33
<211> LENGTH: 466
<212> TYPE: PRT
<213> ORGANISM: Festuca arundinacea

<400> SEQUENCE: 33

Met Pro Pro Asn Pro Thr Asp Pro Glu Gln Pro Glu Ala Ala Ala
1               5                   10                  15

Pro Ala Pro Pro Lys Lys Lys Arg Asn Leu Pro Gly Thr Pro Asp
            20                  25                  30

Pro Asp Ala Glu Val Ile Ala Leu Ser Pro Gly Thr Leu Met Ala Thr
        35                  40                  45

Asn Arg Phe Val Cys Glu Val Cys Gly Lys Gly Phe Gln Arg Asp Gln
    50                  55                  60

Asn Leu Gln Leu His Arg Arg Gly His Asn Leu Pro Trp Arg Leu Arg
65                  70                  75                  80

Gln Arg Gly Pro Gly Ala Ala Pro Pro Arg Arg Val Tyr Val Cys
                85                  90                  95

Pro Glu Pro Gly Cys Val His His Ala Pro Ala Arg Ala Leu Gly Asp
            100                 105                 110
```

```
Leu Thr Gly Ile Lys Lys His Phe Cys Arg Lys His Gly Glu Lys Arg
            115                 120                 125

Trp Ala Cys Pro Arg Cys Gly Lys Arg Tyr Ala Val Gln Ala Asp Leu
        130                 135                 140

Lys Ala His Ala Lys Thr Cys Gly Thr Arg Glu Tyr Arg Cys Asp Cys
145                 150                 155                 160

Gly Thr Leu Phe Thr Arg Arg Asp Ser Phe Val Thr His Arg Ala Phe
                165                 170                 175

Cys Gly Ala Leu Val Glu Glu Thr Gly Arg Val Leu Ala Val Pro Ala
                180                 185                 190

Pro Pro Ala Pro Gly Pro Pro Asp Leu Asp Asp Val Asp Glu Asn Phe
            195                 200                 205

Asp Lys Asp Ser Glu Lys Gly Glu Asn Val Glu Asp Glu Glu
210                 215                 220

Lys Gly Glu Val Asn Glu Asn Ser Ala Val Ala Asp Val Asn Glu Pro
225                 230                 235                 240

Gln Arg Val Glu Ala Ala Ser Glu Ala Pro Gln Arg Ile Pro Ser Pro
                245                 250                 255

Gln Gln Gln Arg Ile Pro Ser Pro Arg Ile Pro Ser Pro Gln Arg
            260                 265                 270

Ile Arg Ser Pro Pro Ser Pro Val Pro Gln Glu Gln Gln Gln Gln Pro
            275                 280                 285

Met Val Ala Val Pro Asn Leu Glu Gly Pro Lys Val Ala Ala Glu
            290                 295                 300

Pro Ile Val Val Val Lys Gln Glu Glu Asp Asp Lys Arg Asp Glu Asp
305                 310                 315                 320

Val Cys Phe Gln Glu Ala Asp Lys Tyr Asp Asp Ala Glu Leu Glu Gly
                325                 330                 335

Ser Ser Leu Pro Asp Thr Asp Thr Pro Met Leu Pro Cys Phe Leu Pro
                340                 345                 350

Ser Pro Ser Asp Ala Ile Gly Thr Asp Gly Ser Ser Thr Ser Cys Gly
            355                 360                 365

Thr Val Ser Ser Ala Ser Ile Pro Leu Arg Gln Gln Arg Arg Leu Ala
        370                 375                 380

His Leu Leu Gly Cys Leu His Arg Pro Arg Gln Ala Pro Leu Pro Arg
385                 390                 395                 400

Val Asp Arg Cys Val Ile Leu Ser Val Leu Ile Pro Pro Ser Phe Ala
                405                 410                 415

Leu Arg Leu Val Arg Pro Pro Leu Cys Ser Arg Arg Gln Thr Arg Ala
                420                 425                 430

Thr Leu Ala Ala Leu Leu His Leu Gln His His Thr Cys Pro Arg Leu
        435                 440                 445

His Ser Cys Arg Arg Leu Leu Arg Leu Glu Leu Arg Lys Gln Ala Arg
    450                 455                 460

Leu Ser
465

<210> SEQ ID NO 34
<211> LENGTH: 761
<212> TYPE: PRT
<213> ORGANISM: Festuca arundinacea

<400> SEQUENCE: 34

Met Ala Arg Ser Asn Trp Glu Ala Asp Lys Met Leu Asp Val Tyr Ile
1               5                   10                  15
```

-continued

```
Tyr Asp Tyr Leu Val Lys Arg Asn Leu His Asn Ser Ala Lys Ala Phe
            20                  25                  30

Met Asn Glu Gly Lys Val Ala Thr Asp Pro Val Ala Ile Asp Ala Pro
        35                  40                  45

Gly Gly Phe Leu Phe Glu Trp Trp Ser Ile Phe Trp Asp Ile Phe Asp
    50                  55                  60

Ala Arg Thr Arg Asp Lys Pro His Gln Gly Ala Thr Ala Ala Ser Ile
65                  70                  75                  80

Asp Leu Met Lys Ser Arg Glu Gln Gln Met Arg Ile Gln Leu Leu Gln
                85                  90                  95

Gln Gln Asn Ala His Leu Gln Arg Arg Asp Pro Asn His Pro Ala Val
            100                 105                 110

Asn Gly Ala Met Asn Asn Ser Asp Val Ser Ala Phe Leu Val Ser Lys
        115                 120                 125

Met Met Glu Glu Arg Thr Arg Asn His Gly Pro Met Asp Ser Glu Ala
    130                 135                 140

Ser Gln Gln Leu Leu Glu Ala Asn Lys Met Ala Leu Leu Lys Ser Ala
145                 150                 155                 160

Ala Ala Asn Gln Thr Gly Pro Leu Gln Gly Ser Ser Val Asn Met Ser
                165                 170                 175

Ala Leu Gln Gln Met Gln Ala Arg Asn Gln Gln Val Asp Ile Lys Gly
            180                 185                 190

Asp Gly Ala Met Pro Gln Arg Thr Met Pro Thr Asp Pro Ser Ala Leu
        195                 200                 205

Tyr Ala Ala Gly Met Met Gln Pro Lys Ser Gly Leu Val Ala Ser Gly
    210                 215                 220

Leu Asn Gln Gly Val Gly Ser Val Pro Leu Lys Gly Trp Pro Leu Thr
225                 230                 235                 240

Val Pro Gly Ile Asp Gln Leu Arg Ser Asn Leu Gly Ala Gln Lys Gln
                245                 250                 255

Leu Met Pro Ser Pro Asn Gln Phe Gln Leu Leu Ser Pro Gln Gln Gln
            260                 265                 270

Leu Ile Ala Gln Ala Gln Thr Gln Asn Asp Leu Ala Arg Met Gly Ser
        275                 280                 285

Pro Ala Pro Ser Gly Ser Pro Lys Ile Arg Pro Asn Glu Gln Glu Tyr
    290                 295                 300

Leu Ile Lys Met Lys Met Ala Gln Met Gln Gln Ser Gly Gln Arg Met
305                 310                 315                 320

Met Glu Leu Gln Gln Gln Gln His His Leu Gln Gln Gln Gln Gln Gln
                325                 330                 335

Gln Gln His Gln Gln Gln Gln Gln Gln Gln Gln Gln Gln Gln Gln Met
            340                 345                 350

Gln Gln Asn Thr Arg Lys Arg Lys Pro Thr Ser Ser Gly Ala Ala Asn
        355                 360                 365

Ser Thr Gly Thr Gly Asn Thr Val Gly Pro Ser Pro Pro Ser Thr Pro
    370                 375                 380

Ser Thr His Thr Pro Gly Gly Ile Pro Val Ala Ser Asn Ala Asn
385                 390                 395                 400

Ile Ala Gln Lys Asn Ser Met Val Cys Gly Thr Asp Gly Thr Ser Gly
                405                 410                 415

Phe Ala Ser Ser Ser Asn Gln Met Asp Asn Leu Asp Ser Phe Val Asp
            420                 425                 430
```

```
Phe Asp Asp Asn Val Asp Ser Phe Leu Ser Asn Asp Gly Asp Gly
            435                 440                 445

Arg Asp Ile Phe Ala Ala Met Lys Lys Gly Pro Ser Glu Gln Glu Ser
    450                 455                 460

Leu Lys Ser Leu Ser Leu Thr Glu Val Gly Asn Asn Arg Thr Ser Asn
465                 470                 475                 480

Asn Lys Val Val Cys Cys His Phe Ser Thr Asp Gly Lys Leu Leu Ala
                485                 490                 495

Ser Ala Gly His Glu Lys Lys Leu Phe Leu Trp Asn Met Asp Asn Phe
            500                 505                 510

Ser Met Asp Thr Lys Ala Glu Glu His Thr Asn Phe Ile Thr Asp Ile
            515                 520                 525

Arg Phe Arg Pro Asn Ser Thr Gln Leu Ala Thr Ser Ser Ser Asp Gly
            530                 535                 540

Thr Val Arg Leu Trp Asn Ala Val Glu Arg Thr Gly Ala Leu Gln Thr
545                 550                 555                 560

Phe His Gly His Thr Ser His Val Thr Ser Val Asp Phe His Pro Lys
                565                 570                 575

Leu Thr Glu Val Leu Cys Ser Cys Asp Asp Asn Arg Glu Leu Arg Phe
            580                 585                 590

Trp Thr Val Gly Gln Asn Ala Pro Ser Arg Val Thr Arg Val Lys Gln
            595                 600                 605

Gly Gly Thr Gly Arg Val Arg Phe Gln Pro Arg Met Gly Gln Leu Leu
            610                 615                 620

Ala Val Ala Ala Gly Asn Thr Val Asn Ile Ile Asp Ile Glu Lys Asp
625                 630                 635                 640

Thr Ser Leu His Ser Gln Pro Lys Val His Ser Gly Glu Val Asn Cys
                645                 650                 655

Ile Cys Trp Asp Glu Ser Gly Glu Tyr Leu Ala Ser Ala Ser Gln Asp
            660                 665                 670

Ser Val Lys Val Trp Ser Ala Ala Ser Gly Ala Cys Val His Glu Leu
            675                 680                 685

Arg Ser His Gly Asn Gln Tyr Gln Ser Cys Ile Phe His Pro Arg Tyr
            690                 695                 700

Pro Lys Val Leu Ile Val Gly Gly Tyr Gln Thr Met Glu Leu Trp Ser
705                 710                 715                 720

Leu Ser Asp Asn Gln Arg Asn Val Val Ala Ala His Glu Gly Leu Ile
                725                 730                 735

Ala Ala Leu Ala His Ser Pro Ser Thr Gly Ser Val Ala Ser Ala Ser
            740                 745                 750

His Asp Lys Ser Val Lys Leu Trp Lys
            755                 760

<210> SEQ ID NO 35
<211> LENGTH: 757
<212> TYPE: PRT
<213> ORGANISM: Festuca arundinacea

<400> SEQUENCE: 35

Met Ala Arg Ser Asn Trp Glu Ala Asp Lys Met Leu Asp Val Tyr Ile
1               5                   10                  15

Tyr Asp Tyr Leu Val Lys Arg Asn Leu His Asn Ser Ala Lys Ala Phe
                20                  25                  30

Met Asn Glu Gly Lys Val Ala Thr Asp Pro Val Ala Ile Asp Ala Pro
            35                  40                  45
```

```
Gly Gly Phe Leu Phe Glu Trp Trp Ser Ile Phe Trp Asp Ile Phe Asp
     50                  55                  60

Ala Arg Thr Arg Asp Lys Pro Pro Gln Gly Ala Thr Ala Ala Ser Ile
65                  70                  75                  80

Asp Leu Met Lys Ser Arg Glu Gln Gln Met Arg Ile Gln Leu Leu Gln
                 85                  90                  95

Gln Gln Asn Ala His Leu Gln Arg Arg Asp Pro Asn His Pro Ala Val
            100                 105                 110

Asn Gly Ala Met Asn Asn Ser Asp Val Ser Ala Phe Leu Val Ser Lys
            115                 120                 125

Met Met Glu Glu Arg Thr Arg Asn His Gly Pro Met Asp Ser Glu Ala
        130                 135                 140

Ser Gln Gln Leu Leu Glu Ala Asn Lys Met Ala Leu Leu Lys Ser Ala
145                 150                 155                 160

Ala Ala Asn Gln Thr Gly Pro Leu Gln Gly Ser Ser Val Asn Met Ser
                165                 170                 175

Ala Leu Gln Gln Met Gln Ala Arg Asn Gln Gln Val Asp Ile Lys Gly
            180                 185                 190

Asp Gly Ala Met Pro Gln Arg Thr Met Pro Thr Asp Pro Ser Ala Leu
            195                 200                 205

Tyr Ala Ala Gly Met Met Gln Pro Lys Ser Gly Leu Val Ala Ser Gly
        210                 215                 220

Leu Asn Gln Gly Ile Gly Ser Val Pro Leu Lys Gly Trp Pro Leu Thr
225                 230                 235                 240

Val Pro Gly Ile Asp Gln Leu Arg Ser Asn Leu Gly Ala Gln Lys Gln
                245                 250                 255

Leu Met Pro Ser Pro Asn Gln Phe Gln Leu Leu Ser Pro Gln Gln Gln
            260                 265                 270

Leu Ile Ala Gln Ala Gln Thr Gln Asn Asp Leu Ala Arg Met Gly Ser
        275                 280                 285

Pro Ala Pro Ser Gly Ser Pro Lys Ile Arg Pro Asn Glu Gln Glu Tyr
        290                 295                 300

Leu Ile Lys Met Lys Met Ala Gln Met Gln Gln Ser Gly Gln Arg Met
305                 310                 315                 320

Met Glu Leu Gln Gln Gln Gln His His Leu Gln Gln Gln Gln Gln Gln
                325                 330                 335

Gln Gln His Gln Gln Gln Gln Gln Gln Gln Met Gln Gln Asn Thr
            340                 345                 350

Arg Lys Arg Lys Pro Thr Ser Ser Gly Ala Ala Asn Ser Thr Gly Thr
        355                 360                 365

Gly Asn Thr Val Gly Pro Ser Pro Pro Ser Thr Pro Ser Thr His Thr
        370                 375                 380

Pro Gly Gly Gly Ile Pro Val Ala Ser Asn Ala Asn Ile Ala Gln Lys
385                 390                 395                 400

Asn Ser Met Val Cys Gly Thr Asp Gly Thr Ser Gly Phe Ala Ser Ser
                405                 410                 415

Ser Asn Gln Met Asp Asn Leu Asp Ser Phe Val Asp Phe Asp Asp Asn
            420                 425                 430

Val Asp Ser Phe Leu Ser Asn Asp Asp Gly Asp Gly Arg Asp Ile Phe
            435                 440                 445

Ala Ala Met Lys Lys Gly Pro Ser Glu Gln Glu Ser Leu Lys Ser Leu
450                 455                 460
```

```
Ser Leu Thr Glu Val Gly Asn Asn Arg Thr Ser Asn Lys Val Val
465                 470                 475                 480

Cys Cys His Phe Ser Thr Asp Gly Lys Leu Leu Ala Ser Ala Gly His
                485                 490                 495

Glu Lys Lys Leu Phe Leu Trp Asn Met Asp Asn Phe Ser Met Asp Thr
            500                 505                 510

Lys Ala Glu Glu His Thr Asn Phe Ile Thr Asp Ile Arg Phe Arg Pro
        515                 520                 525

Asn Ser Thr Gln Leu Ala Thr Ser Ser Asp Gly Thr Val Arg Leu
    530                 535                 540

Trp Asn Ala Val Glu Arg Thr Gly Ala Leu Gln Thr Phe His Gly His
545                 550                 555                 560

Thr Ser His Val Thr Ser Val Asp Phe His Pro Lys Leu Thr Glu Val
                565                 570                 575

Leu Cys Ser Cys Asp Asp Asn Gly Glu Leu Arg Phe Trp Thr Val Gly
                580                 585                 590

Gln Asn Ala Pro Ser Arg Val Thr Arg Val Lys Gln Gly Gly Thr Gly
                595                 600                 605

Arg Val Arg Phe Gln Pro Arg Met Gly Gln Leu Leu Ala Val Ala Ala
            610                 615                 620

Gly Asn Thr Val Asn Ile Ile Asp Ile Glu Lys Asp Thr Gly Leu His
625                 630                 635                 640

Ser Gln Pro Lys Val His Pro Gly Glu Val Asn Cys Ile Cys Trp Asp
                645                 650                 655

Glu Ser Gly Glu Tyr Leu Ala Ser Ala Ser Gln Asp Ser Val Lys Val
            660                 665                 670

Trp Ser Ala Ala Ser Gly Ala Cys Val His Glu Leu Arg Ser His Gly
            675                 680                 685

Asn Gln Tyr Gln Ser Cys Ile Phe His Pro Arg Tyr Pro Lys Val Leu
    690                 695                 700

Ile Val Gly Gly Tyr Gln Thr Met Glu Leu Trp Ser Leu Ser Asp Asn
705                 710                 715                 720

Gln Arg Asn Val Val Ala Ala His Glu Gly Leu Ile Ala Ala Leu Ala
                725                 730                 735

His Ser Leu Ser Thr Gly Ser Val Ala Ser Ala Ser His Asp Ser Ser
            740                 745                 750

Val Lys Leu Trp Lys
        755

<210> SEQ ID NO 36
<211> LENGTH: 174
<212> TYPE: PRT
<213> ORGANISM: Festuca arundinacea

<400> SEQUENCE: 36

Met Ser Arg Ala Leu Glu Pro Leu Val Val Gly Lys Val Ile Gly Glu
1               5                   10                  15

Val Leu Asp Ser Phe Asn Pro Thr Val Lys Met Ala Ala Thr Tyr Asn
            20                  25                  30

Ser Asn Lys Gln Val Phe Asn Gly His Glu Phe Phe Pro Ser Ala Ile
        35                  40                  45

Ala Ala Lys Pro Arg Val Glu Val Gln Gly Gly Asp Leu Arg Ser Phe
    50                  55                  60

Phe Thr Leu Val Met Thr Asp Pro Asp Val Pro Gly Pro Ser Asp Pro
65              70                  75                  80
```

Tyr Leu Arg Glu His Leu His Trp Ile Val Thr Asp Ile Pro Gly Thr
                85                  90                  95

Thr Asp Ala Ser Phe Gly Lys Glu Val Val Asn Tyr Glu Ser Pro Lys
            100                 105                 110

Pro Asn Ile Gly Ile His Arg Phe Ile Leu Val Leu Phe Gln Gln Thr
        115                 120                 125

His Arg Gly Ser Val Lys Asn Thr Pro Ser Ser Arg Asp Arg Phe Arg
    130                 135                 140

Thr Arg Glu Phe Ala Lys Asp Asn Glu Leu Gly Leu Pro Val Ala Ala
145                 150                 155                 160

Val Tyr Phe Asn Ala Gln Arg Glu Thr Ala Ala Arg Arg Arg
                165                 170

<210> SEQ ID NO 37
<211> LENGTH: 657
<212> TYPE: PRT
<213> ORGANISM: Festuca arundinacea

<400> SEQUENCE: 37

Gln His His His Leu Met Gln Leu Thr Lys Lys Asn Pro Gln Ala Ala
1               5                   10                  15

Ala Ala Ala Gln Leu Asn Leu Leu Gln Gln Gln Arg Ile Met His Met
            20                  25                  30

Gln Gln Gln Gln Gln Gln Gln Ile Leu Lys Asn Leu Pro Leu Gln Arg
        35                  40                  45

Asn Gln Leu Gln Gln Gln Gln Val Gln Gln Gln Gln Gln Gln Gln Gln
    50                  55                  60

Leu Gln Gln Gln Gln Leu Leu Arg Gln Gln Ser Leu Asn Met Arg
65                  70                  75                  80

Thr Pro Gly Lys Ser Pro Tyr Glu Pro Gly Thr Cys Ala Lys Arg
                85                  90                  95

Leu Thr His Tyr Met Tyr His Gln Gln Asn Arg Pro Gln Asp Asn Asn
            100                 105                 110

Ile Glu Tyr Trp Arg Asn Phe Val Asn Glu Tyr Phe Ala Pro Thr Ala
        115                 120                 125

Lys Lys Arg Trp Cys Val Ser Leu Tyr Gly Ser Gly Arg Gln Thr Thr
    130                 135                 140

Gly Val Phe Pro Gln Asp Val Trp His Cys Glu Ile Cys Asn Arg Lys
145                 150                 155                 160

Pro Gly Arg Gly Phe Glu Thr Thr Val Glu Val Leu Pro Arg Leu Cys
                165                 170                 175

Gln Ile Lys Tyr Ala Ser Gly Thr Leu Glu Glu Leu Leu Tyr Ile Asp
            180                 185                 190

Met Pro Arg Glu Ser Lys Asn Val Ser Gly Gln Ile Val Leu Asp Tyr
        195                 200                 205

Thr Lys Ala Ile Gln Glu Ser Val Phe Asp Gln Leu Arg Val Val Arg
    210                 215                 220

Glu Gly His Leu Arg Ile Ile Phe Asn Pro Asp Leu Lys Ile Ala Ser
225                 230                 235                 240

Trp Glu Phe Cys Ala Arg Arg His Glu Glu Leu Ile Pro Arg Arg Ser
                245                 250                 255

Ile Ile Pro Gln Val Ser Gln Leu Gly Ala Val Val Gln Lys Tyr Gln
            260                 265                 270

Ala Ala Ala Gln Asn Pro Thr Ser Leu Ser Thr Gln Asp Met Gln Asn

-continued

```
                275                 280                 285
Asn Cys Asn Ser Phe Val Ala Cys Ala Arg Gln Leu Ala Lys Ala Leu
            290                 295                 300
Glu Val Pro Leu Val Asn Asp Leu Gly Tyr Thr Lys Arg Tyr Val Arg
305                 310                 315                 320
Cys Leu Gln Ile Ala Glu Val Asn Cys Met Lys Asp Leu Ile Asp
                325                 330                 335
His Ser Arg Gln Thr Gly Ser Gly Pro Ile Asp Ser Leu His Lys Phe
            340                 345                 350
Pro Arg Arg Thr Pro Ser Gly Ile Asn Pro Leu Gln Ser Gln Gln Gln
            355                 360                 365
Gln Pro Glu Glu His Gln Ser Val Pro Gln Ser Ser Asn Gln Ser Gly
        370                 375                 380
Gln Asn Ser Ala Pro Met Ala Gly Val Gln Val Ser Ala Ser Ala Asn
385                 390                 395                 400
Ala Asp Ala Thr Ser Asn Asn Ser Ile Asn Cys Ala Pro Ser Thr Ser
                405                 410                 415
Ala Pro Ser Pro Thr Val Val Gly Leu Leu Gln Gly Ser Met Asp Ser
            420                 425                 430
Arg His Asn His Pro Met Cys Ser Ala Asn Gly Gln Tyr Asn Ser Gly
            435                 440                 445
Asn Asn Gly Ala Ile Pro Arg Val Asn Ser Ala Ser Ser Leu Gln Ser
        450                 455                 460
Asn Pro Ser Ser Pro Phe Pro Ser Gln Val Pro Thr Ser Pro Asn Asn
465                 470                 475                 480
Asn Met Met Pro Thr Leu Gln Asn Ala Asn Gln Leu Ser Ser Pro Pro
                485                 490                 495
Ala Val Ser Ser Asn Leu Pro Pro Ile Gln Pro Pro Ser Thr Arg Pro
            500                 505                 510
Gln Glu Ser Glu Pro Ser Asp Ala Gln Ser Ser Val Gln Arg Ile Leu
            515                 520                 525
Gln Glu Met Met Ser Ser Gln Met Asn Gly Val Gly His Gly Gly Asn
        530                 535                 540
Asp Met Lys Arg Pro Asn Gly Leu Thr Pro Gly Ile Asn Gly Val Asn
545                 550                 555                 560
Cys Leu Val Gly Asn Ala Val Thr Asn His Ser Gly Met Gly Met
                565                 570                 575
Gly Phe Gly Ala Met Gly Gly Phe Gly Ser Thr Pro Ala Ala Ser Gly
            580                 585                 590
Leu Arg Met Ala Met Thr Asn Asn Ala Met Ala Met Asn Gly Arg Met
            595                 600                 605
Gly Met His His Ser Ala Gln Asp Leu Ser Gln Leu Gly Gln Gln His
        610                 615                 620
Gln His Gln His Gln His Asp Ile Gly Asn Gln Leu Leu Gly Gly Leu
625                 630                 635                 640
Gly Ala Ala Asn Ser Phe Asn Asn Ile Gln Tyr Asp Trp Lys Pro Ser
                645                 650                 655
Gln
```

<210> SEQ ID NO 38
<211> LENGTH: 808
<212> TYPE: PRT
<213> ORGANISM: Festuca arundinacea

```
<400> SEQUENCE: 38

Met Ser Gly Ala Pro Arg Ser Asn Leu Gly Phe Val Ala Arg Asp Met
 1               5                  10                  15

Asn Gly Ser Ile Pro Val Ser Ser Ala Asn Ser Ser Gly Pro Ser Ile
             20                  25                  30

Gly Val Ser Ser Leu Val Thr Asp Gly Asn Ser Ser Leu Ser Gly Gly
         35                  40                  45

Ala Gln Phe Gln His Ser Thr Ser Met Asn Ala Asp Ser Phe Met Arg
     50                  55                  60

Leu Pro Ala Ser Pro Met Ser Phe Ser Ser Asn Asn Ile Ser Gly Ser
65                  70                  75                  80

Ser Val Ile Asp Gly Ser Ile Met Gln Gln Ser Pro Pro Gln Asp Gln
                 85                  90                  95

Met Gln Lys Arg Arg Ser Ser Thr Ala Thr Ser Gln Pro Gly Ile Glu
            100                 105                 110

Ala Gly Ala Ala Phe His Ala Gln Lys Lys Pro Arg Val Asp Ile Arg
        115                 120                 125

Gln Asp Asp Ile Leu Gln Gln His Leu Ile Gln Gln Val Leu Gln Gly
    130                 135                 140

Gln Ser Ser Leu His Leu Pro Gly Gln His Asn Pro Gln Leu Gln Ala
145                 150                 155                 160

Leu Ile Arg Gln Gln Lys Leu Ala His Ile Gln His Leu Gln Gln Gln
                165                 170                 175

Gln Leu Ser Gln Gln Phe Pro Gly Ile Gln Gln Ser Gln Val Gly Ile
            180                 185                 190

Pro Arg Gln Pro Gln Leu Arg Leu Pro Leu Ala Gln Pro Gly Met Gln
        195                 200                 205

Leu Ala Gly Pro Val Arg Thr Pro Val Glu Ser Gly Leu Cys Ser Arg
    210                 215                 220

Arg Leu Met Gln Tyr Leu Phe His Lys Arg His Arg Pro Glu Asp Asn
225                 230                 235                 240

Pro Ile Thr Tyr Trp Arg Lys Leu Ile Asp Glu Tyr Phe Ala Pro Arg
                245                 250                 255

Ala Arg Glu Arg Trp Cys Val Ser Ser Tyr Glu Lys Arg Gly Asn Ser
            260                 265                 270

Pro Val Ala Ile Pro Gln Thr Ser Gln Asp Thr Trp Arg Cys Asp Ile
        275                 280                 285

Cys Asn Thr His Ala Gly Lys Gly His Glu Ala Thr Tyr Glu Ile Leu
    290                 295                 300

Pro Arg Leu Cys Gln Ile Arg Phe Asp Gln Gly Val Ile Asp Glu Tyr
305                 310                 315                 320

Leu Phe Leu Asp Met Pro Asn Glu Phe Arg Leu Pro Asn Gly Leu Leu
                325                 330                 335

Leu Leu Glu His Thr Lys Val Val Gln Lys Ser Ile Tyr Asp His Leu
            340                 345                 350

His Val Thr His Glu Gly Gln Leu Arg Ile Ile Phe Thr Pro Glu Leu
        355                 360                 365

Lys Ile Met Ser Trp Glu Phe Cys Ser Arg Arg His Asp Glu Tyr Ile
    370                 375                 380

Thr Arg Arg Phe Leu Thr Pro Gln Val Asn His Met Leu Gln Val Ala
385                 390                 395                 400

Gln Lys Tyr Gln Ala Ala Asn Glu Ser Gly Pro Ala Gly Val Ser
                405                 410                 415
```

```
Asn Asn Asp Ala Gln Ala Ile Cys Ser Met Phe Val Ser Ala Ser Arg
            420                 425                 430

Gln Leu Ala Lys Asn Leu Asp His His Ser Leu Asn Glu His Gly Leu
            435                 440                 445

Ser Lys Arg Tyr Val Arg Cys Leu Gln Ile Ser Glu Val Val Asn His
            450                 455                 460

Met Lys Asp Leu Ile Glu Phe Ser His Lys Asn Lys Leu Gly Pro Ile
465                 470                 475                 480

Glu Gly Leu Lys Asn Tyr Pro Arg Gln Thr Gly Pro Lys Leu Thr Thr
                485                 490                 495

Gln Asn Met His Asp Ala Lys Gly Val Val Lys Thr Glu Glu Ser Thr
            500                 505                 510

His Val Asn Asn Glu Gly Pro Asp Ala Gly Pro Ala Gly Ser Ser Pro
            515                 520                 525

Gln Asn Ala Gly Ala Gln Asn Asn Tyr Gln Asn Met Leu Arg Ser Pro
            530                 535                 540

Ser Pro Asn Gln Gly Leu Thr His Gln Glu Ala Ser Gln Asn Ala Ala
545                 550                 555                 560

Ala Leu Asn Asn Tyr Gln Asn Met Leu Arg Ser Ser Ser Ala Asn Gln
                565                 570                 575

Gly Leu Leu Gln Gln Glu Ala Ser Gln Asn Val Ser Gly Leu Asn Asn
            580                 585                 590

Tyr Gln Asn Met Leu Arg Ser Ser Ala Asn Gln Ser Ile Leu Gln
                595                 600                 605

Gln Glu Ala Ser Ser Ile Phe Lys Gly Pro Thr Gly Val His Ser Ser
            610                 615                 620

Ile Gln Leu Glu Ala Ala Arg Ser Phe Arg Ala Ala Gln Leu Gly Pro
625                 630                 635                 640

Met Ser Phe Gln Gln Ala Val Pro Leu Tyr Gln Gln Asn Arg Phe Gly
                645                 650                 655

Ala Gly Val Ser Pro Gln Tyr Gln Gln His Val Met Gln Gln Leu Leu
            660                 665                 670

Gln Glu Ala Asn Arg Ser Thr Asn Asn Arg Val Leu Ala Gln Gln Gln
            675                 680                 685

Pro Leu Ser Thr Pro Asn Ala Asn Gly Gly Leu Thr Ile Thr Asn Ser
            690                 695                 700

Gly Ala Ser Gly Asp Gln Ala Gln His Met Asn Asn Asn Gly Ala Ala
705                 710                 715                 720

Lys Gly Val Ala Ala Pro Met Gly Met Ala Gly Thr Ser Asn Leu Ile
                725                 730                 735

Asn Ser Gly Ser Ala Gly Val Val Gln Arg Cys Ser Ser Phe Lys Ser
            740                 745                 750

Val Thr Ser Asn Pro Ala Ala Ala Ala Gly Asn Leu Leu Thr Pro
            755                 760                 765

Lys Ala Glu Ser Met His Glu Met Asp Glu Leu Asp His Leu Ile Thr
            770                 775                 780

Ser Glu Leu Ala Glu Ser Gly Leu Phe Met Gly Glu Gln Gln Gly Gly
785                 790                 795                 800

Gly Gly Gly Tyr Ser Trp His Met
                805
```

<210> SEQ ID NO 39
<211> LENGTH: 798

```
<212> TYPE: PRT
<213> ORGANISM: Festuca arundinacea

<400> SEQUENCE: 39

Ser Asp Pro Leu Ser Phe Pro Ser Ser His Val Ser Leu Gly Asn
 1               5                  10                  15

His Ile Ser Ser Asp Asn Leu Gln Gln Gln Gln Met Asp Met Pro
             20                  25                  30

Asp Leu Gln Gln Gln Gln Gln Gln Gln Arg Gln Leu Pro Met Ser
         35                  40                  45

Tyr Asn Gln Gln His Leu Pro Met Gln Arg Pro Gln Pro Gln Ala Thr
 50                  55                  60

Val Lys Leu Glu Asn Gly Gly Ser Met Gly Gly Val Lys Met Glu Gln
 65                  70                  75                  80

Gln Thr Gly His Pro Asp Gln Asn Gly Pro Ala Gln Met Met His Asn
                 85                  90                  95

Ser Gly Asn Val Lys Phe Glu Pro Gln Gln Leu Gln Ala Leu Arg Gly
            100                 105                 110

Leu Gly Thr Val Lys Met Glu Gln Pro Asn Ser Asp Pro Ser Ala Phe
        115                 120                 125

Leu Gln Gln Gln Gln Gln Gln Gln Gln His His His Leu Met Gln
130                 135                 140

Leu Thr Lys Gln Asn Pro Gln Ala Ala Ala Ala Gln Leu Asn Leu
145                 150                 155                 160

Leu Gln Gln Gln Arg Ile Met His Met Gln Gln Gln Gln Gln His
                165                 170                 175

Ile Leu Lys Asn Met Pro Leu Gln Arg Asn Gln Leu Gln Gln Gln Gln
            180                 185                 190

Gln Gln Gln Gln Leu Gln Gln Gln His Gln Gln Leu Leu Arg
        195                 200                 205

Gln Gln Ser Leu Asn Met Arg Thr Pro Gly Lys Ser Pro Pro Tyr Glu
        210                 215                 220

Pro Gly Thr Cys Ala Lys Arg Leu Thr His Tyr Met Tyr His Gln Gln
225                 230                 235                 240

Asn Arg Pro Gln Asp Asn Asn Val Glu Tyr Trp Arg Asn Phe Val Asn
                245                 250                 255

Glu Tyr Phe Ala Pro Thr Ala Lys Lys Arg Trp Cys Val Ser Leu Tyr
            260                 265                 270

Gly Ser Gly Arg Gln Thr Thr Gly Val Phe Pro Gln Asp Val Trp His
        275                 280                 285

Cys Glu Ile Cys Asn Arg Lys Pro Gly Arg Gly Phe Glu Thr Thr Val
290                 295                 300

Glu Val Leu Pro Arg Leu Cys Gln Ile Lys Tyr Ala Ser Gly Thr Leu
305                 310                 315                 320

Glu Glu Leu Leu Tyr Ile Asp Met Pro Arg Glu Ser Lys Asn Val Ser
                325                 330                 335

Gly Gln Ile Val Leu Asp Tyr Thr Lys Ala Ile Gln Glu Ser Val Phe
            340                 345                 350

Asp Gln Leu Arg Val Val Arg Glu Gly His Leu Arg Ile Ile Phe Asn
        355                 360                 365

Pro Asp Leu Lys Ile Ala Ser Trp Glu Phe Cys Ala Arg Arg His Glu
370                 375                 380

Glu Leu Ile Pro Arg Arg Ser Ile Ile Pro Gln Val Ser Gln Leu Gly
385                 390                 395                 400
```

```
Ala Val Val Gln Lys Tyr Gln Ala Ala Gln Asn Pro Thr Ser Leu
            405                 410                 415

Ser Thr Gln Asp Leu Gln Asn Asn Cys Asn Ser Phe Val Ala Cys Ala
            420                 425                 430

Arg Gln Leu Ala Lys Ala Leu Glu Val Pro Leu Val Asn Asp Leu Gly
            435                 440                 445

Tyr Thr Lys Arg Tyr Val Arg Cys Leu Gln Ile Ala Glu Val Val Asn
            450                 455                 460

Cys Met Lys Asp Leu Ile Asp His Ser Arg Gln Thr Gly Ser Gly Pro
465                 470                 475                 480

Ile Asp Ser Leu His Lys Phe Pro Arg Arg Thr Pro Ser Gly Ile Asn
            485                 490                 495

Pro Leu Gln Ser Gln Gln Gln Pro Glu Gln Gln Ser Val Pro
            500                 505                 510

Gln Ser Ser Asn Gln Ser Gly Gln Asn Ser Ala Pro Met Ala Gly Val
            515                 520                 525

Gln Val Ser Ala Ser Ala Asn Ala Asp Ala Thr Ser Asn Asn Ser Leu
530                 535                 540

Asn Cys Ala Pro Ser Thr Ser Ala Pro Ser Pro Thr Val Val Gly Leu
545                 550                 555                 560

Leu Gln Gly Ser Met Asp Ser Arg Gln Asp His Pro Met Cys Ser Ala
            565                 570                 575

Asn Gly Gln Tyr Asn Ser Gly Asn Asn Gly Ala Ile Pro Arg Val Asn
            580                 585                 590

Ser Ala Ser Ser Leu Gln Ser Asn Pro Ser Ser Pro Phe Pro Leu Gln
            595                 600                 605

Val Pro Thr Ser Pro Asn Asn Asn Met Met Pro Thr Leu Gln Asn Ala
            610                 615                 620

Asn Gln Leu Ser Ser Pro Pro Ala Val Ser Pro Asn Leu Pro Pro Met
625                 630                 635                 640

Gln Pro Pro Ser Thr Arg Pro Gln Glu Ser Glu Pro Ser Asp Ala Gln
            645                 650                 655

Ser Ser Val Gln Arg Ile Leu Gln Glu Met Met Ser Ser Gln Met Asn
            660                 665                 670

Gly Val Gly His Ala Gly Asn Asp Met Lys Arg Pro Asn Gly Leu Thr
            675                 680                 685

Pro Gly Ile Asn Gly Val Asn Cys Leu Val Gly Asn Ala Val Thr Asn
            690                 695                 700

His Ser Met Gly Gly Met Gly Phe Gly Ala Met Gly Gly Phe Gly
705                 710                 715                 720

Ser Asn Pro Ala Ala Ser Gly Leu Arg Met Ala Met Thr Asn Asn Thr
            725                 730                 735

Met Ala Met Asn Gly Arg Met Gly Met His His Ser Ala His Asp Leu
            740                 745                 750

Ser Gln Leu Gly Gln Gln His Gln His Gln His Gln His
            755                 760                 765

His Gln His Asp Ile Gly Asn Gln Leu Leu Gly Gly Leu Arg Ala Thr
            770                 775                 780

Asn Ser Phe Asn Asn Ile Gln Tyr Asp Trp Lys Pro Ser Gln
785                 790                 795

<210> SEQ ID NO 40
<211> LENGTH: 609
```

<212> TYPE: PRT
<213> ORGANISM: Festuca arundinacea

<400> SEQUENCE: 40

```
Met Lys Arg Glu Tyr Gln Asp Ala Gly Gly Ser Ser Ala Gly Gly Asp
  1               5                  10                  15

Met Gly Met Ser Lys Asp Lys Met Met Ser Ala Pro Pro Ala Gln Glu
             20                  25                  30

Asp Glu Asp Val Asp Glu Leu Leu Ala Ala Leu Gly Tyr Lys Val Arg
         35                  40                  45

Ser Ser Asp Met Ala Asp Val Ala Gln Lys Leu Glu Gln Leu Glu Met
 50                  55                  60

Ala Met Gly Met Gly Gly Val Pro Ala Pro Asp Asp Gly Phe Thr Thr
 65                  70                  75                  80

His Leu Ala Thr Glu Thr Val His Tyr Asn Pro Thr Asp Leu Ser Ser
             85                  90                  95

Trp Val Glu Ser Met Leu Ser Glu Leu Asn Ala Pro Pro Leu Pro
                100                 105                 110

Pro Ala Pro Arg Leu Ala Pro Ala Ser Ala Ser Val Thr Ala Asp Gly
            115                 120                 125

Phe Phe Asp Ile Pro Pro Ser Val Asp Ser Ser Ser Thr Tyr
    130                 135                 140

Ala Leu Arg Pro Ile Pro Ser Pro Ala Asp Leu Ser Ala Asp Leu Ser
145                 150                 155                 160

Ala Asp Ser Pro Arg Asp Pro Lys Arg Met Arg Thr Gly Gly Gly Ser
                165                 170                 175

Thr Ser Ser Ser Ser Ser Ser Ser Ser Leu Gly Gly Cys Val Val
            180                 185                 190

Glu Ala Ala Pro Pro Ala Ala Ala Glu Ala Asn Ala Ile Ala Leu Pro
        195                 200                 205

Val Val Val Ala Asp Thr Gln Glu Ala Gly Ile Arg Leu Val His Ala
    210                 215                 220

Leu Leu Ala Cys Ala Glu Ala Val Gln Gln Glu Asn Phe Ser Ala Ala
225                 230                 235                 240

Glu Ala Leu Val Lys Gln Ile Pro Leu Leu Ala Ala Ser Gln Gly Gly
                245                 250                 255

Ala Met Arg Lys Val Ala Ala Tyr Phe Gly Glu Ala Leu Ala Arg Arg
            260                 265                 270

Val Phe Arg Phe Arg Pro Gln Pro Asp Ser Ser His Leu Asp Ala Ala
        275                 280                 285

Phe Ala Asp Leu Leu His Ala His Phe Tyr Glu Ser Cys Pro Tyr Leu
    290                 295                 300

Lys Phe Ala His Phe Thr Ala Asn Gln Ala Ile Leu Glu Ala Phe Ala
305                 310                 315                 320

Gly Cys Arg Arg Val His Val Val Asp Phe Gly Ile Lys Gln Gly Met
                325                 330                 335

Gln Trp Pro Ala Leu Leu Gln Ala Leu Ala Leu Arg Pro Gly Gly Pro
            340                 345                 350

Pro Ser Phe Arg Leu Thr Gly Val Gly Pro Pro Gln Pro Asp Glu Thr
        355                 360                 365

Asp Ala Leu Gln Gln Val Gly Trp Lys Leu Ala Gln Phe Ala His Thr
    370                 375                 380

Ile Gly Val Asp Phe Gln Tyr Arg Gly Leu Val Ala Ala Thr Leu Ala
385                 390                 395                 400
```

-continued

```
Asp Leu Glu Pro Phe Met Leu Gln Pro Glu Ala Glu Asp Gly Pro Asn
            405                 410                 415

Glu Glu Pro Glu Val Ile Ala Val Asn Ser Ile Phe Glu Met His Arg
            420                 425                 430

Leu Leu Ala Gln Pro Gly Ala Leu Glu Lys Val Leu Gly Thr Val Arg
            435                 440                 445

Ala Val Arg Pro Arg Ile Val Thr Val Val Glu Gln Glu Ala Asn His
        450                 455                 460

Asn Ala Gly Ser Phe Leu Asp Arg Phe Thr Glu Ser Leu His Tyr Tyr
465                 470                 475                 480

Ser Thr Met Phe Asp Ser Leu Glu Gly Ala Gly Ser Gly Pro Ser Glu
                485                 490                 495

Ile Ser Ser Gly Pro Ala Ala Ala Ala Ala Pro Gly Thr Asp Gln
                500                 505                 510

Val Met Ser Glu Val Tyr Leu Gly Arg Gln Ile Cys Asn Val Val Ala
            515                 520                 525

Cys Glu Gly Ala Glu Arg Thr Glu Arg His Glu Thr Leu Gly His Trp
            530                 535                 540

Arg Gly Arg Leu Gly His Ala Gly Phe Glu Thr Val His Leu Gly Ser
545                 550                 555                 560

Asn Ala Tyr Lys Gln Ala Ser Thr Leu Leu Ala Leu Phe Ala Gly Gly
                565                 570                 575

Asp Gly Tyr Lys Val Asp Glu Lys Glu Gly Cys Leu Thr Leu Gly Trp
                580                 585                 590

His Thr Arg Pro Leu Ile Ala Thr Ser Ala Trp Arg Met Ala Ala Ala
            595                 600                 605

Pro
```

US 7,538,260 B2

COMPOSITIONS ISOLATED FROM FORAGE GRASSES AND METHODS FOR THEIR USE

REFERENCE TO RELATED APPLICATIONS

This application claims priority to U.S. Provisional Patent Application No. 60/563,723 filed Apr. 20, 2004, and is a continuation-in-part of U.S. patent application Ser. No. 10/655,799, filed Sep. 5, 2003, now U.S. Pat. No. 7,265,278 which claims priority to U.S. Provisional Patent Application No. 60/408,782 filed Sep. 5, 2002.

TECHNICAL FIELD OF THE INVENTION

This invention relates to polynucleotides isolated from forage grass tissues, specifically from *Lolium perenne* (perennial ryegrass) and *Festuca arundinacea* (tall fescue), as well as oligonucleotide probes and primers, genetic constructs comprising the polynucleotides, biological materials (including host cells and plants) incorporating the polynucleotides, polypeptides encoded by the polynucleotides, and methods for using the polynucleotides and polypeptides. More particularly, the invention relates to polypeptides involved in the regulation of flowering and to polynucleotides encoding such polypeptides.

BACKGROUND OF THE INVENTION

Over the past 50 years, there have been substantial improvements in the genetic production potential of ruminant animals (sheep, cattle and deer). Levels of meat, milk or fiber production that equal an animal's genetic potential may be attained within controlled feeding systems, where animals are fully fed with energy dense, conserved forages and grains. However, the majority of temperate farming systems worldwide rely on the in situ grazing of pastures. Nutritional constraints associated with temperate pastures can prevent the full expression of an animal's genetic potential. This is illustrated by a comparison between milk production by North American grain-fed dairy cows and New Zealand pasture-fed cattle. North American dairy cattle produce, on average, twice the milk volume of New Zealand cattle, yet the genetic base is similar within both systems (New Zealand Dairy Board and United States Department of Agriculture figures). Significant potential therefore exists to improve the efficiency of conversion of pasture nutrients to animal products through the correction of nutritional constraints associated with pastures.

The ability to control flowering in $C_3$ monocotyledonous plants, such as forage grasses (e.g. perennial ryegrass and tall fescue) and cereals (e.g. wheat and barley), has wide ranging applications. For example, controlling flowering in forage grasses offers the ability to halt the increase in syringyl lignin that is associated with the decrease in digestibility of forage at this time. In addition, it offers the ability to control the spread of genetically modified organisms, as well as lowering the incidence of allergies associated with ryegrass pollen levels. Other advantages include the ability to induce the time of flowering to suit farming practices better. To achieve this, a flowering control gene would have to be placed under the control of an inducible promoter and the endogenous flowering genes would need to be silenced. A number of genes are known to control flowering in a range of species.

A simple model has been proposed for the genetic network regulating flowering time and flower development in *Arabidopsis*. In *Arabidopsis* there are three genetic pathways that control flowering time (Reeves and Coupland, *Curr. Opin. Plant Biol.* 3:37-42, 2000). The long-day pathway represented by GIGANTEA (GI) and CONSTANS (CO), and the autonomous pathway represented by LUMINIDEPENDENS (LD), FLOWERING TIME CONTROL PROTEIN (FCA) and FLOWERING LOCUS C (FLC) are likely integrated through FLOWERING LOCUS T (FT) and AGAMOUS-LIKE20 (AGL20) to promote activation of meristem identity genes LEAFY (LFY), APETALA1 (AP1) and CAULI-FLOWER (CAL). The vernalization pathway represented by FRIGIDA (FRI), feeds into the autonomous pathway upstream of FLC. The giberellin pathway (GA) is represented by gibberellic acid insensitive (GAI) that leads to the activation of LFY. The TERMINAL FLOWER 1 (TFL1) restricts the expression of the meristem identity genes to the floral meristems, thereby promoting the patterned expression of floral organ identity genes such as APETALA2 (AP2), APETALA3 (AP3), PISTILATA (PI), and AGAMOUS (AG). These floral identity genes are also affected by other regulatory genes such as AINTEGUMENTA (ANT), UNUSUAL FLORAL ORGANS (UFO) and SUPERMAN (SUP). Homologs of some of these genes have been identified in other monocots such as maize and rice as well as the dicot species *Antirrhinum*, where they play a role that is either similar or divergent to that of the *Arabidopsis* gene in flowering. For example, some key regulatory flowering genes are conserved between rice and *Arabidopsis*, however, the regulation of FT by CO is reversed in the two species under long day conditions (Hayama et al., *Nature* 422, 719-722, 2003).

Both genetic and molecular studies have led to the proposal of the ABC model for floral organ identity (Ma and DePamphilis, *Cell* 101:5-8, 2000). The *Arabidopsis* B function genes, APETALA3 (AP3) and PISTILATA (PI), are required to specify petal and stamen identities. The *Arabidopsis* meristem identity gene, LFY, is required for normal levels of AP3 and PI expression (Weigel and Meyerowitz, *Science* 261: 1723-1726, 1993). The *Arabidopsis* gene UFO plays a role in controlling floral meristem development and B function, and the activation of AP3 by LFY requires UFO (Lee et al., *Curr. Biol.* 7:95-104, 1997). The ASK1 gene regulates B function gene expression in cooperation with UFO and LFY in *Arabidopsis* (Zhao et al., *Development* 128:2735-2746, 2001; Durfee et al., *Proc. Natl. Acad. Sci. USA* 100:8571-8576, 2003).

It has been suggested that UFO and ASK1 may be subunits of a three-component SCF (SKP1, cullin, F-box) ubiquitin ligase. In addition, ASK1 shows high sequence identity to the yeast SKP1 protein. Ubiquitin ligase is part of the ubiquitin-dependent protein degradation pathway; this suggests that UFO and ASK1 may regulate the level of other regulatory proteins that control cell division and transcription during floral development.

FCA encodes a strong promoter of the transition to flowering in *Arabidopsis. Arabidopsis* fca mutants flower late in both long days and short days. FCA has been cloned and shown to encode a protein containing two RNA-binding domains and a WW protein interaction domain (Macknight et al., *Cell* 89:737-745, 1997). The regulation of FCA expression is complex. FCA pre-mRNA is alternatively processed resulting in four types of transcripts of which FCA-γ is the active form. Recent studies have shown that FCA functions with FY, a WD-repeat protein, to regulate 3' end formation of mRNA and control the floral transition (Simpson et al., *Cell* 113:777-787, 2003). Plants carrying the FCA gene fused to the strong constitutive 35S promoter flowered earlier, and the ratio and abundance of the different FCA transcripts were altered. The rice genome contains a single copy homolog of FCA (Goff et al., *Science* 296:92-100, 2002).

The FT/TFL gene family encodes proteins with homology to phosphatidy-ethanolamine binding proteins that have been shown to be involved in major aspects of whole-plant architecture. FT acts in parallel with the meristem-identity gene LFY to induce flowering of *Arabidopsis* (Kardailsky et al., *Science* 286:1962-1965, 1999). It is similar in sequence to TFL1, an inhibitor of flowering (Ohshima et al., *Mol. Gen. Genet.* 254:186-194, 1997). The crystal structure of the *Antirrhinum* FT/TFL homolog, CENTRORADIALIS (CEN) suggests that it has a role as a kinase regulator (Banfield and Brady, *J. Mol. Biol.* 14:1159-1170, 2000). The rice genome contains 17 members of the FT/TFL gene family; one member is most similar to TFL, and nine are more similar to FT. A functional FT ortholog from rice, Hd3a, was detected as a heading date QTL and has the same regulatory relationship with rice CONSTANS homolog, Hd1, that *Arabidopsis* FT has with CO (Kojima et al., *Plant Cell Physiol.* 43:1096-1105, 2002). A TFL1-like gene from *Lolium perenne* has been isolated and characterized (Jensen et al., *Plant Physiol.* 125: 1517-1528, 2001). *Arabidopsis* plants over-expressing the LpTFL1 gene were significantly delayed in flowering and the LpTFL1 gene was able to complement the severe tfl1-14 mutant of *Arabidopsis*.

The *Arabidopsis* gai (gibberellic acid insensitive) mutant allele confers a reduction in gibberellin (GA) responsiveness, thereby playing a role in the GA regulated control of flowering. GAI contains nuclear localization signals, a region of homology to a putative transcription factor, and motifs characteristic of transcriptional co-activators (Peng et al., *Genes Dev.* 11:3194-3205, 1997). Homologs from other plant species have been identified, for example, RHT from wheat, D8 from maize and SLR1 from rice (Ikeda et al., *Plant Cell* 13:999-1010, 2001). Four rice sequence homologs of the *Arabidopsis* GAI gene have been identified in the rice genome (Goff et al., *Science* 296:92-100, 2002).

Alongside CONSTANS (CO), GIGANTEA (GI) exerts major control over the promotion of flowering under long days in *Arabidopsis*. Mutations in the *Arabidopsis thaliana* GI gene cause photoperiod-insensitive flowering and alteration of circadian rhythms. GI, originally described as a putative membrane protein (Fowler et al., *EMBO J.* 18:4679-4688, 1999), was recently determined to be a nuclear protein involved in phytochrome signaling (Huq et al., *Proc. Natl. Acad. Sci. USA* 97:9789-9794, 2000). GI is believed to function upstream of CO, because the late-flowering phenotype of GI mutants is corrected by CO over expression (Fowler et al., *EMBO J.* 18:4679-4688, 1999). A single putative GI ortholog exists in rice, based on the similarity of the predicted GI amino acid sequence. Overexpression of OsGI, an ortholog of the *Arabidopsis* GIGANTEA (GI) gene in transgenic rice, caused late flowering under both SD and LD conditions (Hayama et al., *Nature* 422, 719-722, 2003).

The indeterminate1 (id1) mutation in maize results in plants that are unable to undergo a normal transition to flower development and remain in a prolonged state of vegetative growth. The ID1 gene plays an important role in controlling the transition to flowering and maintaining the florally determined state. The ID1 gene was cloned by transposon mapping in maize (Colasanti et al., *Cell* 93:593-603, 1998). The ID1 gene encodes a protein with zinc finger motifs, indicating that it functions by transcriptional regulation of flowering. Expression studies showed that ID1 is expressed in immature leaves and not the shoot apex, and may therefore mediate the transition to flowering by regulating the transmission or synthesis of a signal for flowering. ID1 functional homologs have not been in identified in *Arabidopsis* but putative ID1 gene sequences have been identified from rice (Goff et al., *Science* 296:92-100, 2002).

LEUNIG (LUG) is a key regulator of the *Arabidopsis* floral homeotic gene AGAMOUS. Mutations in LEUNIG cause ectopic AGAMOUS mRNA expression in the outer two whorls of a flower, leading to homeotic transformations of floral organ identity as well as loss of floral organs. LEUNIG is a glutamine-rich protein with seven WD repeats and is similar in motif structure to a class of functionally related transcriptional co-repressors. The nuclear localization of LEUNIG is consistent with a role of LEUNIG as a transcriptional regulator (Conner and Liu, *Proc. Natl. Acad. Sci. USA* 97:12902-12907, 2000). Another regulatory gene, SEUSS, has recently been identified that functions together with LEUNIG to regulate AGAMOUS (Franks et al., *Development* 129:253-263, 2002).

SUMMARY OF THE INVENTION

The present invention provides polypeptides involved in the flowering pathway that are encoded by polynucleotides isolated from forage grass tissues. The polynucleotides were isolated from *Lolium perenne* (perennial ryegrass) and *Festuca arundinacea* (tall fescue) tissues taken at different times of the year, specifically in winter and spring, and from different parts of the plants, including: leaf blades, leaf base, pseudostems, inflorescence, roots and stems. The present invention also provides genetic constructs, expression vectors and host cells comprising the inventive polynucleotides, and methods for using the inventive polynucleotides and genetic constructs to modulate flowering.

In specific embodiments, the isolated polynucleotides of the present invention comprise a sequence selected from the group consisting of: (a) SEQ ID NO: 1-20; (b) complements of SEQ ID NO: 1-20; (c) reverse complements of SEQ ID NO: 1-20; (d) reverse sequences of SEQ ID NO: 1-20; (e) sequences having a 99% probability of being functionally or evolutionarily related to a sequence of (a)-(d), determined as described below; and (f) sequences having at least 75%, 80%, 90%, 95% or 98% identity to a sequence of (a)-(d), the percentage identity being determined as described below. Polynucleotides comprising at least a specified number of contiguous residues ("x-mers") of any of SEQ ID NO: 1-20, and oligonucleotide probes and primers corresponding to SEQ ID NO: 1-20, are also provided. All of the above polynucleotides are referred to herein as "polynucleotides of the present invention."

In further aspects, the present invention provides isolated polypeptides comprising an amino acid sequence of SEQ ID NO: 21-40, together with polypeptides comprising a sequence having at least 75%, 80%, 90%, 95% or 98% identity to a sequence of SEQ ID NO: 21-40, wherein the polypeptide possesses the same functional activity as the polypeptide comprising a sequence of SEQ ID NO: 21-40. The present invention also contemplates isolated polypeptides comprising at least a functional portion of a polypeptide comprising an amino acid sequence selected from the group consisting of: (a) SEQ ID NO: 21-40; and (b) sequences having at least 75%, 80%, 90%, 95% or 98% identity to a sequence of SEQ ID NO: 21-40.

In another aspect, the present invention provides genetic constructs comprising a polynucleotide of the present invention, either alone or in combination with one or more of the inventive sequences, or in combination with one or more known polynucleotides.

In certain embodiments, the present invention provides genetic constructs comprising, in the 5'-3' direction: a gene promoter sequence; an open reading frame coding for at least a functional portion of a polypeptide of the present invention; and a gene termination sequence. An open reading frame may be orientated in either a sense or anti-sense direction. Genetic constructs comprising a non-coding region of a polynucleotide of the present invention or a polynucleotide complementary to a non-coding region, together with a gene promoter sequence and a gene termination sequence, are also provided. Preferably, the gene promoter and termination sequences are functional in a host cell, such as a plant cell. Most preferably, the gene promoter and termination sequences are those of the original enzyme genes but others generally used in the art, such as the Cauliflower Mosaic Virus (CMV) promoter, with or without enhancers, such as the Kozak sequence or Omega enhancer, and *Agrobacterium tumefaciens* nopalin synthase terminator may be usefully employed in the present invention. Tissue-specific promoters may be employed in order to target expression to one or more desired tissues. The construct may further include a marker for the identification of transformed cells.

In a further aspect, transgenic cells, such as transgenic plant cells, comprising the constructs of the present invention are provided, together with tissues and plants comprising such transgenic cells, and fruits, seeds and other products, derivatives, or progeny of such plants.

In yet another aspect, methods for modulating the flowering of a target plant are provided. Such methods include stably incorporating into the genome of the target plant a genetic construct comprising a polynucleotide of the present invention. In a preferred embodiment, the target plant is a forage grass, preferably selected from the group consisting of *Lolium* and *Festuca* species, and most preferably from the group consisting of *Lolium perenne* and *Festuca arundinacea*.

In a related aspect, a method for producing a plant having altered flowering is provided, the method comprising transforming a plant cell with a genetic construct comprising a polynucleotide of the present invention to provide a transgenic cell, and cultivating the transgenic cell under conditions conducive to regeneration and mature plant growth.

In yet a further aspect, the present invention provides methods for modifying the activity of an enzyme in a target organism, such as a plant, comprising stably incorporating into the genome of the target organism a genetic construct of the present invention. In a preferred embodiment, the target plant is a forage grass, preferably selected from the group consisting of *Lolium* and *Festuca* species, and most preferably from the group consisting of *Lolium perenne* and *Festuca arundinacea*.

BRIEF DESCRIPTION OF THE DRAWINGS

FIG. 1 shows the amino acid sequence of SEQ ID NO: 21. The conserved dimerization domain of the SKP1 family is underlined.

FIG. 2 shows the amino acid sequence of SEQ ID NO: 22. The conserved dimerization domain of the SKP1 family is underlined.

FIG. 3 shows the amino acid sequence of SEQ ID NO: 23. The conserved dimerization domain of the SKP1 family is underlined.

FIG. 4 shows the amino acid sequence of SEQ ID NO: 24. The conserved RNA-binding region RNP-1 (RNA recognition motif) domains are underlined and the WW/Rsp5/WWP domain is in bold/italics.

FIG. 5 shows the amino acid sequence of SEQ ID NO: 25. The conserved RNA-binding region RNP-1 (RNA recognition motif) domains are underlined and the WW/Rsp5/WWP domain is in bold/italics.

FIG. 6 shows the amino acid sequence of SEQ ID NO: 26. The conserved phosphatidylethanolamine-binding protein (PBP) domain is underlined and the conserved PBP family signature is boxed.

FIG. 7 shows the amino acid sequence of SEQ ID NO: 27. The conserved phosphatidylethanolamine-binding protein (PBP) domain is underlined and the conserved PBP family signature is boxed.

FIG. 8 shows the amino acid sequence of SEQ ID NO: 28. The conserved GRAS family domain is underlined with conserved residues in the conserved C-terminus being in bold (Pysh et al., *Plant J.* 18:111-119, 1999).

FIG. 9 shows the amino acid sequence of SEQ ID NO: 29. Predicted transmembrane domains characteristic of GIGANTEA proteins (Fowler et al., *EMBO J.* 18:4679-4688, 1999) are underlined.

FIG. 10 shows the amino acid sequence of SEQ ID NO: 30. Predicted transmembrane domains, characteristic of GIGANTEA proteins (Fowler et al., *EMBO J.* 18:4679-4688, 1999) are underlined.

FIG. 11 shows the amino acid sequence of SEQ ID NO: 31. The conserved C2H2-type zinc finger is underlined with the conserved residues being boxed (Kubo et al., *Nucleic Acids Res.* 26:608-615, 1998).

FIG. 12 shows the amino acid sequence of SEQ ID NO: 32. The conserved C2H2-type zinc finger is underlined with the conserved residues being boxed (Kubo et al., *Nucleic Acids Res.* 26:608-615, 1998).

FIG. 13 shows the amino acid sequence of SEQ ID NO: 33. The conserved C2H2-type zinc finger is underlined with the conserved residues being boxed (Kubo et al., *Nucleic Acids Res.* 26:608-615, 1998).

FIG. 14 shows the amino acid sequence of SEQ ID NO: 34. The conserved G-protein beta WD-40 repeat domains are underlined and the conserved G-protein beta WD-40 repeat domain signature is boxed.

FIG. 15 shows the amino acid sequence of SEQ ID NO: 35. The conserved G-protein beta WD-40 repeat domains are underlined and the conserved G-protein beta WD-40 repeat domain signature is boxed.

FIG. 16 shows the amino acid sequence of SEQ ID NO: 36. The conserved phosphatidylethanolamine-binding protein (PBP) domain is underlined and the conserved PBP family signature is boxed.

FIG. 17 shows the amino acid sequence of SEQ ID NO: 37. A Gln-rich region is in bold/italics and a predicted transmembrane domain is double-underlined.

FIG. 18 shows the amino acid sequence of SEQ ID NO: 38. The conserved dimerization domain with similarity to the Ldb proteins (Franks et al., *Development* 129:253-263, 2002) is underlined. A Gln-rich region is in bold/italics.

FIG. 19 shows the amino acid sequence of SEQ ID NO: 39. The conserved dimerization domain with similarity to the Ldb proteins (Franks et al., *Development* 129:253-263, 2002) is underlined. A Gln-rich region is in bold/italics and a predicted transmembrane domain is double-underlined.

FIG. 20 shows the amino acid sequence of SEQ ID NO: 40. The conserved GRAS family domain is underlined with conserved residues in the conserved C-terminus is in bold (Pysh et al., *Plant J.* 18:111-119, 1999).

DETAILED DESCRIPTION OF THE INVENTION

Figure 21:
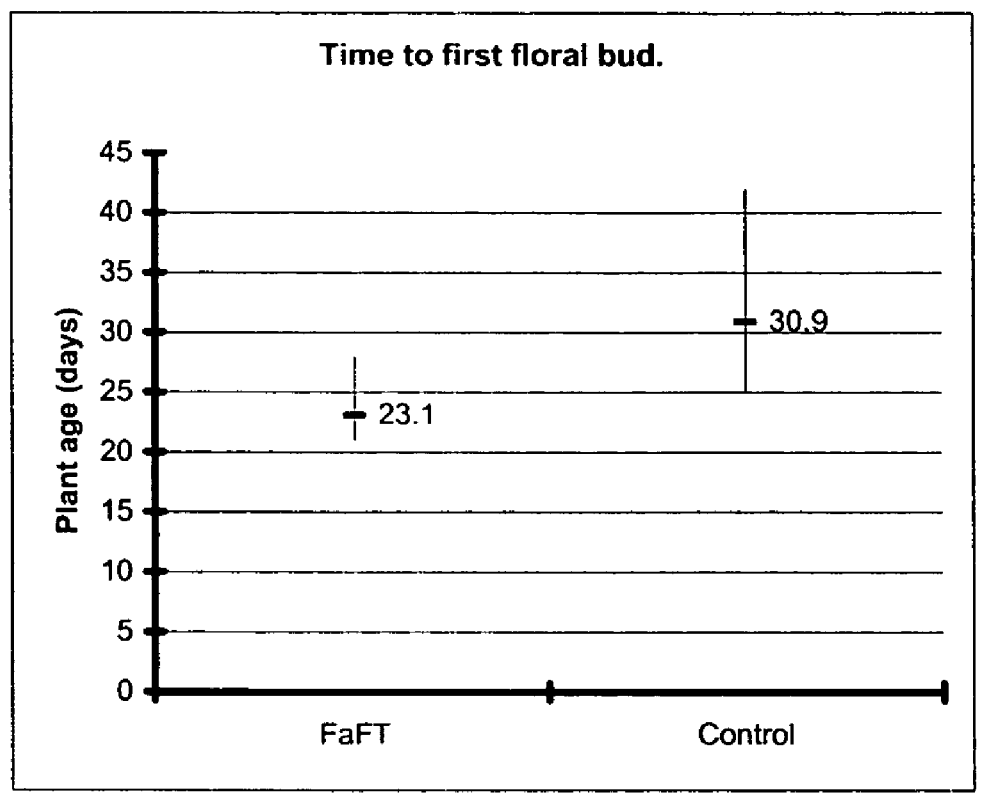
FIG. 21 shows the time to first floral bud formation for *Arabidopsis* plants over-expressing the grass flowering time gene FaFT (SEQ ID NO: 6) under long day conditions.

The polypeptides of the present invention, and the polynucleotides encoding the polypeptides, have activity in flowering pathways in plants. Using the methods and materials of the present invention, the transition to flowering in a plant may be modulated by modulating expression of polynucleotides of the present invention, or by modifying the polynucleotides or the polypeptides encoded by the polynucleotides.

The isolated polynucleotides and polypeptides of the present invention may be used to reduce lignin content, control flowering, induce flowering time, control spread of seed/pollen, and reduce spread of allergenic pollen. The main decrease in forage digestibility occurs around the time of flowering in grass plants when there is a sharp increase in syringyl lignin. This appears to be a defense mechanism by the plant to avoid being grazed whilst trying to reproduce. By controlling, or preventing, flowering in grasses, this decrease in forage digestibility can be avoided as there will be no increase in syringyl lignin. An added side effect of controlling or preventing flowering is that no pollen or seed will produced. This in turn will reduce the uncontrolled spread of genetically modified organisms, as well as reduce the amount of pollen produced. Ryegrass pollen is one of the most common allergens leading to hay fever in humans (Bhalla et al., *Proc. Nat. Acad. Sci. USA* 96:11676-11680, 1999). In addition, by linking the flowering control genes of the present invention to an inducible promoter, the timing of flowering can be accurately controlled.

The flowering of a plant may be modified by incorporating additional copies of flower control genes of the present invention into the genome of the target plant, or by transforming the target plant with anti-sense copies of such flower control genes. In addition, the number of copies of flowering genes can be manipulated to alter the time of transition from vegetative to floral state.

The present invention thus provides methods for modulating the polynucleotide and/or polypeptide content and composition of a target organism, such methods involving stably incorporating into the genome of the organism a genetic construct comprising one or more polynucleotides of the present invention. In one embodiment, the target organism is a plant species, preferably a forage plant, more preferably a grass of the *Lolium* or *Festuca* species, and most preferably *Lolium perenne* or *Festuca arundinacea*. In related aspects, methods for producing a plant having an altered genotype or phenotype are provided, such methods comprising transforming a plant cell with a genetic construct of the present invention to provide a transgenic cell, and cultivating the transgenic cell under conditions conducive to regeneration and mature plant growth. Plants having an altered genotype or phenotype as a consequence of modulation of the level or content of a polynucleotide or polypeptide of the present invention compared to a wild-type organism, as well as components (seeds, etc.) of such plants, and the progeny of such plants, are contemplated by and encompassed within the present invention.

The isolated polynucleotides of the present invention also have utility in genome mapping, in physical mapping, and in positional cloning of genes. Additionally, the polynucleotide sequences identified as SEQ ID NO: 1-20 and their variants, may be used to design oligonucleotide probes and primers. Oligonucleotide probes and primers have sequences that are substantially complementary to the polynucleotide of interest over a certain portion of the polynucleotide. Oligonucleotide probes designed using the polynucleotides of the present invention may be employed to detect the presence and examine the expression patterns of genes in any organism having sufficiently similar DNA and RNA sequences in their cells using techniques that are well known in the art, such as slot blot DNA hybridization techniques. Oligonucleotide primers designed using the polynucleotides of the present invention may be used for PCR amplifications. Oligonucleotide probes and primers designed using the polynucleotides of the present invention may also be used in connection with various microarray technologies, including the microarray technology of Affymetrix Inc. (Santa Clara, Calif.).

In a first aspect, the present invention provides isolated polynucleotide sequences identified in the attached Sequence Listing as SEQ ID NO: 1-20 and isolated polypeptide sequences identified in the attached Sequence Listing as SEQ ID NO: 21-40. The polynucleotides and polypeptides of the present invention have demonstrated similarity to the following polypeptides that are known to be involved in flowering pathways:

TABLE 1

| SEQ ID NO: DNA | SEQ ID NO: polypeptide | Category | Description |
|---|---|---|---|
| 1-3 | 21-23 | Transcriptional regulation/ Floral development | Homologs isolated from *L. perenne* of ASK1 (*Arabidopsis* SKP-like), which regulates B function gene expression in cooperation with UFO and LFY in *Arabidopsis* (Zhao et al, Development 128: 2735-2746, 2001). |

TABLE 1-continued

| SEQ ID NO: DNA | SEQ ID NO: polypeptide | Category | Description |
|---|---|---|---|
| 4 | 24 | Transcriptional regulation/ Floral development | Homolog isolated from *F. arundinacea* of the *Arabidopsis thaliana* transcription factor FCA that is involved in control of flowering time. FCA encodes a RNA binding protein. The protein contains two RNA-binding domains and a WW protein interaction domain suggesting that FCA functions in the posttranscriptional regulation of transcripts involved in the flowering process. FCA appears to be a component of a posttranscriptional cascade involved in the control of flowering time (Koornneef, Curr. Biol. 7: R651-652, 1997). |
| 5 | 25 | Transcriptional regulation/ Floral development | Homolog isolated from *L. perenne* of the *Arabidopsis thaliana* transcription factor FCA that is involved in control of flowering time. FCA encodes a RNA binding protein. The protein contains two RNA-binding domains and a WW protein interaction domain suggesting that FCA functions in the posttranscriptional regulation of transcripts involved in the flowering process. FCA appears to be a component of a posttranscriptional cascade involved in the control of flowering time (Koornneef, Curr. Biol. 7: R651-652, 1997). |
| 6 | 26 | Transcriptional regulation/ Floral development | Homolog isolated from *F. arundinacea* of the Flowering locus T (FT), which together with "Suppression of overexpression of CO1" (SOC1) interacts with *Arabidopsis* CO to promote flowering in response to day length. Ft and Soc1 can act independently of CO, putatively by acting within a different flowering-time pathway (Samach et al, Science 288: 1613-1616, 2000). |
| 7 | 27 | Transcriptional regulation/ Floral development | Homolog isolated from *L. perenne* of the Flowering locus T (FT), which together with "Suppression of overexpression of CO1" (SOC1) interacts with *Arabidopsis* CO to promote flowering in response to day length. Ft and Soc1 can act independently of CO, putatively by acting within a different flowering-time pathway (Samach et al, Science 288: 1613-1616, 2000). |
| 8 | 28 | Transcriptional regulation/ Floral development | Homolog isolated from *L. perenne* of the *Arabidopsis thaliana* GIBBERELLIN INSENSITIVE (GAI) gene that is involved in developmental processes including seed development and germination, flower and fruit development and flowering time. Genetic studies with *A. thaliana* have identified two genes involved in GA perception or signal transduction. A semidominant mutation at the GAI locus results in plants resembling GA-deficient mutants but exhibiting reduced sensitivity to GA (Jacobsen et al., Proc. Natl. Acad. Sci. USA 93: 9292-9296, 1996). |
| 9 | 29 | Transcriptional regulation/DNA binding/ Flowering control | Homolog isolated from *L. perenne* of the *Arabidopsis thaliana* GIGANTEA (GI) gene that is involved in control of flowering time. GI is a nucleoplasmically localized protein involved in phytochrome signaling (Huq et al., Proc. Natl. Acad. Sci. USA 97: 9789-9794, 2000). Flowering of *Arabidopsis* is promoted by long days and delayed by short days. GI expression is regulated by the circadian clock GI plays an important role in regulating the expression of flowering time genes during the promotion of flowering by photoperiod (Fowler et al., EMBO J. 18: 4679-4688, 1999). |
| 10 | 30 | Transcriptional regulation/DNA binding/ Flowering control | Homolog isolated from *F. arundinacea* of the *Arabidopsis thaliana* GIGANTEA (GI) gene that is involved in control of flowering time. GI is a nucleoplasmically localized protein involved in phytochrome signaling (Huq et al., Proc. Natl. Acad. Sci. USA 97: 9789-9794, 2000). Flowering of *Arabidopsis* is promoted by long days and delayed by short days. GI expression is regulated by the circadian clock GI plays an important role |

TABLE 1-continued

| SEQ ID NO: DNA | SEQ ID NO: polypeptide | Category | Description |
|---|---|---|---|
| | | | in regulating the expression of flowering time genes during the promotion of flowering by photoperiod (Fowler et al., EMBO J. 18: 4679-4688, 1999). |
| 11 | 31 | Transcriptional regulation/DNA binding/ Flowering development | Homolog isolated from *F. arundinacea* of the maize Indeterminate1 gene (ID1) that controls the transition to flowering. ID1 encodes a protein with zinc finger motifs and functions as a transcriptional regulator of the floral transition (Colasanti et al., Cell 93: 593-603, 1998). |
| 12 | 32 | Transcriptional regulation/DNA binding/ Flowering development | Homolog isolated from *L. perenne* of the maize Indeterminate1 gene (ID1) that controls the transition to flowering. ID1 encodes a protein with zinc finger motifs and functions as a transcriptional regulator of the floral transition (Colasanti et al., Cell 93: 593-603, 1998). |
| 13 | 33 | Transcriptional regulation/DNA binding/ Flowering development | Homolog isolated from *F. arundinacea* of the maize Indeterminate1 gene (ID1) that controls the transition to flowering. ID1 encodes a protein with zinc finger motifs and functions as a transcriptional regulator of the floral transition (Colasanti et al., Cell 93: 593-603, 1998). |
| 14,15 | 34,35 | Transcriptional regulation/ Floral development | Homolog isolated from *F. arundinacea* of LEUNIG, a key regulator of the *Arabidopsis* floral homeotic gene AGAMOUS. LEUNIG encodes a glutamine-rich protein with seven WD repeats and is similar in motif structure to a class of functionally related transcriptional co-repressors. The nuclear localization of LEUNIG is consistent with a role of LEUNIG as a transcriptional regulator (Conner and Liu, Proc. Natl. Acad. Sci. USA 97: 12902-12907, 2000). Another regulatory gene, SEUSS, has been identified that functions together with LEUNIG to regulate AGAMOUS (Franks et al, Development 129: 253-263, 2002). |
| 16 | 36 | Transcriptional regulation/ Floral development | Homolog isolated from *F. arundinacea* of the *Arabidopsis* TERMINAL FLOWER1 (TFL1) gene involved in initiation of flowering. TFKL1 is controlled by the MADS box proteins CAULIFLOWER, LEAFY and APETALA1 (Liljegren et al, Plant Cell 11: 1007-1018, 1999). |
| 17-19 | 37-39 | Transcriptional regulation/ Floral development | Homologs isolated from *F. arundinacea* of the SEUSS transcription factor that plays a role in regulation of plant development. The SEUSS protein contains two glutamine-rich domains and a conserved domain with similarity to dimerization domain of the LIM-domain-binding transcription co-regulators in animals. SEUSS encodes a regulator of AGAMOUS and functions together with LEUNIG (Franks et al., Development. 129: 253-263, 2002). |
| 20 | 40 | Transcriptional regulation/ Floral development | Homolog isolated from *F. arundinacea* of the *Arabidopsis thaliana* GIBBERELLIN INSENSITIVE (GAI) gene that is involved in developmental processes including seed development and germination, flower and fruit development and flowering time. Genetic studies with *A. thaliana* have identified two genes involved in GA perception or signal transduction. A semidominant mutation at the GAI locus results in plants resembling GA-deficient mutants but exhibiting reduced sensitivity to GA (Jacobsen et al., Proc. Natl. Acad. Sci. USA 93: 9292-9296, 1996). |

All the polynucleotides and polypeptides provided by the present invention are isolated and purified, as those terms are commonly used in the art. Preferably, the polypeptides and polynucleotides are at least about 80% pure, more preferably at least about 90% pure, and most preferably at least about 99% pure.

The word "polynucleotide(s)," as used herein, means a polymeric collection of nucleotides, and includes DNA and corresponding RNA molecules and both single and double stranded molecules, including HnRNA and mRNA molecules, sense and anti-sense strands of DNA and RNA molecules, and comprehends cDNA, genomic DNA, and wholly or partially synthesized polynucleotides.

In analyzing the phloem-mobile RNA populations of cucurbits, the presence of microRNA-like molecules (miRNAs) in phloem sap and vascular strands of cucurbits has been detected. miRNAs have been reported in other organisms including *C. elegans, Drosophila* and humans, and are proposed to act as regulators of processes involved in early development and synaptic plasticity of neurons (for a review see Ruvkun, *Science* 294:797, 1999). These small RNAs are derived from double-stranded RNA precursors by cellular machinery that produces small RNAs associated with PTGS/RNAi (Hutvagner et al., *Science* 293:834-838, 2001; Grishok et al., *Cell* 106: 23-34, 2001). The presence of this small RNA population in phloem sap of plants suggests that miRNA may play a regulatory role in flowering and other processes that act systemically using long distance signaling mechanisms.

While not wishing to be held to theory, the inventors believe that the small RNA population of the phloem is produced by components of cellular processes involved in the maturation of siRNA (Hamilton and Baulcombe, *Science* 286:950-952, 1999). These components may include homologs of the plant genes Argonaute (Bohmert et al., *EMBO J.* 17:170-180, 1998), Carpel Factory (Jacobsen et al., *Development* 126:5231-5243 1999); SDE1/SGS2 (Mourrain, *Cell* 101:533-542, 2000; Dalmay et al., *Cell* 101:543-553, 2000) and SDE3 (Dalmay et al., *EMBO J.* 20:2069-2078, 2001). miRNAs corresponding to the inventive polynucleotide sequences are contemplated by the present invention and encompassed within the term "polynucleotide".

A polynucleotide of the present invention may be an entire gene or any portion thereof. As used herein, a "gene" is a DNA sequence that codes for a functional protein or RNA molecule. Operable anti-sense polynucleotides may comprise a fragment of the corresponding polynucleotide, and the definition of "polynucleotide" therefore includes all operable anti-sense fragments. Anti-sense polynucleotides and techniques involving anti-sense polynucleotides are well known in the art and are described, for example, in Robinson-Benion et al., *Methods in Enzymol.* 254:363-375, 1995 and Kawasaki et al., *Artific. Organs* 20:836-848, 1996.

In specific embodiments, the present invention provides isolated polynucleotides comprising a sequence of SEQ ID NO: 1-20; polynucleotides comprising variants of SEQ ID NO: 1-20; polynucleotides comprising extended sequences of SEQ ID NO: 1-20 and their variants, oligonucleotide primers and probes corresponding to the sequences set out in SEQ ID NO: 1-20 and their variants, polynucleotides comprising at least a specified number of contiguous residues of any of SEQ ID NO: 1-20 (x-mers), and polynucleotides comprising extended sequences which include portions of the sequences set out in SEQ ID NO: 1-20, all of which are referred to herein, collectively, as "polynucleotides of the present invention." Polynucleotides that comprise complements of such polynucleotide sequences, reverse complements of such polynucleotide sequences, or reverse sequences of such polynucleotide sequences, together with variants of such sequences, are also provided.

The definition of the terms "complement(s)," "reverse complement(s)," and "reverse sequence(s)," as used herein, is best illustrated by the following example. For the sequence 5' AGGACC 3', the complement, reverse complement, and reverse sequence are as follows:

```
complement              3' TCCTGG 5'
reverse complement      3' GGTCCT 5'
reverse sequence        5' CCAGGA 3'.
```

Preferably, sequences that are complements of a specifically recited polynucleotide sequence are complementary over the entire length of the specific polynucleotide sequence.

As used herein, the term "x-mer," with reference to a specific value of "x," refers to a polynucleotide comprising at least a specified number ("x") of contiguous residues of: any of the polynucleotides provided in SEQ ID NO: 1-20. The value of x may be from about 20 to about 600, depending upon the specific sequence.

Polynucleotides of the present invention comprehend polynucleotides comprising at least a specified number of contiguous residues (x-mers) of any of the polynucleotides identified as SEQ ID NO: 1-20, or their variants. Similarly, polypeptides of the present invention comprehend polypeptides comprising at least a specified number of contiguous residues (x-mers) of any of the polypeptides identified as SEQ ID NO: 21-40. According to preferred embodiments, the value of x is at least 20, more preferably at least 40, more preferably yet at least 60, and most preferably at least 80. Thus, polynucleotides of the present invention include polynucleotides comprising a 20-mer, a 40-mer, a 60-mer, an 80-mer, a 100-mer, a 120-mer, a 150-mer, a 180-mer, a 220-mer, a 250-mer; or a 300-mer, 400-mer, 500-mer or 600-mer of a polynucleotide provided in SEQ ID NO: 1-20, or a variant of one of the polynucleotides corresponding to the polynucleotides provided in SEQ ID NO: 1-20. Polypeptides of the present invention include polypeptides comprising a 20-mer, a 40-mer, a 60-mer, an 80-mer, a 100-mer, a 120-mer, a 150-mer, a 180-mer, a 220-mer, a 250-mer; or a 300-mer, 400-mer, 500-mer or 600-mer of a polypeptide provided in SEQ ID NO: 21-40, or a variant thereof.

Polynucleotides of the present invention were isolated by high throughput sequencing of cDNA libraries comprising forage grass tissue collected from *Lolium perenne* and *Festuca arundinacea*. Some of the polynucleotides of the present invention may be "partial" sequences, in that they do not represent a full-length gene encoding a full-length polypeptide. Such partial sequences may be extended by analyzing and sequencing various DNA libraries using primers and/or probes and well known hybridization and/or PCR techniques. Partial sequences may be extended until an open reading frame encoding a polypeptide, a full-length polynucleotide and/or gene capable of expressing a polypeptide, or another useful portion of the genome is identified. Such extended sequences, including full-length polynucleotides and genes, are described as "corresponding to" a sequence identified as one of the sequences of SEQ ID NO: 1-20 or a variant thereof, or a portion of one of the sequences of SEQ ID NO: 1-20 or a variant thereof, when the extended polynucleotide comprises an identified sequence or its variant, or an identified contiguous portion (x-mer) of one of the sequences of SEQ ID NO: 1-20 or a variant thereof. Similarly, RNA sequences, reverse sequences, complementary sequences, anti-sense sequences and the like, corresponding to the polynucleotides of the present invention, may be routinely ascertained and obtained using the cDNA sequences identified as SEQ ID NO: 1-20.

The polynucleotides identified as SEQ ID NO: 1-20 may contain open reading frames ("ORFs") or partial open reading frames encoding polypeptides and functional portions of polypeptides. Partial open reading frames are encoded by SEQ ID NO: 3-5, 7, 8, 17 and 19, while SEQ ID NO: 1, 2, 6, 9-16, 18 and 20 represent full-length sequences. Additionally, open reading frames encoding polypeptides may be identified in extended or full-length sequences corresponding to the sequences disclosed herein. Open reading frames may be identified using techniques that are well known in the art. These techniques include, for example, analysis for the location of known start and stop codons, most likely reading frame identification based on codon frequencies, etc. These techniques include, for example, analysis for the location of known start and stop codons, most likely reading frame identification based on codon frequencies, etc. Suitable tools and software for ORF analysis are well known in the art and include, for example, GeneWise, available from The Sanger Center, Wellcome Trust Genome Campus, Hinxton, Cambridge, CB 10 1SA, United Kingdom; Diogenes, available from Computational Biology Centers, University of Minnesota, Academic Health Center, UMHG Box 43 Minneapolis Minn. 55455; and GRAIL, available from the Informatics Group, Oak Ridge National Laboratories, Oak Ridge, Tenn. Once a partial open reading frame is identified, the polynucleotide may be extended in the area of the partial open reading frame using techniques that are well known in the art until the polynucleotide for the full open reading frame is identified.

Once open reading frames are identified in the polynucleotides of the present invention, the open reading frames may be isolated and/or synthesized. Expressible genetic constructs comprising the open reading frames and suitable promoters, initiators, terminators, etc., which are well known in the art, may then be constructed. Such genetic constructs may be introduced into a host cell to express the polypeptide encoded by the open reading frame. Suitable host cells may include various prokaryotic and eukaryotic cells, including plant cells, mammalian cells, bacterial cells, algae and the like.

The polynucleotides of the present invention may be isolated by high throughput sequencing of cDNA libraries prepared from forage grass tissue, as described below in Example 1. Alternatively, oligonucleotide probes and primers based on the sequences provided in SEQ ID NO: 1-20 can be synthesized as detailed below, and used to identify positive clones in either cDNA or genomic DNA libraries from forage grass tissue cells by means of hybridization or polymerase chain reaction (PCR) techniques. Hybridization and PCR techniques suitable for use with such oligonucleotide probes are well known in the art (see, for example, Mullis et al., *Cold Spring Harbor Symp. Quant. Biol.*, 51:263, 1987; Erlich, ed., *PCR technology*, Stockton Press: NY, 1989; and Sambrook et al., eds., *Molecular cloning: a laboratory manual*, 2nd ed., CSHL Press: Cold Spring Harbor, N.Y., 1989). In addition to DNA-DNA hybridization, DNA-RNA or RNA-RNA hybridization assays are also possible. In the first case, the mRNA from expressed genes would then be detected instead of genomic DNA or cDNA derived from mRNA of the sample. In the second case, RNA probes could be used. Artificial analogs of DNA hybridizing specifically to target sequences could also be employed. Positive clones can be analyzed by using restriction enzyme digestion, DNA sequencing or the like.

The polynucleotides of the present invention may also, or alternatively, be synthesized using techniques that are well known in the art. The polynucleotides may be synthesized, for example, using automated oligonucleotide synthesizers (e.g., Beckman Oligo 1000M DNA Synthesizer; Beckman Coulter Ltd., Fullerton, Calif.) to obtain polynucleotide segments of up to 50 or more nucleic acids. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleic acids, and hybridizing that segment to a synthesized complementary 85 nucleic acid segment to produce a 5 nucleotide overhang. The next segment may then be synthesized in a similar fashion, with a 5 nucleotide overhang on the opposite strand. The "sticky" ends ensure proper ligation when the two portions are hybridized. In this way, a complete polynucleotide of the present invention may be synthesized entirely in vitro.

Oligonucleotide probes and primers complementary to and/or corresponding to SEQ ID NO: 1-20 and variants of those sequences, are also comprehended by the present invention. Such oligonucleotide probes and primers are substantially complementary to the polynucleotide of interest over a certain portion of the polynucleotide. An oligonucleotide probe or primer is described as "corresponding to" a polynucleotide of the present invention, including one of the sequences set out as SEQ ID NO: 1-20 or a variant thereof, if the oligonucleotide probe or primer, or its complement, is contained within one of the sequences set out as SEQ ID NO: 1-20 or a variant of one of the specified sequences.

Two single stranded sequences are said to be substantially complementary when the nucleotides of one strand, optimally aligned and compared, with the appropriate nucleotide insertions and/or deletions, pair with at least 80%, preferably at least 90% to 95%, and more preferably at least 98% to 100%, of the nucleotides of the other strand. Alternatively, substantial complementarity exists when a first DNA strand will selectively hybridize to a second DNA strand under stringent hybridization conditions.

In specific embodiments, the oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length, preferably from about 10 to 50 base pairs in length, and more preferably from about 15 to 40 base pairs in length. The probes can be easily selected using procedures well known in the art, taking into account DNA-DNA hybridization stringencies, annealing and melting temperatures, potential for formation of loops, and other factors that are well known in the art. Preferred techniques for designing PCR primers are disclosed in Dieffenbach and Dyksler, *PCR Primer: a laboratory manual*, CSHL Press: Cold Spring Harbor, N.Y., 1995. A software program suitable for designing probes, and especially for designing PCR primers, is available from Premier Biosoft International, 3786 Corina Way, Palo Alto, Calif. 94303-4504.

The isolated polynucleotides of the present invention also have utility in genome mapping, in physical mapping, and in positional cloning of genes.

The polynucleotides identified as SEQ ID NO: 1-20 were isolated from cDNA clones and represent sequences that are expressed in the tissue from which the cDNA was prepared. RNA sequences, reverse sequences, complementary sequences, anti-sense sequences, and the like, corresponding to the polynucleotides of the present invention, may be routinely ascertained and obtained using the cDNA sequences identified as SEQ ID NO: 1-20.

Identification of genomic DNA and heterologous species DNA can be accomplished by standard DNA/DNA hybridization techniques, under appropriately stringent conditions, using all or part of a polynucleotide sequence as a probe to screen an appropriate library. Alternatively, PCR techniques using oligonucleotide primers that are designed based on known genomic DNA, cDNA and protein sequences can be used to amplify and identify genomic and cDNA sequences.

In another aspect, the present invention provides isolated polypeptides encoded by the above polynucleotides. As used herein, the term "polypeptide" encompasses amino acid chains of any length, including full-length proteins, wherein the amino acid residues are linked by covalent peptide bonds. The term "polypeptide encoded by a polynucleotide" as used herein, includes polypeptides encoded by a polynucleotide that comprises a partial isolated polynucleotide sequence provided herein. In specific embodiments, the inventive polypeptides comprise an amino acid sequence selected from the group consisting of SEQ ID NO: 21-40, as well as variants of such sequences.

As noted above, polypeptides of the present invention may be produced recombinantly by inserting a polynucleotide sequence of the present invention encoding the polypeptide into an expression vector and expressing the polypeptide in an appropriate host. Any of a variety of expression vectors known to those of ordinary skill in the art may be employed. Expression may be achieved in any appropriate host cell that has been transformed or transfected with an expression vector containing a polynucleotide molecule that encodes a recombinant polypeptide. Suitable host cells include prokaryotes, yeast, and higher eukaryotic cells. Preferably, the host cells employed are plant, *E. coli*, insect, yeast, or a mammalian cell line such as COS or CHO. The polynucleotide sequences expressed in this manner may encode naturally occurring polypeptides, portions of naturally occurring polypeptides, or other variants thereof. The expressed polypeptides may be used in various assays known in the art to determine their biological activity. Such polypeptides may also be used to raise antibodies, to isolate corresponding interacting proteins or other compounds, and to quantitatively determine levels of interacting proteins or other compounds.

In a related aspect, polypeptides are provided that comprise at least a functional portion of a polypeptide having an amino acid sequence selected from the group consisting of sequences provided in SEQ ID NO: 21-40 and variants thereof. As used herein, the "functional portion" of a polypeptide is that portion which contains an active site essential for affecting the function of the polypeptide, for example, a portion of the molecule that is capable of binding one or more reactants. The active site may be made up of separate portions present on one or more polypeptide chains and will generally exhibit high binding affinity. Functional portions of a polypeptide may be identified by first preparing fragments of the polypeptide by either chemical or enzymatic digestion of the polypeptide, or by mutation analysis of the polynucleotide that encodes the polypeptide and subsequent expression of the resulting mutant polypeptides. The polypeptide fragments or mutant polypeptides are then tested to determine which portions retain biological activity, using methods well known to those of skill in the art, including the representative assays described below.

Portions and other variants of the inventive polypeptides may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149-2146, 1963. Equipment for automated synthesis of polypeptides is commercially available from suppliers such as Perkin Elmer/Applied Biosystems, Inc. (Foster City, Calif.), and may be operated according to the manufacturer's instructions. Variants of a native polypeptide may be prepared using standard mutagenesis techniques, such as oligonucleotide-directed site-specific mutagenesis (Kunkel, *Proc. Natl. Acad. Sci. USA* 82:488-492, 1985). Sections of DNA sequences may also be removed using standard techniques to permit preparation of truncated polypeptides.

As used herein, the term "variant" comprehends nucleotide or amino acid sequences different from the specifically identified sequences, wherein one or more nucleotides or amino acid residues is deleted, substituted, or added. Variants may be naturally occurring allelic variants, or non-naturally occurring variants. Variant sequences (polynucleotide or polypeptide) preferably exhibit at least 75%, more preferably at least 80%, more preferably at least 90%, more preferably yet at least 95% and most preferably, at least 98% identity to a sequence of the present invention. The percentage identity is determined by aligning the two sequences to be compared as described below, determining the number of identical residues in the aligned portion, dividing that number by the total number of residues in the inventive (queried) sequence, and multiplying the result by 100.

Polynucleotides and polypeptides having a specified percentage identity to a polynucleotide or polypeptide identified in one of SEQ ID NO: 1-40 thus share a high degree of similarity in their primary structure. In addition to a specified percentage identity to a polynucleotide of the present invention, variant polynucleotides and polypeptides preferably have additional structural and/or functional features in common with a polynucleotide of the present invention. Polynucleotides having a specified degree of identity to, or capable of hybridizing to, a polynucleotide of the present invention preferably additionally have at least one of the following features: (1) they contain an open reading frame, or partial open reading frame, encoding a polypeptide, or a functional portion of a polypeptide, having substantially the same functional properties as the polypeptide, or functional portion thereof, encoded by a polynucleotide in a recited SEQ ID NO.; or (2) they contain identifiable domains in common.

Polynucleotide or polypeptide sequences may be aligned, and percentages of identical nucleotides or amino acids in a specified region may be determined against another polynucleotide or polypeptide, using computer algorithms that are publicly available. The BLASTN and FASTA algorithms, set to the default parameters described in the documentation and distributed with the algorithm, may be used for aligning and identifying the similarity of polynucleotide sequences. The alignment and similarity of polypeptide sequences may be examined using the BLASTP algorithm. BLASTX and FASTX algorithms compare nucleotide query sequences translated in all reading frames against polypeptide sequences. The FASTA and FASTX algorithms are described in Pearson and Lipman, *Proc. Natl. Acad. Sci. USA* 85:2444-2448, 1988; and in Pearson, *Methods in Enzymol.* 183:63-98, 1990. The FASTA software package is available from the University of Virginia by contacting the Assistant Provost for Research, University of Virginia, PO Box 9025, Charlottesville, Va. 22906-9025. The BLASTN software is available from the National Center for Biotechnology Information (NCBI), National Library of Medicine, Building 38A, Room 8N805, Bethesda, Md. 20894. The BLASTN algorithm Version 2.0.11 [Jan. 20, 2000] set to the default parameters described in the documentation and distributed with the algorithm, is preferred for use in the determination of polynucleotide variants according to the present invention. The use of the BLAST family of algorithms, including BLASTN, BLASTP and BLASTX, is described in the publication of Altschul et al., "Gapped BLAST and PSI-BLAST: a new generation of protein database search programs," *Nucleic Acids Res.* 25:3389-3402, 1997.

The following running parameters are preferred for determination of alignments and similarities using BLASTN that contribute to the E values and percentage identity for polynucleotides: Unix running command with the following default parameters: blastall -p blastn -d embldb -e 10 -G 0 -E 0 -FF -r 1 -v 30 -b 30 -i queryseq -o results; and parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -FF low complexity filter; -r Reward for a nucleotide match (BLASTN only) [Integer]; -v Number of one-line descriptions (V) [Integer]; -b Number of alignments to show (B) [Integer]; -i Query File [File In]; -o BLAST report Output File [File Out] Optional.

The following running parameters are preferred for determination of alignments and similarities using BLASTP that contribute to the E values and percentage identity of polypeptide sequences: blastall -p blastp -d swissprottrembledb -e 10-G 0-E 0-FF -v 30-b 30-i queryseq -o results; the parameters are: -p Program Name [String]; -d Database [String]; -e Expectation value (E) [Real]; -G Cost to open a gap (zero invokes default behavior) [Integer]; -E Cost to extend a gap (zero invokes default behavior) [Integer]; -FF low complexity filter; -v Number of one-line descriptions (v) [Integer]; -b Number of alignments to show (b) [Integer]; -I Query File [File In]; -o BLAST report Output File [File Out] Optional.

The "hits" to one or more database sequences by a queried sequence produced by BLASTN, BLASTP, FASTA, or a similar algorithm, align and identify similar portions of sequences. The hits are arranged in order of the degree of similarity and the length of sequence overlap. Hits to a database sequence generally represent an overlap over only a fraction of the sequence length of the queried sequence.

As noted above, the percentage identity of a polynucleotide or polypeptide sequence is determined by aligning polynucleotide and polypeptide sequences using appropriate algorithms, such as BLASTN or BLASTP, respectively, set to default parameters; identifying the number of identical nucleic or amino acids over the aligned portions; dividing the number of identical nucleic or amino acids by the total number of nucleic or amino acids of the polynucleotide or polypeptide of the present invention; and then multiplying by 100 to determine the percentage identity. By way of example, a queried polynucleotide having 220 nucleic acids has a hit to a polynucleotide sequence in the EMBL database having 520 nucleic acids over a stretch of 23 nucleotides in the alignment produced by the BLASTN algorithm using the default parameters. The 23-nucleotide hit includes 21 identical nucleotides, one gap and one different nucleotide. The percentage identity of the queried polynucleotide to the hit in the EMBL database is thus 21/220 times 100, or 9.5%. The percentage identity of polypeptide sequences may be determined in a similar fashion.

The BLASTN and BLASTX algorithms also produce "Expect" values for polynucleotide and polypeptide alignments. The Expect value (E) indicates the number of hits one can "expect" to see over a certain number of contiguous sequences by chance when searching a database of a certain size. The Expect value is used as a significance threshold for determining whether the hit to a database indicates true similarity. For example, an E value of 0.1 assigned to a polynucleotide hit is interpreted as meaning that in a database of the size of the EMBL database, one might expect to see 0.1 matches over the aligned portion of the sequence with a similar score simply by chance. By this criterion, the aligned and matched portions of the sequences then have a probability of 90% of being related. For sequences having an E value of 0.01 or less over aligned and matched portions, the probability of finding a match by chance in the EMBL database is 1% or less using the BLASTN algorithm. E values for polypeptide sequences may be determined in a similar fashion using various polypeptide databases, such as the SwissProt-TrEMBLE database.

According to one embodiment, "variant" polynucleotides and polypeptides, with reference to each of the polynucleotides and polypeptides of the present invention, preferably comprise sequences having the same number or fewer nucleotides or amino acids than each of the polynucleotides or polypeptides of the present invention and producing an E value of 0.01 or less when compared to the polynucleotide or polypeptide of the present invention. That is, a variant polynucleotide or polypeptide is any sequence that has at least a 99% probability of being related to the polynucleotide or polypeptide of the present invention, measured as having an E value of 0.01 or less using the BLASTN or BLASTX algorithms set at the default parameters. According to a preferred embodiment, a variant polynucleotide is a sequence having the same number or fewer nucleic acids than a polynucleotide of the present invention that has at least a 99% probability of being related to the polynucleotide of the present invention, measured as having an E value of 0.01 or less using the BLASTN algorithm set at the default parameters. Similarly, according to a preferred embodiment, a variant polypeptide is a sequence having the same number or fewer amino acids than a polypeptide of the present invention that has at least a 99% probability of being related as the polypeptide of the present invention, measured as having an E value of 0.01 or less using the BLASTP algorithm set at the default parameters.

In an alternative embodiment, variant polynucleotides are sequences that hybridize to a polynucleotide of the present invention under stringent conditions. Stringent hybridization conditions for determining complementarity include salt conditions of less than about 1 M, more usually less than about 500 mM, and preferably less than about 200 mM. Hybridization temperatures can be as low as 5° C., but are generally greater than about 22° C., more preferably greater than about 30° C., and most preferably greater than about 37° C. Longer DNA fragments may require higher hybridization temperatures for specific hybridization. Since the stringency of hybridization may be affected by other factors such as probe composition, presence of organic solvents, and extent of base mismatching, the combination of parameters is more important than the absolute measure of any one alone. An example of "stringent conditions" is prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The present invention also encompasses polynucleotides that differ from the disclosed sequences but that, as a consequence of the discrepancy of the genetic code, encode a polypeptide having similar enzymatic activity to a polypeptide encoded by a polynucleotide of the present invention. Thus, polynucleotides comprising sequences that differ from the polynucleotide sequences recited in SEQ ID NO: 1-20, or complements, reverse sequences, or reverse complements of those sequences, as a result of conservative substitutions are contemplated by and encompassed within the present invention. Additionally, polynucleotides comprising sequences that differ from the polynucleotide sequences recited in SEQ ID NO: 1-20, or complements, reverse complements or reverse sequences thereof, as a result of deletions and/or insertions totaling less than 10% of the total sequence length are also contemplated by and encompassed within the present invention. Similarly, polypeptides comprising sequences that differ from the polypeptide sequences recited in SEQ ID NO: 21-40 as a result of amino acid substitutions, insertions, and/ or deletions totaling less than 10% of the total sequence length are contemplated by and encompassed within the present invention, provided the variant polypeptide has activity in a flowering pathway.

In another aspect, the present invention provides genetic constructs comprising, in the 5'-3' direction, a gene promoter sequence; an open reading frame coding for at least a functional portion of a polypeptide of the present invention; and a gene termination sequence. The open reading frame may be orientated in either a sense or anti-sense direction. For applications where amplification of enzyme activity is desired, the open reading frame may be inserted in the construct in a sense orientation, such that transformation of a target organism with the construct will lead to an increase in the number of copies of the gene and therefore an increase in the amount of enzyme. When down-regulation of enzyme activity is desired, the open reading frame may be inserted in the construct in an anti-sense orientation, such that the RNA produced by transcription of the polynucleotide is complementary to the endogenous mRNA sequence. This, in turn, will result in a decrease in the number of copies of the gene and therefore a decrease in the amount of enzyme. Alternatively, regulation may be achieved by inserting appropriate sequences or subsequences (e.g., DNA or RNA) in ribozyme constructs.

Genetic constructs comprising a non-coding region of a gene coding for a polypeptide of the present invention, or a nucleotide sequence complementary to a non-coding region, together with a gene promoter sequence and a gene termination sequence, are also provided. As used herein the term "non-coding region" includes both transcribed sequences that are not translated, and non-transcribed sequences within about 2000 base pairs 5' or 3' of the translated sequences or open reading frames. Examples of non-coding regions that may be usefully employed in the inventive constructs include introns and 5'-non-coding leader sequences. Transformation of a target plant with such a genetic construct may lead to a reduction in the amount of enzyme synthesized by the plant by the process of cosuppression, in a manner similar to that discussed, for example, by Napoli et al., *Plant Cell* 2:279-290, 1990; and de Carvalho Niebel et al., *Plant Cell* 7:347-358, 1995.

The genetic constructs of the present invention further comprise a gene promoter sequence and a gene termination sequence, operably linked to the polynucleotide to be transcribed, which control expression of the gene. The gene promoter sequence is generally positioned at the 5' end of the polynucleotide to be transcribed, and is employed to initiate transcription of the polynucleotide. Gene promoter sequences are generally found in the 5' non-coding region of a gene but they may exist in introns (Luehrsen, *Mol. Gen. Genet.* 225:81-93, 1991). When the construct includes an open reading frame in a sense orientation, the gene promoter sequence also initiates translation of the open reading frame. For genetic constructs comprising either an open reading frame in an anti-sense orientation or a non-coding region, the gene promoter sequence consists only of a transcription initiation site having a RNA polymerase binding site.

A variety of gene promoter sequences that may be usefully employed in the genetic constructs of the present invention are well known in the art. The promoter gene sequence, and also the gene termination sequence, may be endogenous to the target plant host or may be exogenous, provided the promoter is functional in the target host. For example, the promoter and termination sequences may be from other plant species, plant viruses, bacterial plasmids and the like. Preferably, gene promoter and termination sequences are from the inventive sequences themselves.

Factors influencing the choice of promoter include the desired tissue specificity of the construct, and the timing of transcription and translation. For example, constitutive promoters, such as the 35S Cauliflower Mosaic Virus (CaMV 35S) promoter, will affect the activity of the enzyme in all parts of the plant. Use of a tissue specific promoter will result in production of the desired sense or anti-sense RNA only in the tissue of interest. With genetic constructs employing inducible gene promoter sequences, the rate of RNA polymerase binding and initiation can be modulated by external physical or chemical stimuli, such as light, heat, anaerobic stress, alteration in nutrient conditions and the like. Temporally regulated promoters can be employed to effect modulation of the rate of RNA polymerase binding and initiation at a specific time during development of a transformed cell. Preferably, the original promoters from the enzyme gene in question, or promoters from a specific tissue-targeted gene in the organism to be transformed, such as *Lolium* or *Festuca*, are used. Grass promoters different from the original gene may also be usefully employed in the inventive genetic constructs in order to prevent feedback inhibition. Other examples of gene promoters which may be usefully employed in the present invention include, mannopine synthase (mas), octopine synthase (ocs) and those reviewed by Chua et al., *Science* 244:174-181, 1989.

The gene termination sequence, which is located 3' to the polynucleotide to be transcribed, may come from the same gene as the gene promoter sequence or may be from a different gene. Many gene termination sequences known in the art may be usefully employed in the present invention, such as the 3' end of the *Agrobacterium tumefaciens* nopaline synthase gene. However, preferred gene terminator sequences are those from the original enzyme gene or from the target species to be transformed.

The genetic constructs of the present invention may also contain a selection marker that is effective in plant cells, to allow for the detection of transformed cells containing the inventive construct. Such markers, which are well known in the art, typically confer resistance to one or more toxins. One example of such a marker is the NPTII gene whose expression results in resistance to kanamycin or hygromycin, antibiotics which are usually toxic to plant cells at a moderate concentration (Rogers et al., in Weissbach A and H, eds., *Methods for Plant Molecular Biology*, Academic Press Inc.: San Diego, Calif., 1988). Alternatively, the presence of the desired construct in transformed cells can be determined by means of other techniques well known in the art, such as Southern and Western blots.

Techniques for operatively linking the components of the inventive genetic constructs are well known in the art and include the use of synthetic linkers containing one or more restriction endonuclease sites as described, for example, by Sambrook et al., *Molecular cloning: a laboratory manual*, CSHL Press: Cold Spring Harbor, N.Y., 1989. The genetic construct of the present invention may be linked to a vector having at least one replication system, for example, *E. coli*, whereby after each manipulation, the resulting construct can be cloned and sequenced and the correctness of the manipulation determined.

The genetic constructs of the present invention may be used to transform a variety of plants, both monocotyledonous (e.g., grasses, maize/corn, grains, oats, rice, sorghum, millet, rye, sugar cane, wheat and barley), dicotyledonous (e.g., *Arabidopsis*, tobacco, legumes, alfalfa, oaks, eucalyptus, maple), and gymnosperms. In a preferred embodiment, the inventive genetic constructs are employed to transform grasses. Preferably the target plant is selected from the group consisting of *Lolium* and *Festuca* species, most preferably from the group consisting of *Lolium perenne* and *Festuca arundinacea*. Other plants that may be usefully transformed with the inventive genetic constructs include other species of ryegrass and fescue, including, but not limited to, *Lolium multiflorum* (Italian ryegrass), *Lolium hybridum* (hybrid ryegrass), *Lolium rigidum* (Wimerra grass), *Lolium temulentum* (darnel), *Festuca rubra* (red fescue) and *Festuca pratensis* (meadow fescue). As discussed above, transformation of a plant with a genetic construct of the present invention will produce a modification in the flowering of the plant.

The production of RNA in target cells may be controlled by choice of the promoter sequence, or by selecting the number of functional copies or the site of integration of the polynucleotides incorporated into the genome of the target organism. A target plant may be transformed with more than one construct of the present invention, thereby modulating the flowering by affecting the activity of more than one enzyme, affecting enzyme activity in more than one tissue or affecting enzyme activity at more than one expression time. Similarly, a construct may be assembled containing more than one open reading frame coding for an enzyme encoded by a polynucleotide of the present invention or more than one non-coding region of a gene coding for such an enzyme. The polynucleotides of the present invention may also be employed in combination with other known sequences encoding enzymes involved in the flowering and/or other pathways. In this manner, more than one pathway may be modulated to produce a plant having an altered phenotype.

Techniques for stably incorporating DNA constructs into the genome of target plants are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by *Agrobacterium* Ti plasmid technology, as described, for example by Bevan, *Nucleic Acid Res.* 12:8711-8721, 1984. Targets for the introduction of the DNA constructs of the present invention include tissues, such as leaf tissue, disseminated cells, protoplasts, seeds, embryos, meristematic regions; cotyledons, hypocotyls, and the like. Transformation techniques which may be usefully employed in the inventive methods include those taught by Ellis et al., *Plant Cell Reports*, 8:16-20, 1989, Wilson et al., *Plant Cell Reports* 7:704-707, 1989; Tautorus et al., *Theor. Appl. Genet.* 78:531-536, 1989; and Ishida et al., *Nat. Biotechnol.* 14:745-750, 1996.

Once the cells are transformed, cells having the inventive genetic construct incorporated in their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. The resulting transformed plants may be reproduced sexually or asexually, using methods well known in the art, to give successive generations of transgenic plants.

Polynucleotides of the present invention may also be used to specifically suppress gene expression by methods that operate post-transcriptionally to block the synthesis of products of targeted genes, such as RNA interference (RNAi), and quelling. For a review of techniques of gene suppression see *Science*, 288:1370-1372, 2000. Exemplary gene silencing methods are also provided in WO 99/49029 and WO 99/53050. Posttranscriptional gene silencing is brought about by a sequence-specific RNA degradation process that results in the rapid degradation of transcripts of sequence-related genes. Studies have provided evidence that double-stranded RNA may act as a mediator of sequence-specific gene silencing (see, e.g., review by Montgomery and Fire, *Trends in Genetics*, 14:255-258, 1998). Gene constructs that produce transcripts with self-complementary regions are particularly efficient at gene silencing. A unique feature of this posttranscriptional gene silencing pathway is that silencing is not limited to the cells where it is initiated. The gene-silencing effects may be disseminated to other parts of an organism and even transmitted through the germ line to several generations.

The polynucleotides of the present invention may be employed to generate gene silencing constructs and or gene-specific self-complementary RNA sequences that can be delivered by conventional art-known methods to plant tissues, such as forage grass tissues. Within genetic constructs, sense and antisense sequences can be placed in regions flanking an intron sequence in proper splicing orientation with donor and acceptor splicing sites, such that intron sequences are removed during processing of the transcript and sense and antisense sequences, as well as splice junction sequences, bind together to form double-stranded RNA. Alternatively, spacer sequences of various lengths may be employed to separate self-complementary regions of sequence in the construct. During processing of the gene construct transcript, intron sequences are spliced-out, allowing sense and antisense sequences, as well as splice junction sequences, to bind forming double-stranded RNA. Select ribonucleases bind to and cleave the double-stranded RNA, thereby initiating the cascade of events leading to degradation of specific mRNA gene sequences, and silencing specific genes. Alternatively, rather than using a gene construct to express the self-complementary RNA sequences, the gene-specific double-stranded RNA segments are delivered to one or more targeted areas to be internalized into the cell cytoplasm to exert a gene silencing effect. Gene silencing RNA sequences comprising the polynucleotides of the present invention are useful for creating genetically modified plants with desired phenotypes as well as for characterizing genes (e.g., in high-throughput screening of sequences), and studying their functions in intact organisms.

The following examples are offered by way of illustration and not by way of limitation.

EXAMPLE 1

Isolation of cDNA Sequences from *L. perenne* and *F. arundinacea* cDNA Libraries

*L. perenne* and *F. arundinacea* cDNA expression libraries were constructed and screened as follows. Tissue was collected from *L. perenne* and *F. arundinacea* during winter and spring, and snap-frozen in liquid nitrogen. The tissues collected include those obtained from leaf blades, leaf base, pseudostem, roots and stem. Total RNA was isolated from each tissue type using TRIzol Reagent (BRL Life Technologies, Gaithersburg, Md.). mRNA from each tissue type was obtained using a Poly(A) Quik mRNA isolation kit (Stratagene, La Jolla, Calif.), according to the manufacturer's specifications. cDNA expression libraries were constructed from the purified mRNA by reverse transcriptase synthesis followed by insertion of the resulting cDNA in Lambda ZAP using a ZAP Express cDNA Synthesis Kit (Stratagene), according to the manufacturer's protocol. The resulting cDNA clones were packaged using a Gigapack II Packaging Extract (Stratagene) employing 1 μl of sample DNA from the 5 μl ligation mix. Mass excision of the libraries was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing 5-bromo-4-chloro-3-indolyl-beta-D-galactosidase (X-gal) and isopropylthio-beta-galactoside (IPTG).

Of the colonies plated and picked for DNA preparations, the large majority contained an insert suitable for sequencing. Positive colonies were cultured in NZY broth with kanamycin and DNA was purified following standard protocols. Agarose gel at 1% was used to screen sequencing templates for chromosomal contamination. Dye terminator sequences were prepared using a Biomek 2000 robot (Beckman Coulter Inc., Fullerton, Calif.) for liquid handling and DNA amplification using a 9700 PCR machine (Perkin Elmer/Applied Biosystems, Foster City, Calif.) according to the manufacturer's protocol.

The DNA sequences for positive clones were obtained using a Perkin Elmer/Applied Biosystems Division Prism 377 sequencer. cDNA clones were sequenced from the 5' end. The polynucleotide sequence identified as SEQ ID NO: 8 was identified from a *L. perenne* leaf cDNA expression library; the polynucleotide sequences identified as SEQ ID NO: 1, 3 and 7 were identified from *L. perenne* leaf and pseudostem cDNA expression libraries; the polynucleotide sequences identified as SEQ ID NO: 2 and 12 were identified from *L. perenne* floral stem cDNA expression libraries; the polynucleotide sequence identified as SEQ ID NO: 9 was identified from a *L. perenne* stem cDNA expression library; the polynucleotide sequence identified as SEQ ID NO: 5 was identified from a *L. perenne* root cDNA expression library; the polynucleotide sequences identified as SEQ ID NO: 4, 11 and 14 were identified from a *F. arundinacea* inflorescence (day 2) cDNA expression library; the polynucleotide sequences identified as SEQ ID NO: 13 and 16 were identified from a *F. arundinacea* cDNA expression library constructed from stem bases from day 7 inflorescences; the polynucleotide sequences identified as SEQ ID NO: 10 and 20 were identified from *F. arundinacea* pseudostem cDNA expression libraries; the polynucleotide sequences identified as SEQ ID NO: 15, 18 and 19 were identified from *F. arundinacea* leaf cDNA expression libraries; the polynucleotide sequence identified as SEQ ID NO: 6 was identified from *F. arundinacea* inflorescence cDNA expression libraries; and the polynucleotide sequence identified as SEQ ID NO: 17 was identified from a *F. arundinacea* rhizome cDNA expression library. SEQ ID NO: 1, 2, 6, 9-16, 18 and 20 represent full-length sequences, while SEQ ID NO: 3-5, 7, 8, 17 and 19 encode partial open reading frames.

BLASTN Polynucleotide Analysis

The isolated cDNA sequences were compared to sequences in the EMBL DNA database using the computer algorithm BLASTN. Comparisons of DNA sequences provided in SEQ ID NO: 1-17, 19 and 20, to sequences in the EMBL database (using BLASTN) were made as of Aug. 20, 2003, using BLASTN algorithm Version 2.2.1 [Apr. 13, 2001] and comparisons of the DNA sequence provided in SEQ ID NO: 18 to sequences in the EMBL database (using BLASTN) were made as of Aug. 26, 2003, using BLASTN algorithm Version 2.0.11 [Jan. 20, 2000], and the following Unix running command: blastall -p blastn -d embldb -e 10-G0 -E0 -FF -r 1-v 30-b 30-i queryseq -o.

The sequences of SEQ ID NO: 1-5,7-15 and 17-19 were determined to have less than 50% identity to sequences in the EMBL database using the computer algorithm BLASTN, as described above. The sequences of SEQ ID NO: 6, 16 and 20 were determined to have less than 75% identity to sequences in the EMBL database using the computer algorithm BLASTN, as described above.

BLASTP Polypeptide Analysis

The isolated cDNA sequences were compared to sequences in the SwissProt-TrEMBLE database using the computer algorithm BLASTP. Comparisons of protein sequences provided in SEQ ID NO: 21-37, 39 and 40 to sequences in the SwissProt-TrEMBLE protein database were made as of Aug. 15, 2003, using BLASTP algorithm Version 2.2.1 [Apr. 13, 2001] and comparisons of the protein sequence provided in SEQ ID NO: 38, to sequences in the SwissProt-TrEMBLE protein database were made as of Aug. 26, 2003, using BLASTP algorithm Version 2.0.11 [Jan. 20, 2000], and the following Unix running command: blastall -p blastp -d swissprottrembledb -e 10 -G0 -E0 -FF -v 30-b 30-i queryseq -o.

The amino acid sequences of SEQ ID NO: 31-33 were determined to have less than 50% identity to sequences in the SWISSPROT-TREMBLE database using the BLASTP computer algorithm as described above. The amino acid sequences of SEQ ID NO: 24, 55, 34, 35 and 38 were determined to have less than 75% identity to sequences in the SWISSPROT-TrEMBLE database using the computer algorithm BLASTP, as described above. The amino acid sequences of SEQ ID NO: 23, 26, 27, 29, 30, 36, 37 and 39 were determined to have less than 90% identity to sequences in the SWISSPROT-TrEMBLE database using the computer algorithm BLASTP, as described above. The amino acid sequences of SEQ ID NO: 21, 22, 28 and 40 were determined to have less than 98% identity to sequences in the SWISSPROT-TrEMBLE database using the computer algorithm BLASTP, as described above.

BLASTX Polynucleotide Analysis

The isolated cDNA sequences were compared to sequences in the SwissProt-TrEMBLE protein database using the computer algorithm BLASTX. Comparisons of DNA sequences provided in SEQ ID NO: 1-17, 19 and 20, to sequences in the SwissProt-TrEMBLE database (using BLASTX) were made as of Aug. 20, 2003 using BLAST algorithm Version 2.2.1 [Apr. 13, 2001] and comparisons of the DNA sequence provided in SEQ ID NO: 18 to sequences in the SwissProt-TrEMBLE protein database were made as of Aug. 26, 2003, using BLASTP algorithm Version 2.0.11 [Jan. 20, 2000], and the following Unix running command: blastall -p blastx -d swissprottrembledb -e 10 -G0 -E0 -FF -v 30 -b 30 -i queryseq -o.

The cDNA sequences of SEQ ID NO: 1-5, 7 and 11-16 were determined to have less than 50% identity to sequences in the SWISSPROT-TrEMBLE database using the computer algorithm BLASTX, as described above. The cDNA sequences of SEQ ID NO: 6, 8, 9, 10 and 17-20 were determined to have less than 75% identity to sequences in the SWISSPROT-TrEMBLE database using BLASTX, as described above.

The location of open reading frames (ORFs), by nucleotide position, contained within the sequences of SEQ ID NO: 1-20 and the corresponding amino acid sequences are provided in Table 2 below.

TABLE 2

| Polynucleotide SEQ ID NO: | ORF | Polypeptide SEQ ID NO: |
|---|---|---|
| 1 | 100-591 | 21 |
| 2 | 95-604 | 22 |
| 3 | 0-454 | 23 |
| 4 | 0-1967 | 24 |
| 5 | 0-1858 | 25 |
| 6 | 97-630 | 26 |
| 7 | 395-664 | 27 |
| 8 | 0-898 | 28 |
| 9 | 154-3600 | 29 |
| 10 | 189-3635 | 30 |
| 11 | 163-1653 | 31 |
| 12 | 336-1928 | 32 |
| 13 | 271-1671 | 33 |
| 14 | 109-2394 | 34 |
| 15 | 140-2413 | 35 |
| 16 | 81-605 | 36 |
| 17 | 0-1975 | 37 |
| 18 | 107-2533 | 38 |
| 19 | 0-2398 | 39 |
| 20 | 133-1962 | 40 |

EXAMPLE 2

Use of Grass Flowering Genes to Control Flowering

Transformation of *Arabidopsis* and *N. benthamiana* Plants with Grass Flowering Control Genes Sense constructs containing a polynucleotide including the coding region of flowering control genes isolated from *Lolium perenne* or *Festuca arundinacea* (SEQ ID NO: 1, 2, 6, 11, 12, 13, 14, 15, 15, 16) were inserted into a binary vector and used to transform *Agrobacterium tumefaciens* LBA4404 using published methods (see, An G, Ebert P R, Mitra A, Ha S B, "Binary Vectors," in Gelvin S B, Schilperoort R A, eds., *Plant Molecular Biology Manual*, Kluwer Academic Publishers: Dordrecht, 1988). The presence and integrity of the binary vector in *A. tumefaciens* was verified by polymerase chain reaction (PCR) utilizing vector primers.

The *A. tumefaciens* containing the sense gene constructs were used to transform *Arabidopsis* by floral dipping (Clough and Bent, *Plant J.* 16:735-743, 1998). Several independent transformed plant lines were established for the sense construct for each flowering gene. Transformed plants containing the appropriate flowering gene construct were verified using PCR experiments.

Effects of Grass FaFT Flowering Control Genes on Flowering Time in Transformed *Arabidopsis* Plants The *Arabidopsis* plant lines transformed with the *F. arundinacea* FT gene FLOWERING LOCUS T (FaFT) given in SEQ ID NO: 6 were grown for 70 days with 16 hours light and 8 hour night breaks (long day conditions). The plants were visually scored for first floral bud formation and flower opening every 3 days.

Figure 22:
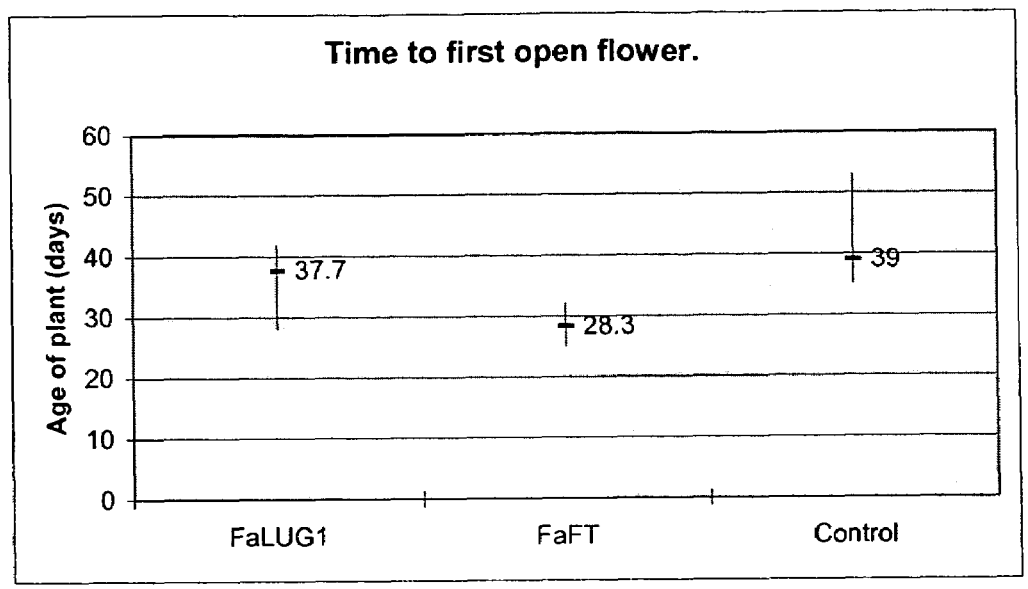
FIG. 22 shows the time to first open flowers for plants over-expressing the grass flowering time FLOWERING LOCUS T gene FaFT (SEQ ID NO: 6) and the grass LEUNIG gene FaLUG1 (SEQ ID NO: 14) under long day conditions.

FIG. 21 shows the time to first floral bud formation for plants over-expressing the grass flowering time gene FaFT (SEQ ID NO: 6) and plants containing the empty vector control. FIG. 22 shows the time to first open flowers in plants over-expressing grass flowering time gene FaFT (SEQ NO: 6) and plants containing the empty vector control. These results show that over-expression significantly reduced the time to floral bud formation and first open flowers under long day conditions.

Figure 23:
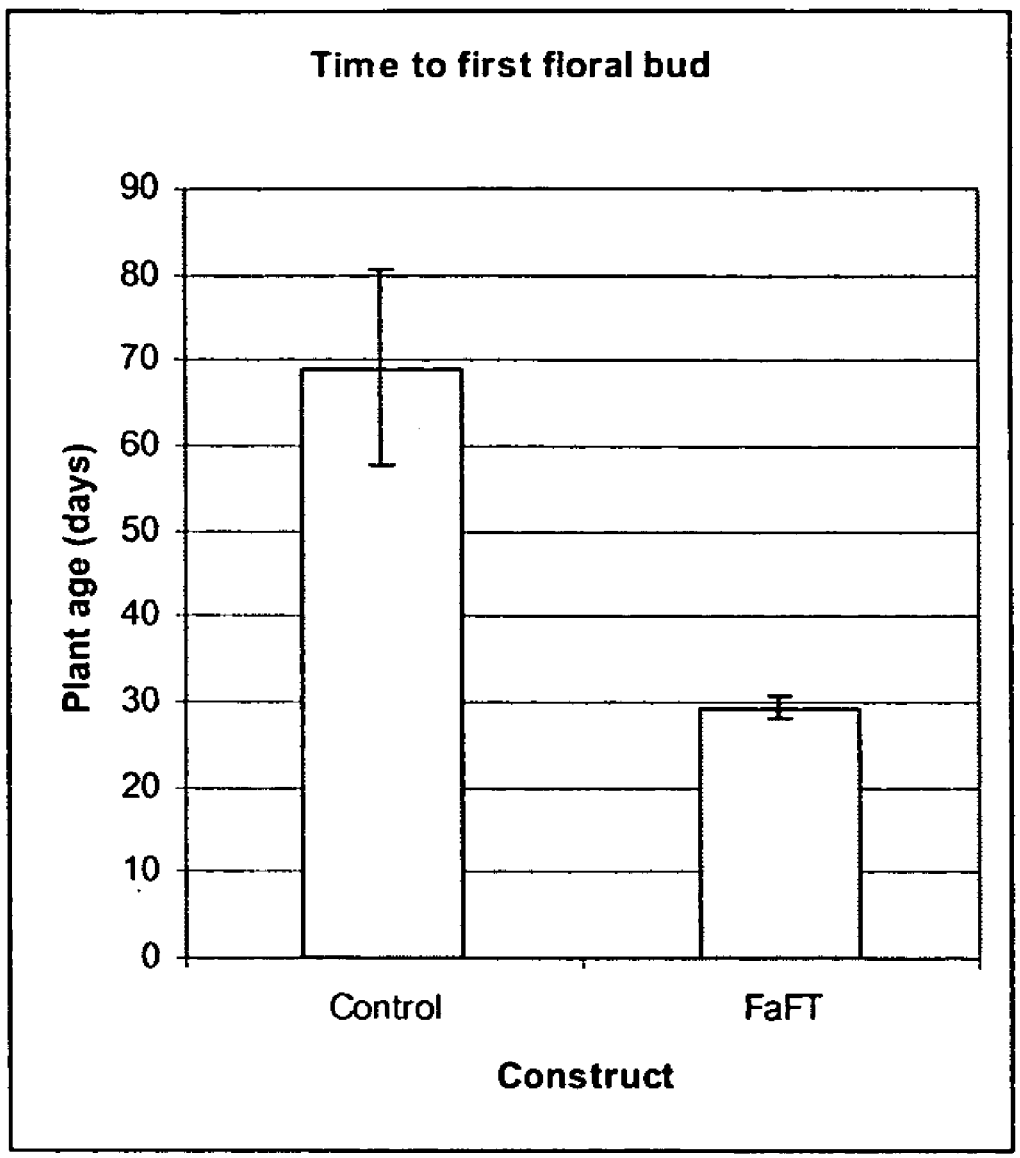
FIG. 23 shows the time to first floral bud formation for plants over-expressing the grass FLOWERING LOCUS T gene FaFT (SEQ ID NO: 6) under short day conditions. Bars represent standard deviation from the mean.
Figure 24:
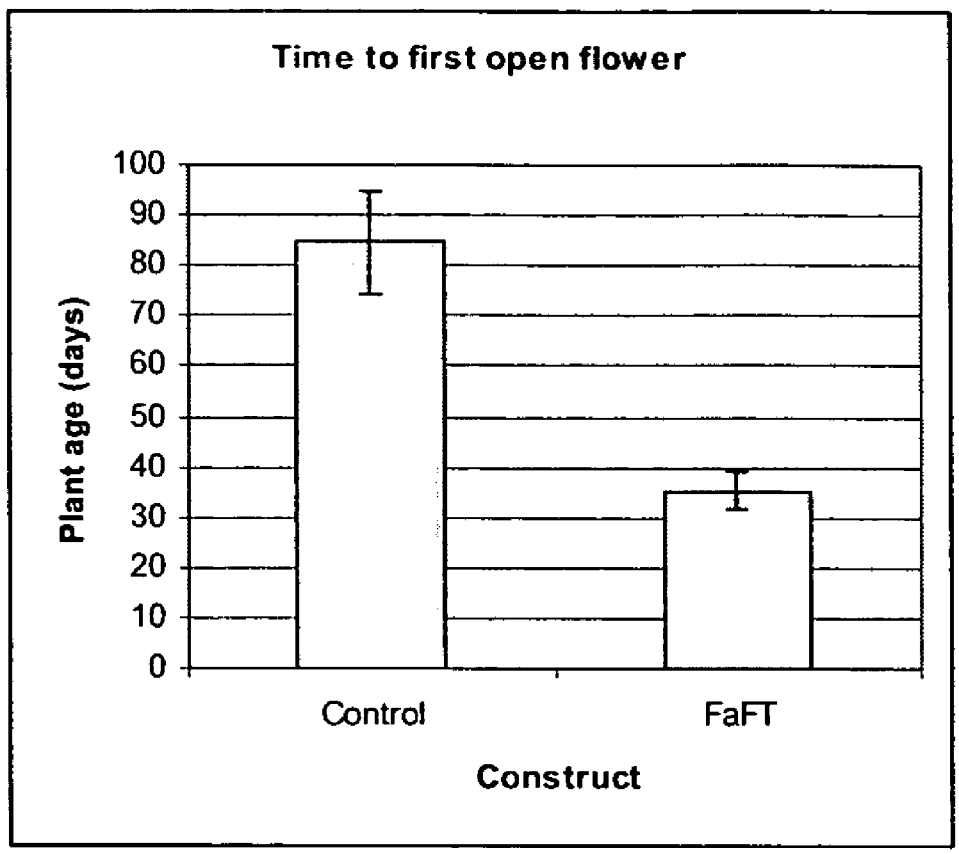
FIG. 24 shows the average time to first open flowers for plants over-expressing the grass FLOWERING LOCUS T gene FaFT (SEQ ID NO: 6) under short day conditions. Bars represent standard deviation from the mean.

The *Arabidopsis* plant lines transformed with *F. arundinacea* FaFT (SEQ ID NO: 6) were also grown under short day conditions and observed for time to flowering. Plants were grown for 90 days with 8 hours light and 16 hour night breaks and the plants were scored every three days. FIG. 23 shows the time to first floral bud formation for plants over-expressing the grass flowering time gene FaFT and plants containing the empty vector control, and FIG. 24 shows the time to first open flowers. These results show that over-expression of FaFT (SEQ ID NO: 6) significantly reduced the time to floral bud formation and first open flowers under short day conditions. Student t-test of the data results in a p-value of 0.0005 when comparing the control to the transgenic FaFT lines.

Effects of Grass FaLUG Flowering Control Genes on Flowering Time in Transformed *Arabidopsis* Plants The *Arabidopsis* plant lines transformed with the *F. arundinacea* LEUNIG gene (FaLUG) given in SEQ ID NO: 14 were grown for 70 days with 16 hours light and 8 hour night breaks (long day conditions). The plants were visually scored for first floral bud formation and flower opening every 3 days.

FIG. 22 shows the time to first open flowers in plants over-expressing grass flowering time LEUNIG gene FaLUG (SEQ NO: 14) and plants containing the empty vector control. These results show that over-expression reduced the time to first open flowers under long day conditions.

Figure 25:
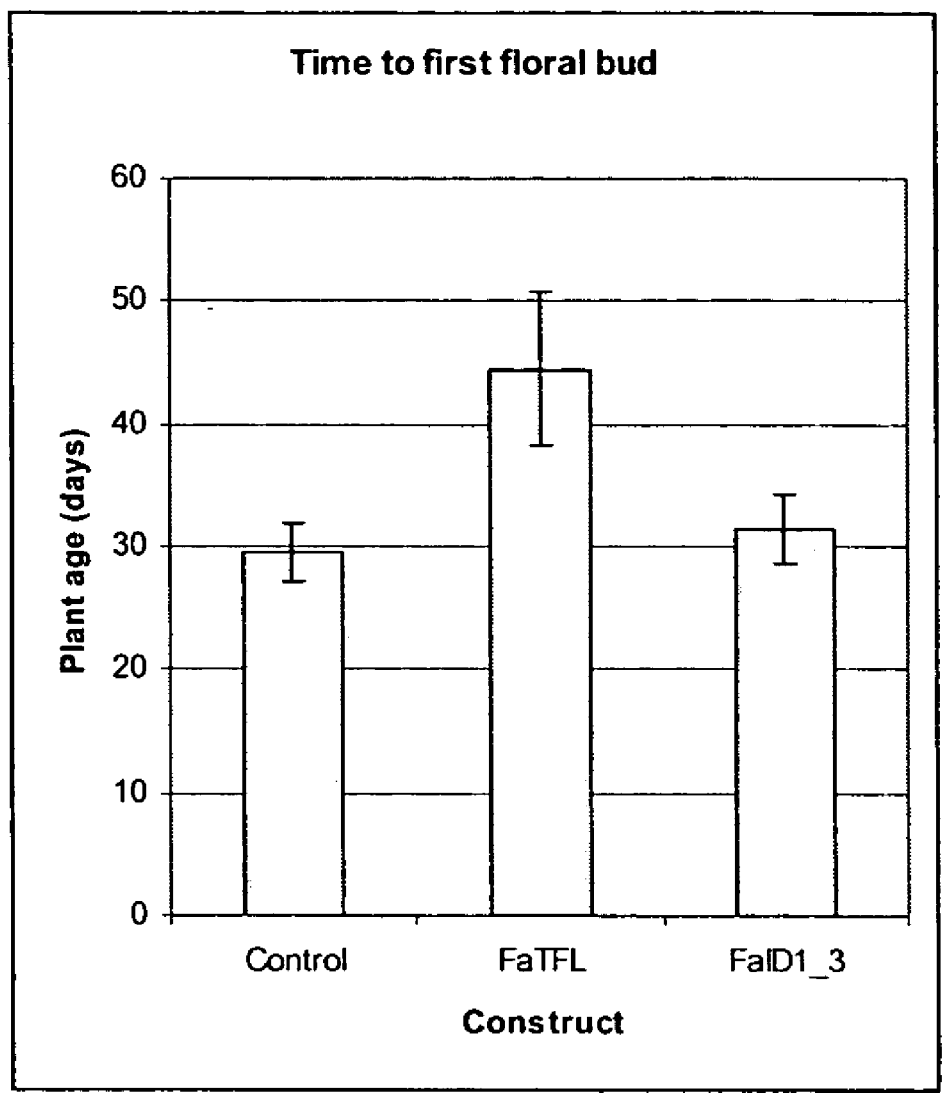
FIG. 25 shows the average time to first floral bud formation for plants over-expressing the grass Terminal Flower1 gene FaTFL (SEQ ID NO: 16) and the grass Indeterminate1-like gene FaID1_3 (SEQ ID NO: 13) under long day conditions. Bars represent standard deviation from the mean.
Figure 26:
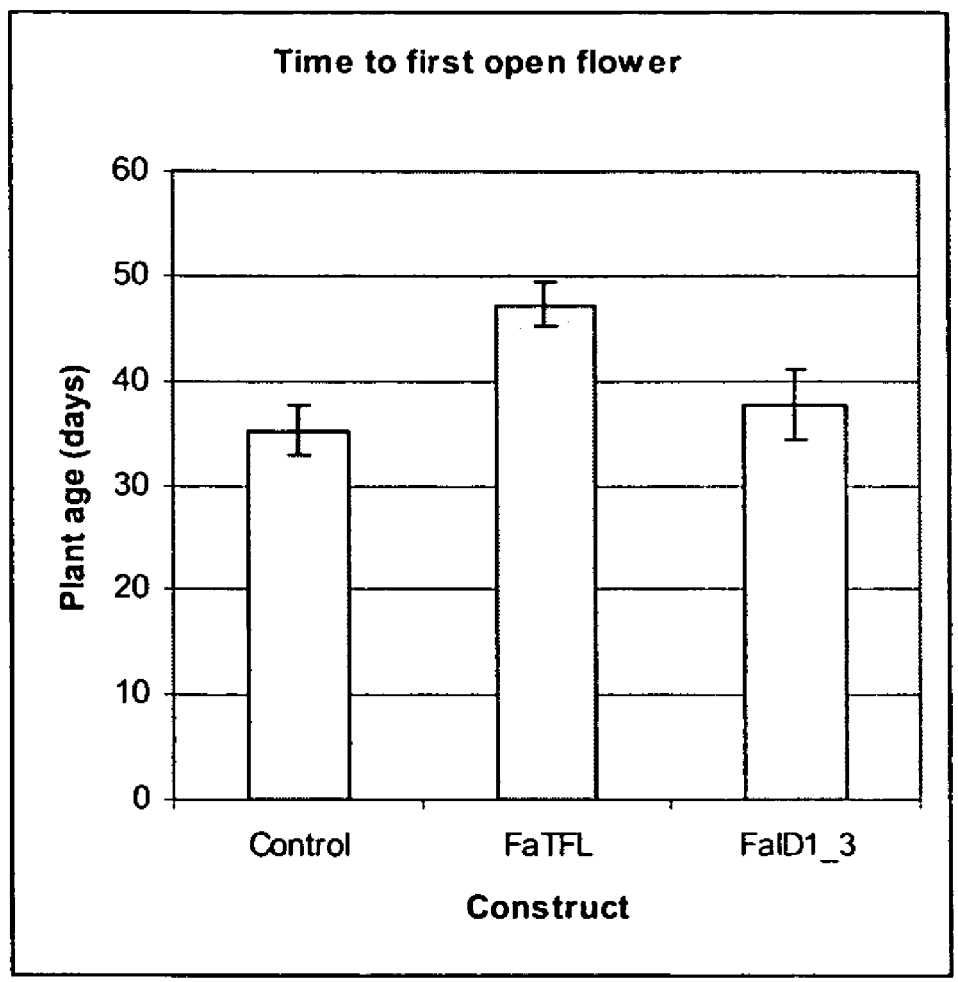
FIG. 26 shows the average time to first open flowers for plants over-expressing the grass Terminal Flower1 gene FaTFL (SEQ ID NO: 16) and the grass Indeterminate1-like gene FaID1_3 (SEQ ID NO: 13) under long day conditions. Bars represent standard deviation from the mean.

Effects of Grass FaTFL Flowering Control Gene on Flowering Time in Transformed *Arabidopsis* Plants The *Arabidopsis* plant lines transformed with the *F. arundinacea* Terminal Flower1 gene (FaTFL) given in SEQ ID NO: 16 were grown for 50 days with 16 hours light and 8 hour night breaks (long day conditions). The plants were visually scored for first floral bud formation and flower opening every 3 days. FIG. 25 shows the time to first floral bud formation in plants over-expressing FaTFL under long day conditions compared with empty vector control plants. These results show that over-expression of this gene severely delayed the time to flowering (student t-test p value <0.0005). In addition to the effect on flowering time, the transgene also had a severe effect on floral organ development. Visual observation revealed that when the floral structures appeared, most of them (>95%) were aberrant. The flowers contained no petals or gynoecia (or associated organs) and were primarily sepal-like. Trichomes present on the sepals appeared to be abnormal with altered branching and the sepals were more "hairy" in appearance. FIG. 26 shows the time to first open flowers, which is more a representation of unfurling of the sepals, compared with the empty vector control. The plants continued to grow vegetatively with elongated branching stems. In summary, normal flowering was severely reduced and the vegetative state extended in plants over-expressing FaTFL.

Effects of Grass FaID1_3 Flowering Control Gene on Flowering Time in Transformed *Arabidopsis* Plants The *Arabidopsis* plant lines transformed with the *F. arundinacea* Indeterminate1-like gene (FaID1_3) given in SEQ ID NO: 13 were grown for 50 days with 16 hours light and 8 hour night breaks (long day conditions). The plants were visually scored for first floral bud formation and flower opening every 3 days. FIG. 25 shows the time to first floral bud formation in plants over-expressing FaID1_3 and empty vector control plants, and FIG. 26 shows the time to first open flowers. The results showed that over-expression of the FaID1_3 gene in *Arabidopsis* results in a slight delay of the flowering events.

SEQ ID NO: 1-40 are set out in the attached Sequence Listing. The codes for nucleotide sequences used in the attached Sequence Listing, including the symbol "n," conform to WIPO Standard ST.25 (1998), Appendix 2, Table 1.

All references cited herein, including patent references and non-patent publications, are hereby incorporated by reference in their entireties.

While in the foregoing specification this invention has been described in relation to certain preferred embodiments, and many details have been set forth for purposes of illustration, it will be apparent to those skilled in the art that the invention is susceptible to additional embodiments and that certain of the details described herein may be varied considerably without departing from the basic principles of the invention.

We claim:

1. An isolated polynucleotide comprising SEQ ID NO: 16.

2. An isolated polynucleotide comprising a sequence selected from the group consisting of:
   (a) full-length complements of SEQ ID NO: 16;
   (b) full-length reverse complements of SEQ ID NO: 16; and
   (c) full-length reverse sequences of SEQ ID NO: 16.

3. An isolated polynucleotide comprising a sequence selected from the group consisting of:
   (a) sequences having at least 90% identity to SEQ ID NO: 16;
   (b) sequences having at least 95% identity to SEQ ID NO: 16; and
   (c) sequences that hybridize to SEQ ID NO: 16 in 0.2×SSC, 0.1% SDS at 65° C.,
   wherein the polynucleotide encodes a polypeptide that modifies time of flowering in plants.

4. An isolated polynucleotide that encodes a polypeptide of SEQ ID NO: 36.

5. A genetic construct comprising a polynucleotide of any one of claims 1-3.

6. A transgenic cell comprising a construct according to claim 5.

7. A genetic construct comprising, in the 5'-3' direction:
   (a) a gene promoter sequence;
   (b) a polynucleotide sequence comprising at least one of the following: (1) a polynucleotide coding for a polypeptide comprising SEQ ID NO: 36; and (2) a polynucleotide comprising a non-coding region of a polynucleotide of any one of claims 1-3; and
   (c) a gene termination sequence.

8. The genetic construct of claim 7, wherein the polynucleotide is in a sense orientation.

9. A transgenic plant cell comprising a genetic construct of claim 7.

10. A plant comprising a transgenic plant cell according to claim 9, or fruit or seeds or progeny thereof, wherein the fruit, seeds or progeny comprise the construct of claim 12.

11. A method for modulating flowering in a plant, comprising stably incorporating into the genome of the plant at least one polynucleotide of any one of claims 1-3.

12. The method of claim 11, wherein the plant is selected from the group consisting of grasses.

13. The method of claim 11, comprising stably incorporating into the genome of the plant a genetic construct comprising, in the 5'-3' direction:
   (a) a gene promoter sequence;
   (b) a polynucleotide sequence comprising at least one of the following: (1) a polynucleotide coding for a polypeptide comprising SEQ ID NO: 36; and (2) a polynucleotide comprising a non-coding region of a polynucleotide of any one of claims 1-3; and
   (c) a gene termination sequence.

14. The method of claim 13, wherein the promoter is an inducible promoter.

15. A method for producing a plant having altered flowering, comprising:
(a) transforming a plant cell with a genetic construct of claim 7 to provide a transgenic cell; and
(b) cultivating the transgenic cell under conditions conducive to regeneration and mature plant growth.

16. The method of claim 15, wherein the promoter is an inducible promoter and the plant cell is exposed to an inducing agent selected from the group consisting of: chemical and physical stimuli.

17. A method for modifying the activity of a polypeptide involved in a flowering pathway in a plant comprising stably incorporating into the genome of the plant a construct of claim 7.

* * * * *

UNITED STATES PATENT AND TRADEMARK OFFICE
CERTIFICATE OF CORRECTION

| | | |
|---|---|---|
| PATENT NO. | : 7,538,260 B2 | Page 1 of 1 |
| APPLICATION NO. | : 11/110082 | |
| DATED | : May 26, 2009 | |
| INVENTOR(S) | : Jeroen Demmer et al. | |

It is certified that error appears in the above-identified patent and that said Letters Patent is hereby corrected as shown below:

| Col. No. | Line(s) | |
|---|---|---|
| 124 | (48) | Within Claim 10, please change "Claim 12" to "Claim 7" |

Signed and Sealed this
Eighteenth Day of September, 2012

David J. Kappos
*Director of the United States Patent and Trademark Office*